(12) United States Patent
Okada et al.

(10) Patent No.: US 7,112,593 B2
(45) Date of Patent: *Sep. 26, 2006

(54) N-ARYL-SUBSTITUTED CYCLIC AMINE DERIVATIVE AND MEDICINE CONTAINING THE SAME AS ACTIVE INGREDIENT

(75) Inventors: Toshimi Okada, Ibaraki (JP); Nobuyuki Kurusu, Ibaraki (JP); Keigo Tanaka, Ibaraki (JP); Seiji Yoshikawa, Ibaraki (JP); Daisuke Shinmyo, Ibaraki (JP); Nobuhisa Watanabe, Ibaraki (JP); Hironori Ikuta, Ibaraki (JP); Hironobu Hiyoshi, Ibaraki (JP); Takao Saeki, Ibaraki (JP); Mamoru Yanagimachi, Ibaraki (JP); Masashi Ito, Chiba (JP)

(73) Assignee: Eisai Co., Ltd., Tokyo (JP)

( * ) Notice: Subject to any disclaimer, the term of this patent is extended or adjusted under 35 U.S.C. 154(b) by 14 days.

This patent is subject to a terminal disclaimer.

(21) Appl. No.: 10/470,675

(22) PCT Filed: Mar. 27, 2002

(86) PCT No.: PCT/JP02/03004

§ 371 (c)(1),
(2), (4) Date: Jul. 30, 2003

(87) PCT Pub. No.: WO02/076973

PCT Pub. Date: Oct. 3, 2002

(65) Prior Publication Data

US 2004/0072830 A1  Apr. 15, 2004

(30) Foreign Application Priority Data

Mar. 27, 2001 (JP) .............................. 2001-091480

(51) Int. Cl.
  A61K 31/44 (2006.01)
  C07D 453/02 (2006.01)
(52) U.S. Cl. .................. 514/305; 514/343; 546/133; 546/137; 548/305; 548/343
(58) Field of Classification Search ............... 546/133, 546/137, 276.4; 548/541; 514/305, 343
  See application file for complete search history.

(56) References Cited

U.S. PATENT DOCUMENTS 5,714,496 A   2/1998 Brown et al.
6,599,917 B1 * 7/2003 Okada et al. ............... 514/305

FOREIGN PATENT DOCUMENTS

| EP | 73997 A1 | 3/1983 |
|---|---|---|
| EP | 1035115 A1 | 9/2000 |
| JP | 7-502283 A | 3/1995 |
| JP | 8-502731 A | 3/1996 |
| JP | 8-504803 A | 5/1996 |
| JP | 8-509488 A | 10/1996 |
| WO | WO 92/15579 A1 | 9/1992 |
| WO | WO 93/13096 A1 | 7/1993 |
| WO | WO 94/05660 A1 | 3/1994 |
| WO | WO 94/14805 A1 | 7/1994 |
| WO | WO 94/25459 A1 | 11/1994 |
| WO | WO 01/23383 A1 | 4/2001 |

OTHER PUBLICATIONS

Kobayashi et al. , 1994,CAS:120:164907.*

* cited by examiner

Primary Examiner—Kamal A. Saeed
Assistant Examiner—Robert Shiao
(74) Attorney, Agent, or Firm—Birch, Stewart, Kolasch, and Birch, LLP

(57) ABSTRACT

An excellent squalene synthase inhibitor is provided. Specifically, what is provided is a compound (I) represented by the following formula, a salt thereof or a hydrate of them. In formula (I), $R^1$ represents an optionally substituted vinyl group or an aromatic ring which may be substituted. Also, n is an integer of 0 to 2. Further, X, Y and Z are the same as or different from each other and each represents an optionally substituted carbon atom, or an optionally substituted nitrogen atom, sulfur atom or oxygen atom, and Y optionally represents a single bond, and when Y represents the single bond, the ring to which X, Y and Z belong is a 5-membered ring. Also in the formula, CyA represents a 5- to 14 membered non-aromatic cyclic amino group or non-aromatic cyclic amido group which may be substituted, and the non-aromatic cyclic amino group or the non-aromatic cyclic amido group optionally having an oxygen atom or a sulfur atom. Finally, W represents a chain

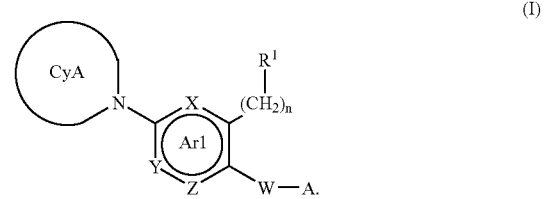

(I)

12 Claims, No Drawings

N-ARYL-SUBSTITUTED CYCLIC AMINE DERIVATIVE AND MEDICINE CONTAINING THE SAME AS ACTIVE INGREDIENT

This application is the national phase under 35 U.S.C. § 371 of PCT International Application No. PCT/JP02/03004 which has an International filing date of Mar. 27, 2002, which designated the United States of America.

TECHNICAL FIELD

The present invention relates to a novel compound, a method for producing the it, a squalene synthase inhibitor, a cholesterol biosynthesis inhibitor and a triglyceride biosynthesis inhibitor containing such a novel compound and also to a medicinal composition containing them. More specifically, the present invention relates to preventive and curative agents for hyperlipidemia including arterial sclerosis diseases and ischemic heart diseases.

PRIOR ART

Cholesterol is a sterol which is biosynthesized in all animal cells except for a red blood cell and is a substance essential for maintaining a plasma membrane and for the creation of a steroid hormone. Cholesterol is liposoluble and exists as low-density lipoprotein (LDL), high-density lipoprotein (HDL) and the like in blood. LDL in blood is incorporated into cells through a receptor on the surface of the cells and regenerates free cholesterol after decomposed. This is a major route for incorporating cholesterol from the outside of cells. Also, it has been known that a major enzyme which participates in the biosynthesis of LDL receptor protein and cholesterol undergoes feedback of the concentration of cholesterol which is the harvested product. In this manner, the level of cholesterol in cells is maintained and controlled exquisitely by the feedback control mechanism of the LDL receptor and biosynthetic type enzyme on the basis of a balance between the biosynthesis of a cell itself and the incorporation of LDL from the outside of a cell.

The squalene synthase is a membrane-bound enzyme of 47-kDa and reducibly catalyzes the head-to-head condensation of two molecules of FPP to synthesize squalene which is an intermediate for the synthesis of cholesterol. In a cholesterol-biosynthesis system, the squalene synthase is positioned downstream of a system generating the HMG-CoA reductase and isoprene and therefore the squalene synthase inhibitor is considered to have almost no effect on metabolic systems other than cholesterol and is therefore expected to work as a new cholesterol depressor which will solve the problems concerning the HMG-CoA reductase inhibitor. A squalene synthase inhibitor which was reported first is analogous compounds of FPP and squalene. However, these analogous compounds has an activity inhibiting the formation of prenyl protein and the like in addition to squalene synthase inhibitive action and it is difficult to put these analogous compounds to practical use. In the meantime, it has been disclosed recently that a certain type substituted phenylethynylquinuclidine compound and substituted pyridinylethynylquinuclidine compound are useful as a squalene synthase inhibitor in JP-A 7-502283, 8-502731, 8-504803 (U.S. Pat. No. 5,731,323) and 8-509488. However, no squalene synthase inhibitor which can produce an effect as a medicine for hyperlipidemia has been created so far.

That is, an object of the present invention is to search and to find a compound which has stronger squalene synthase inhibitive activities and cholesterol depressing action over those currently in use and is useful as a remedy for hyperlipidemia.

DISCLOSURE OF THE INVENTION

In view of the above situation, the inventors of the present invention have made earnest studies and as a result, found that a specific quinuclidine compound and its salt have unprecedented strong squalene synthase inhibitive activities. The inventors have also found that these compounds and their salts have strong cholesterol biosynthesis inhibitive activities, triglyceride biosynthesis inhibitive activities and serum cholesterol depressing action and serum triglyceride depressing action based on the inhibition of squalene synthase. The present invention has been thus completed. A compound according to the present invention is useful as a remedy for hyperlipidemia.

The present invention is a compound (I) represented by the formula:

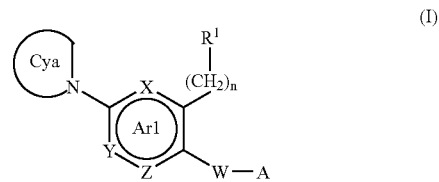

(wherein $R^1$ represents an optionally substituted vinyl group or an aromatic ring which may be substituted;

n is an integer of 0 to 2;

X, Y, and Z are the same as or different from each other and each represents an optionally substituted carbon atom, or an optionally substituted nitrogen atom, sulfur atom or oxygen atom, and Y may represent a single bond and when Y represents the single bond, the ring to which X, Y and Z belong is a 5-membered;

CyA represents a 5- to 14 membered non-aromatic cyclic amino group or non-aromatic cyclic amido group, each of which may be substituted, and the non-aromatic cyclic amino group or the non-aromatic cyclic amido group may contain an oxygen atom or a sulfur atom;

W represents a chain expressed by
(1) optionally substituted —$CH_2$—$CH_2$—,
(2) optionally substituted —CH=CH—,
(3) —C≡C—,
(4) an optionally substituted phenylene group,
(5) a single bond,
(6) —NH—CO—,
(7) —CO—NH—,
(8) —NH—$CH_2$—,
(9) —$CH_2$—NH—,
(10) —$CH_2$—CO—,
(11) —CO—$CH_2$—,
(12) —O—$(CH_2)_m$—,
(13) —$(CH_2)_m$—O— (where m represents an integer of 0 to 5),
(14) —O—$CH_2$—$CR^2$=,
(15) —O—$CH_2$—$CHR^2$— (where $R^2$ represents a hydrogen atom, a $C_{1-6}$ alkyl group, or a halogen atom),
(16) —NH—$S(O)_l$—,
(17) —$S(O)_l$—NH—,
(18) —$CH_2$—$S(O)_l$— or
(19) —$S(O)_l$—$CH_2$— (where l represents 0, 1, or 2); and A represents a group having any of the following structural formulae:

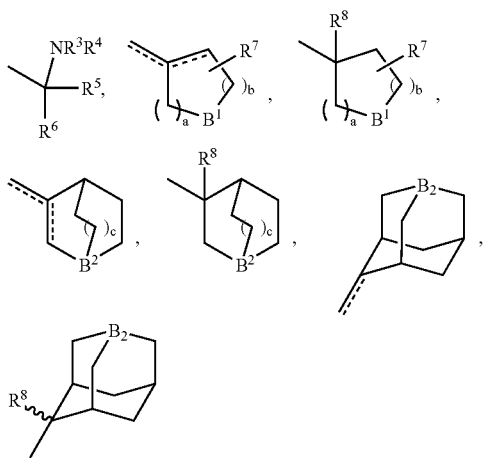

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------- represents a single bond or a double bond, provided that when c is 1 in which A is a quinuclidine having $R^8$ represented by

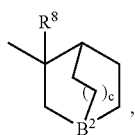

the case where $R^8$ is a hydrogen atom or a hydroxyl group; ArI is an aromatic heterocycle; and W is one of (1) to (3), (6) to (11) and (16) to (19) are excluded)), a salt thereof or a hydrate of them.

The present invention is a compound, in the abovementioned compound (I), $R^1$ represents an optionally substituted vinyl group, a benzene ring which may be substituted or a thiophene ring which may be substituted;

n is an integer of 0 to 2;

ArI represents a benzene ring, pyridine ring, pyrimidine ring, pyrazine ring, pyridazine ring, triazine ring, thiazole ring, thiophene ring, pyrrole ring or furan ring, each of which may be substituted with a lower alkyl group, a halogen atom or an alkoxy group;

CyA represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group;
W represents a chain expressed by
(1) optionally substituted —$CH_2$—$CH_2$—,
(2) optionally substituted —CH=CH—,
(3) —C≡C—,
(4) an optionally substituted phenylene group,
(5) a single bond,
(6) —NH—CO—,
(7) —CO—NH—,
(8) —NH—$CH_2$—,
(9) —$CH_2$—NH—,
(10) —$CH_2$—CO—,
(11) —CO—$CH_2$—,
(12) —O—$(CH_2)_m$—,
(13) —$(CH_2)_m$—O— (where m represents an integer of 0 to 5),
(14) —O—$CH_2$—$CR^2$=,
(15) —O—$CH_2$—CHR— (where $R^2$ represents a hydrogen atom, a $C_{1-6}$ alkyl group, or a halogen atom),
(16) —NH—$S(O)_l$—,
(17) —$S(O)_l$—NH—,
(18) —$CH_2$—$S(O)_l$— or
(19) —$S(O)_l$—$CH_2$— (where l represents 0, 1, or 2); and
A represents a group having any of the following structural formulae:

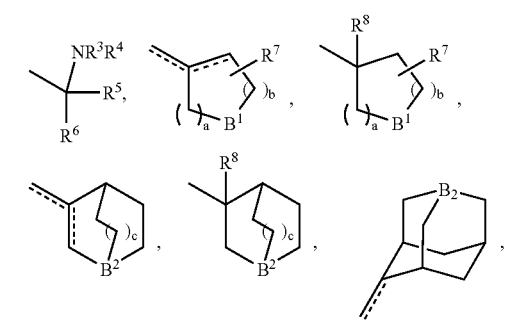

-continued

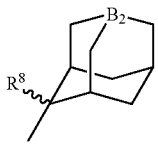

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having $R^8$ represented by

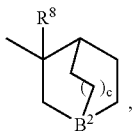

the case where $R^8$ is a hydrogen atom or a hydroxyl group; ArI is an aromatic heterocycle; and W is one of (1) to (3), (6) to (11) and (16) to (19) are excluded), a salt thereof or a hydrate of them.

The present invention is also a compound, in the above-mentioned compound (I), ArI preferably represents a benzene ring, pyridine ring, pyrimidine ring or thiazole ring optionally substituted with a lower alkyl group, a halogen atom or an alkoxy group;

$R^1$ represents an optionally substituted vinyl group, a benzene ring which may be substituted or a thiophene ring which may be substituted;

n is an integer of 0 to 2;

CyA represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other selected from:

(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group;

W represents a chain expressed by
(1) optionally substituted —$CH_2$—$CH_2$—,
(2) optionally substituted —CH═CH—,
(3) —C≡C—,
(4) an optionally substituted phenylene group,
(5) a single bond,
(6) —NH—CO—,
(7) —CO—NH—,
(8) —NH—$CH_2$—,
(9) —$CH_2$—NH—,
(10) —$CH_2$—CO—,
(11) —CO—$CH_2$—,
(12) —O—$(CH_2)_m$—,
(13) —$(CH_2)_m$—O— (where m represents an integer of 0 to 5),
(14) —O—$CH_2$—$CR^2$≡,
(15) —O—$CH_2$—CHR— (where $R^2$ represents a hydrogen atom, a $C_{1-6}$ alkyl group, or a halogen atom),
(16) —NH—$S(O)_l$—,
(17) —$S(O)_l$—NH—,
(18) —$CH_2$—$S(O)_l$— or
(19) —$S(O)_l$—$CH_2$— (where l represents 0, 1, or 2); and A represents a group having any of the following structural formulae:

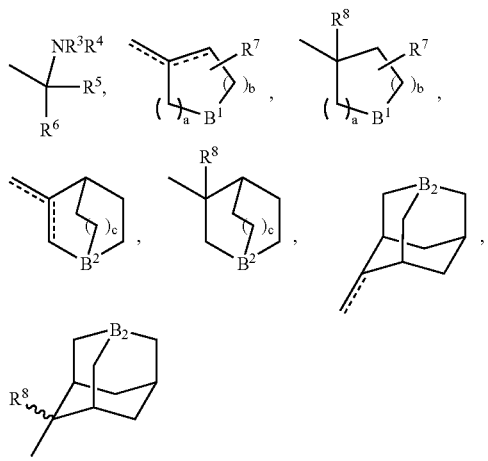

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having $R^8$ represented by

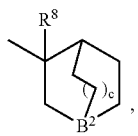

the case where $R^8$ is a hydrogen atom or a hydroxyl group; Arl is an aromatic heterocycle; and W is one of (1) to (3), (6) to (11) and (16) to (19) are excluded), a salt thereof or a hydrate of them.

Further, the present invention is a compound, in the above-mentioned compound (I), W preferably represents a chain expressed by (1) optionally substituted —CH$_2$—CH$_2$—,
(2) optionally substituted —CH=CH—,
(3) —C≡C—,
(4) an optionally substituted phenylene group,
(5) a single bond,
(13) —(CH$_2$)$_m$—O— (where m represents an integer of 0 to 5),
(14) —O—CH$_2$—CR$^2$=, or
(15) —O—CH$_2$—CHR— (where $R^2$ represents a hydrogen atom, an alkyl group or a halogen atom);

$R^1$ represents an optionally substituted vinyl group, a benzene ring which may be substituted or a thiophene ring which may be substituted;

n is an integer of 0 to 2;

Arl represents a benzene ring, pyridine ring, pyrimidine ring, pyrazine ring, pyridazine ring, triazine ring, thiazole ring, thiophene ring, pyrrole ring or furan ring, each of which may be substituted with a lower alkyl group, a halogen atom or an alkoxy group;

CyA represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other selected from:

(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group,
(17) an alkoxycarbonyloxy group; and A represents a group having any of the following structural formulae:

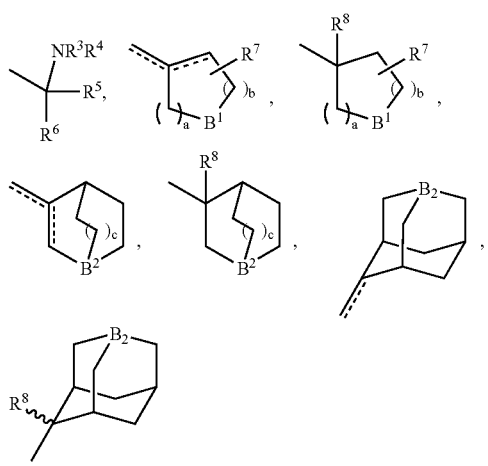

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having $R^8$ represented by

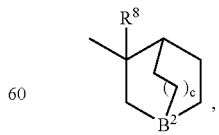

the case where $R^8$ is a hydrogen atom or a hydroxyl group; Arl is an aromatic heterocycle; and W is one of (1) to (3), (6) to (11) and (16) to (19) are excluded), a salt thereof or a hydrate of them.

Also, the present invention is a compound, in the above-mentioned compound (I), Arl preferably represents a benzene ring, pyridine ring, pyrimidine ring or thiazole ring, each of which may be substituted with a lower alkyl group, a halogen atom or an alkoxy group;

W preferably represents a chain expressed by
(1) optionally substituted —$CH_2$—$CH_2$—,
(2) optionally substituted —CH=CH—,
(3) —C≡C—,
(4) an optionally substituted phenylene group,
(5) a single bond,
(13) —$(CH_2)_m$—O— (where m represents an integer of 0 to 5),
(14) —O—$CH_2$—$CR^2$=, or
(15) —O—$CH_2$—$CHR^2$— (where $R^2$ represents a hydrogen atom, an alkyl group or a halogen atom);

$R^1$ represents an optionally substituted vinyl group, a benzene ring which may be substituted or a thiophene ring which may be substituted;

n is an integer of 0 to 2;

CyA represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other and selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group; and A represents a group having any of the following structural formulae:

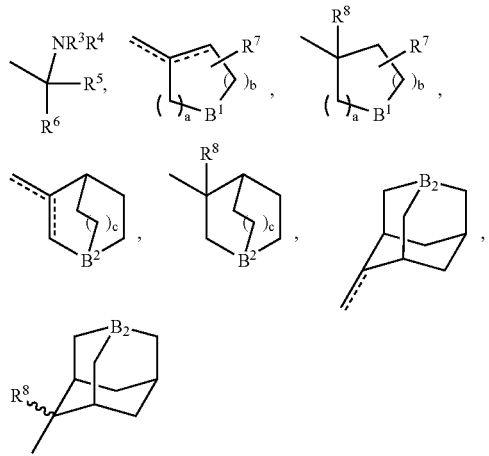

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having $R^8$ represented by

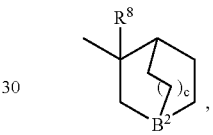

the case where $R^8$ is a hydrogen atom or a hydroxyl group; Arl is an aromatic heterocycle; and W is one of (1) to (3), (6) to (11) and (16) to (19) are excluded), a salt thereof or a hydrate of them.

Also, the present invention is a compound, in the above-mentioned compound (I), Arl preferably represents a benzene ring, pyridine ring, pyrimidine ring or thiazole ring, each of which may be substituted with a lower alkyl group, a halogen atom or an alkoxy group;

W preferably represents a chain expressed by
(1) optionally substituted —$CH_2$—$CH_2$—,
(2) optionally substituted —CH=CH—,
(3) —C≡C—,
(4) an optionally substituted phenylene group,
(5) a single bond,
(13) —$(CH_2)_m$—O— (where m represents an integer of 0 to 5),
(14) —O—$CH_2$—$CR^2$=, or
(15) —O—$CH_2$—$CHR^2$— (where $R^2$ represents a hydrogen atom, an alkyl group or a halogen atom);

CyA preferably represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other selected from:
(1) a lower alkyl group which may be substituted,
(4) a lower alkoxy group which may be substituted,
(5) an oxo group,
(7) an alkylenedioxy group,
(8) a hydroxyl group, and
(9) a halogen atom;

$R^1$ represents an optionally substituted vinyl group, a benzene ring which may be substituted or a thiophene ring which may be substituted;

n is an integer of 0 to 2; and

A represents a group having any of the following structural formulae:

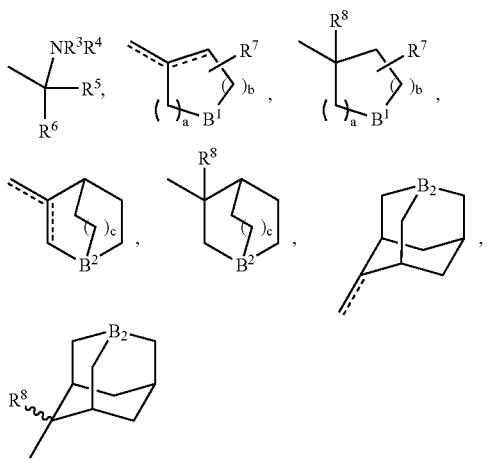

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------- represents a single bond or a double bond, provided that when c is 1 in which A is a quinuclidine having $R^8$ represented by

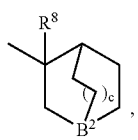

the case where $R^8$ is a hydrogen atom or a hydroxyl group; ArI is an aromatic heterocycle; and W is one of (1) to (3), (6) to (11) and (16) to (19) are excluded), a salt thereof or a hydrate of them.

Also, the present invention is a compound, in the above-mentioned compound (I), ArI preferably represents a benzene ring, pyridine ring, pyrimidine ring or thiazole ring, each of which may be substituted with a lower alkyl group, a halogen atom or an alkoxy group;

W preferably represents a chain expressed by
(1) optionally substituted $-CH_2-CH_2-$,
(2) optionally substituted $-CH=CH-$,
(3) $-C\equiv C-$,
(4) an optionally substituted phenylene group,
(5) a single bond,
(13) $-(CH_2)_m-O-$ (where m represents an integer of 0 to 5),
(14) $-O-CH_2-CR^2=$, or
(15) $-O-CH_2-CHR^2-$ (where $R^2$ represents a hydrogen atom, an alkyl group or a halogen atom);

CyA represents an azetidine ring, pyrrolidine ring, piperidine ring, piperazine ring, morpholine ring, 2-azetidinone ring, 2-pyrrolidinone ring, 2-piperidinone ring, 2-piperazinone ring or 3-morpholine ring, each of which may be substituted with one to three groups which are the same as or different from each other and selected from:
(1) a lower alkyl group which may be substituted,
(4) a lower alkoxy group which may be substituted,
(5) an oxo group,
(7) an alkylenedioxy group,
(8) a hydroxyl group, and
(9) a halogen atom;

$R^1$ represents a benzene ring which may be substituted;

n is an integer of 0 to 2; and

A represents a group having any of the following structural formulae:

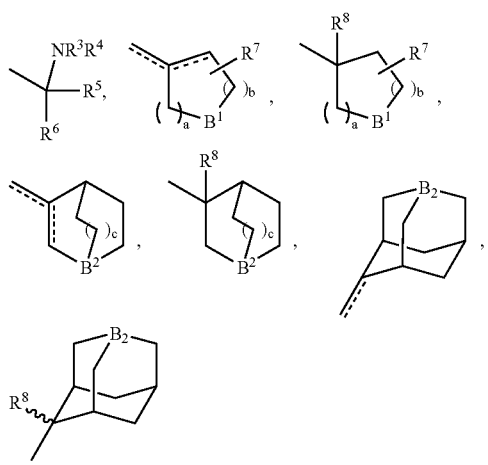

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, B¹ represents an optionally substituted carbon atom, or an optionally substituted nitrogen atom, oxygen atom or sulfur atom;

B² represents an optionally substituted carbon atom or nitrogen atom;

a and b represent an integer of 0 to 4, provided that a+b is an integer of 0 to 4, c represents 0 or 1; and ------- represents a single bond or a double bond, provided that when c is 1 in which A is a quinuclidine having $R^8$ represented by

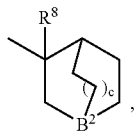

the case where $R^8$ is a hydrogen atom or a hydroxyl group; Arl is an aromatic heterocycle; and W is one of (1) to (3), (6) to (11) and (16) to (19) are excluded) a salt thereof or a hydrate of them.

The present invention is a compound selected from the group consisting of:

3-[2-benzyl-6-[(3R,4R)-3-hydroxy-4-methoxypyrrolidin-1-yl]-3-pyridyl]ethynyl-3-piperidinol;

3-[2-benzyl-6-[(3R,4R)-3-hydroxy-4-methoxypyrrolidin-1-yl]-3-pyridyl]ethynyl-1-methyl-3-piperidinol;

4-[2-benzyl-6-[(3R,4R)-3-hydroxy-4-methoxypyrrolidin-1-yl]-3-pyridyl]-1-methyl-4-piperidinol;

4-[2-benzyl-6-[(3R,4R)-3-hydroxy-4-methoxypyrrolidin-1-yl]-3-pyridyl]-1-methyl-1,2,3,6-tetradydropyridine;

3-[3-[2-benzyl-6-[(3R,4R)-3-hydroxy-4-methoxypyrrolidin-1-yl]-3-pyridyl]propyloxy]pyrrolidine;

1-[2-benzyl-6-[(3R,4S)-3-hydroxy-4-methoxypyrrolidin-1-yl]-3-pyridyl]ethynylcyclohexylamine;

1-[2-benzyl-6-[(3R,4R)-3-hydroxy-4-methoxypyrrolidin-1-yl]-3-pyridyl]ethynylcyclohexylamine;

1-[2-benzyl-6-[(3R,4R)-3,4-dimethoxy-2-pyrrolidinon-1-yl]-3-pyridyl]ethynylcyclohexylamine;

1-[2-benzyl-6-[(3R,4R)-4-hydroxy-3-methoxy-2-pyrrolidinon-1-yl]-3-pyridyl]ethynylcyclohexylamine;

1-[1-[2-benzyl-6-[(3R,4R)-3-hydroxy-4-methoxypyrrolidin-1-yl]-3-pyridyl]ethynylcyclohexyl]piperidine;

1-[2-benzyl-6-[(3R,4R)-3-hydroxy-4-methoxypyrrolidin-1-yl]-3-pyridyl]ethynyl-N-methycyclohexylamine;

2-[[1-[2-benzyl-6-[(3R,4R)-3-hydroxy-4-methoxypyrrolidin-1-yl]-3-pyridyl]ethynylcyclohexyl]amino]ethanol;

3-[2-benzyl-6-[(3R,4R)-3-hydroxy-4-methoxypyrrolidin-1-yl]-3-pyridyl]-1,1-diethyl-2-propynylamine;

2-[2-benzyl-6-[(3R,4R)-3-hydroxy-4-methoxypyrrolidin-1-yl]-3-pyridyl]ethynylbicyclo[2.2.1]heptan-2ol;

(3R)-3-[2-benzyl-4-(2-pyrrolidinon-1-yl)phenyl]ethynyl-3-quinuclidinol;

(3R)-3-[2-benzyl-4-[(3R,4R)-4-hydroxy-3-methoxy-2-pyrrolidinon-1-yl]phenyl]ethylnyl-3-quinuclidinol;

(3R)-3-[2-benzyl-4-[(3R,4R)-3,4-dimethoxy-2-pyrrolidinon-1-yl]phenyl]ethynyl-3-quinuclidinol;

(3R)-3-[2-benzyl-4-[(3R,4S)-3,4-dimethoxypyrrolidin-1-yl)phenyl]ethynyl-3-quinuclidinol;

(3R)-3-[2-benzyl-4-[(3R,4S)-3,4-dihydroxypyrrolidin-1-yl]phenyl]ethynyl-3-quinuclidinol;

(3R)-3-[2-benzyl-4-[cis-3-hydroxy-4-methoxypyrrolidin-1-yl]phenyl]ethynyl-3-quinuclidinol;

(3R)-3-[2-benzyl-4-[trans-3-hydroxy-4-methoxypyrrolidin-1-yl]phenyl]ethynyl-3-quinuclidinol;

3-[4-[2-benzyl-6-[(3R,4R)-3-hydroxy-4-methoxypyrrolidin-1-yl]-3-pyridyl]phenyl]-3-quinuclidinol;

(E)-3-[2-[2-benzyl-6-(2-pyrrolidinon-1-yl)pyridin-3-yloxy]-1-fluoroethynylidene]quinuclidine;

1-[2-benzyl-6-(3,3-ethylenedioxypyrrolidin-1-yl)]-3-pyridyl]ethynylcyclohexylamine;

1-[2-benzyl-6-(4-methoxypiperidino)-3-pyridyl]ethynylcyclohexylamine;

4-[2-benzyl-6-[(3R,4R)-3,4-dimethoxypyrrolidin-1-yl]-3pyridyl]ethynyl-exo-1-azaadamantan-4-ol; and 4-[2-benzyl-6-[(3R,4R)-3,4-dimethoxypyrrolidin-1-yl]-3-pyridyl]ethynyl-endo-1-azaadamantan-4-ol.

Also, the present invention is a pharmaceutical composition comprising a compound (I) represented by the formula:

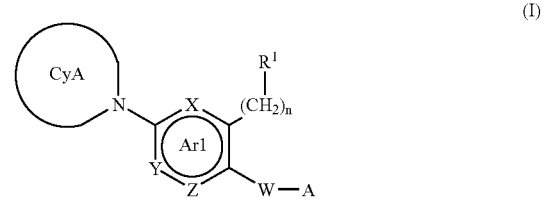

(I)

(wherein $R^1$ represents an optionally substituted vinyl group or an aromatic ring which may be substituted;

n is an integer of 0 to 2;

X, Y, and Z are the same as or different from each other and each represents an optionally substituted carbon atom, or an optionally substituted nitrogen atom, sulfur atom or oxygen atom, and Y may represent a single bond and when Y represents the single bond, the ring to which X, Y and Z belong is a 5-membered;

CyA represents a 5- to 14 membered non-aromatic cyclic amino group or non-aromatic cyclic amido group, each of which may be substituted, and the non-aromatic cyclic amino group or the non-aromatic cyclic amido group may contain an oxygen atom or a sulfur atom;

W represents a chain expressed by (1) optionally substituted —CH$_2$—CH$_2$—, (2) optionally substituted —CH=CH—, (3) —C≡C—, (4) an optionally substituted phenylene group, (5) a single bond, (6) —NH—CO—, (7) —CO—NH—, (8) —NH—CH$_2$—, (9) —CH$_2$—NH—,

(10) —CH$_2$—CO—,

(11) —CO—CH$_2$—,

(12) —O—(CH$_2$)$_m$—,

(13) —(CH$_2$)$_m$—O— (where m represents an integer of 0 to 5),

(14) —O—CH$_2$—CR$^2$=,

(15) —O—CH$_2$—CHR$^2$— (where $R^2$ represents a hydrogen atom, a $C_{1-6}$ alkyl group, or a halogen atom),

(16) —NH—S(O)$_l$—,

(17) —S(O)$_l$—NH—,

(18) —CH$_2$—S(O)$_l$— or

(19) —S(O)$_l$—CH$_2$— (where l represents 0, 1, or 2); and

A represents a group having any of the following structural formulae:

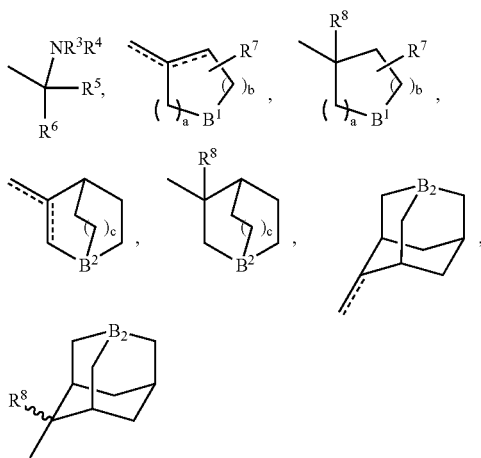

(wherein $R^3$ and $R^4$ are independent of each other and each represents a hydrogen atom or an optionally substituted $C_{1-6}$ alkyl group, or combine through a carbon chain optionally containing a heteroatom to form a ring;

$R^5$ and $R^6$ are independent of each other and each represents a hydrogen atom or an optionally substituted $C_{1-6}$ alkyl group, or combine through a carbon chain optionally containing a heteroatom to form a ring;

$R^7$ represents a hydrogen atom, an optionally substituted $C_{1-6}$ alkyl group, a hydroxyl group, an alkoxy group, a halogen atom or an optionally substituted amino group;

$R^8$ represents a hydrogen atom, a hydroxyl group, an alkoxy group, a halogen atom or an optionally substituted amino group, $B^1$ represents an optionally substituted carbon atom, or an optionally substituted nitrogen atom, oxygen atom or sulfur atom;

$B^2$ represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having $R^8$ represented by

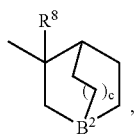

the case where $R^8$ is a hydrogen atom or a hydroxyl group; Arl is an aromatic heterocycle; and W is one of (1) to (3), (6) to (11) and (16) to (19) are excluded)), a salt thereof or a hydrate of them, and a preparation carrier.

The present invention is a pharmaceutical composition comprising the above-mentioned compound (I), a salt thereof or a hydrate of them, as an agent for preventing or treating a disease against which squalene synthase inhibition is efficacious.

The present invention is a cholesterol biosynthesis inhibitor comprising the above-mentioned compound (I), a salt thereof or a hydrate of them.

The present invention is a triglyceride biosynthesis inhibitor comprising the above-mentioned compound (I), a salt thereof or a hydrate of them.

The present invention is an agent for preventing or treating hyperlipidemia, which comprises the above-mentioned compound (I), a salt thereof or a hydrate of them.

The present invention is an agent for preventing or treating arterial sclerosis diseases or ischemic heart diseases, which comprises the above-mentioned compound (I), a salt thereof or a hydrate of them.

The present invention is an agent for preventing or treating hypertension, coronary diseases, cerebrovascular diseases, aortic diseases, peripheral arterial diseases, angina pectoris, acute coronary syndromes or cardiac infarction, which comprises the above-mentioned compound (I), a salt thereof or a hydrate of them.

The present invention provides a method of preventing or treating a disease against which squalene synthase inhibition is efficacious, by administering a pharmaceutically effective amount of the above-mentioned compound (I), a salt thereof or a hydrate of the to a patient.

Also, the present invention provides use of the above-mentioned compound (I), a salt thereof or a hydrate of the, for producing an agent for preventing or treating a disease against which squalene synthase inhibition is efficacious.

Further, the present invention provides a method of preventing or treating a disease against which cholesterol biosynthesis inhibition is efficacious, a disease against which triglyceride biosynthesis inhibition is efficacious, hyperlipidemia, arterial sclerosis diseases, ischemic heart diseases, hypertension, coronary diseases, cerebrovascular diseases, aortic diseases, peripheral arterial diseases, angina pectoris, acute coronary syndromes or cardiac infarction, by administering a pharmaceutically effective amount of the above-mentioned compound (I), a salt thereof or a hydrate of the to a patient.

Furthermore, the present invention provides use of the above-mentioned compound (I), a salt thereof or a hydrate of the, for producing an agent for preventing or treating a disease against which cholesterol biosynthesis inhibition is efficacious, a disease against which triglyceride biosynthesis inhibition is efficacious, hyperlipidemia, arterial sclerosis diseases, ischemic heart diseases, hypertension, coronary diseases, cerebrovascular diseases, aortic diseases, peripheral arterial diseases, angina pectoris, acute coronary syndromes or cardiac infarction.

In the specification of the present invention, there is the case where the structural formula of a compound represents a definite isomer. However, the present invention includes isomers such as geometrical isomers, optical isomers based on asymmetric carbon, stereoisomers and tautomers and is not limited by the description of the formula illustrated for the sake of convenience.

Hereinafter, the terms used in the present specification will be defined.

In the present specification, the group represented by $R^1$ in the general formula (I) means an optionally substituted vinyl group or an aromatic ring which may be substituted, preferably an aromatic ring which may be substituted. Here, the aromatic ring is not particularly limited and means, for example, a benzene ring, a thiophene ring, etc. On the other hand, the optionally substituted vinyl group means that one hydrogen atom or more in the vinyl group may be substituted by, for example, an optionally protected hydroxyl group, a halogen atom, a nitrile group, a carboxyl group, a $C_{1-6}$ alkyl group, or the like. A group "optionally substituted" means that the group may have one or more substituent(s) such as, for example, a hydroxyl group which may be protected, a halogen atom, a nitrile group, a carboxyl group, or a $C_{1-6}$ alkyl group.

Further, an "optionally substituted" group in the definitions of X, Y and Z means that the group may be substituted with, for example, a lower alkyl group, a halogen atom or a lower alkoxy group. CyA in the general formula (I) represents a 5- to 14-membered non-aromatic cyclic amino group which may be substituted; the aromatic cyclic amino group optionally contains an oxygen atom or a sulfur atom. For example, an azetidine ring, a pyrrolidine ring, a piperidine ring, a piperazine ring, a morpholine ring, etc. may be proposed, and a pyrrolidine ring is particularly preferred. A group "which may be substituted" in CyA includes, for example,
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group.

W represents a bonding chain whose main chain is constituted by two or more atoms, and preferably includes chains represented by, for example,
(1) optionally substituted —CH$_2$—CH$_2$—,
(2) optionally substituted —CH═CH—,
(3) —C≡C—,
(4) an optionally substituted phenylene group,
(5) a single bond,
(6) —NH—CO—,
(7) —CO—NH—,
(8) —NH—CH$_2$—,
(9) —CH$_2$—NH—,
(10) —CH$_2$—CO—,
(11) —CO—CH$_2$—,
(12) —O—(CH$_2$)$_m$—,
(13) —(CH$_2$)$_m$—O— (where m represents an integer of 0 to 5),
(14) —O—CH$_2$—CR$^2$═,
(15) —O—CH$_2$—CHR$^2$— (where R$^2$ represents a hydrogen atom, a $C_{1-6}$ alkyl group or a halogen atom),
(16) —NH—S(O)$_l$—,
(17) —S(O)$_l$—NH—,
(18) —CH$_2$—S(O)$_l$—, or
(19) —S(O)$_l$—CH$_2$— (where l represents 0, 1, or 2), more preferably,
(1) —CH$_2$—CH$_2$—,
(2) —CH═CH—, or
(3) —C≡C—, still more preferably, —C≡C—.

Here, "optionally substituted —CH$_2$—CH$_2$—" and "optionally substituted —CH═CH—" mean that one hydrogen atom or more in the —CH$_2$—CH$_2$— or —CH═CH— may be substituted by, for example, an optionally protected hydroxyl group, a halogen atom, a nitrile group, a carboxyl group or a $C_{1-6}$ alkyl group.

A represents:

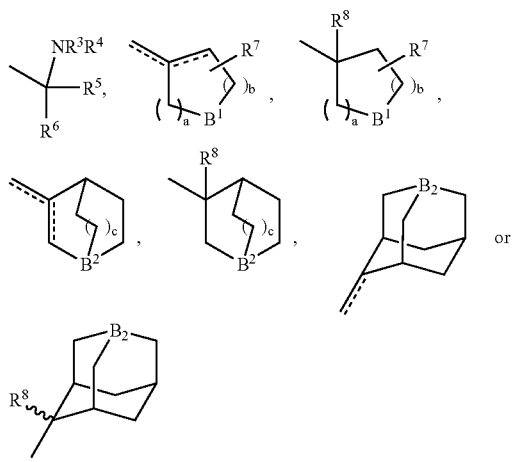

wherein, R$^3$ and R$^4$ are independent of each other and each represents a hydrogen atom or an optionally substituted $C_{1-6}$ alkyl group, or combine through a carbon chain optionally containing a heteroatom to form a ring; R$^5$ and R$^6$ are independent of each other and each represents a hydrogen atom, a halogen atom, a $C_{1-6}$ alkyl group, a hydroxyl group or an optionally substituted $C_{1-6}$ alkyl group, or combine through a carbon chain optionally containing a heteroatom to form a ring; R$^7$ represents a hydrogen atom, an optionally substituted $C_{1-6}$ alkyl group, a hydroxyl group, an alkoxy group, a halogen atom or an optionally substituted amino group; R$^8$ represents a hydrogen atom, a hydroxyl group, an alkoxy group, a halogen atom or an optionally substituted amino group; B$^1$ represents an optionally substituted carbon atom, or an optionally substituted nitrogen atom, oxygen atom or sulfur atom; B$^2$ represents an optionally substituted carbon atom or nitrogen atom; and ------- represents a single bond or a double bond.

In the definitions of R$^3$ to R$^8$, "optionally substituted $C_{1-6}$ alkyl group" means a $C_{1-6}$ alkyl group which may be substituted with a halogen atom, an optionally protected hydroxyl group or a $C_{1-6}$ alkoxy group, and "optionally substituted amino group", "optionally substituted carbon" or "optionally substituted nitrogen atom" mean an amino group, a carbon atom or a nitrogen atom, each of which may be substituted with a halogen atom, an optionally protected hydroxyl group, a $C_{1-6}$ alkoxy group or a $C_{1-6}$ alkyl group. Here, the protective group means an acetyl group or the like.

In the general formula (I), when

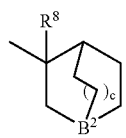

is a quinuclidine having R$^8$ and when c is 1, the cases where R$^8$ is a hydrogen atom or a hydroxyl group; Arl is an aromatic heterocycle; and W is one of (1) to (3), (6) to (11), and (16) to (19) are not included in the present invention.

In the present invention, the "$C_{1-6}$ alkyl chain" or "lower alkyl group" has the same meaning as "$C_{1-6}$ alkyl group", and means a linear or branched $C_{1-6}$ alkyl group such as a methyl group, an ethyl group, a n-propyl group, an i-propyl group, a sec-propyl group, a n-butyl group, an i-butyl group, a sec-butyl group, a t-butyl group, a n-pentyl group, an i-pentyl group, a sec-pentyl group, a t-pentyl group, a n-hexyl group, an i-hexyl group, a 1,2-dimethylpropyl group, a 2-ethylpropyl group, a 1-methyl-2-ethylpropyl group, a 1-ethyl-2-methylpropyl group, a 1,1,2-trimethylpropyl group, a 1,1,2-trimethylpropyl group, a 1,1-dimethylbutyl group, a 2,2-dimethylbutyl group, a 2-ethylbutyl group, a 1,3-dimethylbutyl group, a 2-methylpentyl group or a 3-methylpentyl group. Further, the lower alkoxy group has the same meaning as a $C_{1-6}$ alkoxy group and means a $C_{1-6}$ alkyloxy group such as a methoxy group, an ethoxy group, a n-propoxy group, an i-propoxy group, a sec-propoxy group, a n-butoxy group, an i-butoxy group, a sec-butoxy group, a t-butoxy group, a n-pentoxy group, an i-pentoxy group, a sec-pentoxy group, a t-pentoxy group, a n-hexoxy group, an i-hexoxy group, a 1,2-dimethyipropoxy group, a 2-ethylpropoxy group, a 1-methyl-2-ethylpropoxy group, a 1-ethyl-2-methylpropoxy group, a 1,1,2-trimethylpropoxy group, 1,1,2-trimethylpropoxy group, a 1,1-dimethylbutoxy group, a 2,2-dimethylbutoxy group, a 2-ethylbutoxy group, a 1,3-dimethylbutoxy group, a 2-methylpentoxy group or a 3-methylpentoxy group; a $C_{2-6}$ alkenyloxy group such as a vinyloxy group, an allyloxy group, an isopropoxyl group, a 1-propenyl-2-oxy group, a 1-butenyl-1-oxy group, a 1-butenyl-2-oxy group, a 1-butenyl-3-oxy group, a 2-butenyl-1-oxy group or a 2-butenyl-2-oxy group; and a $C_{2-6}$ alkynyloxy group such as an ethynyloxy group, a propynyloxy group, a butynyloxy group, a pentynyloxy group or a hexynyloxy group. Preferred "$C_{2-6}$ alkenyl group" is a linear or branched $C_{1-6}$ alkenyl group including a vinyl group, an allyl group, an isopropenyl group, a 1-propen-2-yl group, a 1-buten-1-yl group, a 1-buten-2-yl group, a 1-buten-3-yl group, a 2-buten-1-yl group and a 2-buten-2yl group. Examples of the "$C_{2-6}$ alkynyl group" include an ethynyl group, a propynyl group, a butynyl group, a pentynyl group and a hexynyl group.

The salts in the present invention means generally pharmacologically acceptable salts. Examples of these salts include hydrohalides such as hydrofluorides, hydrochlorides, hydrobromides and hydroiodides; inorganic acid salts such as sulfates, nitrates, perchlorates, phosphates, carbonates and bicarbonates; organic carboxylates such as acetates, maleates, tartrates and fumarates; organic sulfonates such as methanesulfonates, trifluoromethanesulfonates, ethanesulfonates, benzene sulfonates and toluene sulfonates; aminates such as alginates, aspartates and glutamates; salts with amines such as trimethylamine salts, triethylamine salts, procaine salts, pyridium salts and phenethylbenzylamine salts; alkali metal salts such as sodium salts and potassium salts; and alkali earth metal salts such as magnesium salts and calcium salts.

General Production Method

Various methods are considered as a method for producing the compound represented by the formula (I) according to the present invention and the compound can be produced by a usual organic synthetic method. To state a typical method, for example, the following method may be used to produce the compound.

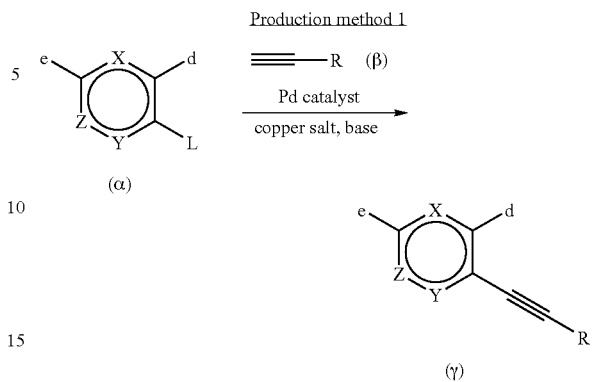

The above production method is a method of producing the compound (γ) according to the invention of the patent application of this case by coupling the aromatic heterocyclic compounds (α) and (β) with each other. In the formula, X, Y and Z are the same as or different form each other and each means (1) a carbon atom which may be substituted or (2) a heteroatom such as nitrogen atom, sulfur atom or oxygen atom, wherein there is the case where Y further means a single bond. When Y means a single bond, the ring to which X, Y and Z belong is a 5-membered ring. Here, in the case where X, Y and Z respectively represent the "carbon atom which may be substituted", the term "may be substituted" means that it may be substituted with the substituent shown in Ar1 in the formula (I) defined above. L means a leaving group and R means A in the general formula (I) or its precursor. As for the precursor of A, when A has, for example, an amino group, the precursor of A is a compound whose amino group is protected with an appropriate protective group (for example, a tert-butoxycarbonyl group, a benzyl group, a benzyloxycarbonyl group, a borane complex, or the like). The protective group is deprotected in the process of the reaction or in the final step by a treatment with a deprotecting agent or the like (for example, trifluoroacetic acid, hydrochloric acid, hydrochloric acid-acetone, catalytic hydrogenation with palladium carbon or the like, and so forth). The symbol d represents the —$(CH_2)_n$—$R^1$ in the general formula (I) or its precursor. The symbol e represents the non-aromatic cyclic amino group which may be substituted in the general formula (I) or its precursor. The leaving group L maybe any group generally so far as it is known as a leaving group useful in organic synthesis and is not particularly limited. For example, halogen atoms such as a chlorine atom, a bromine atom or an iodine atom; substituted or unsubstituted acetoxy groups such as an acetoxy group or a trifluoroacetoxy group; substituted sulfonyloxy groups such as a methanesulfonyloxy group, a trifluoromethanesulfonyloxy group, a benzenesulfonyloxy group or a p-toluenesulfonyloxy group; and substituted phosphoryloxy groups such as a diphenoxyphosphoryloxy group may be proposed. Preferably, a halogen atom such as a chlorine atom, a bromine atom or an iodine atom, a trifluoromethanesulfonyloxy group, or the like may be proposed. As the palladium catalyst, for example tetrakis(triphenylphosphine) palladium (0), bis(triphenylphosphine)palladium (II) chloride, or the like may be used in an amount of 0.0001 to 0.1 molar equivalent. As the copper salt, for example, cuprous iodide, cuprous chloride, or the like may be used in an amount of 0.0001 to 0.1 molar equivalent. As the base, for example, triethylamine, N,N-diisopropylethylamine, or the like may be used in an amount of 1 to 5 equivalents. It is preferred that reaction be performed by using N,N-dimethylformamide, N-methylpyrrolidone, tetrahydrofuran, methanol, or a mixed solvent thereof as a solvent at a reaction temperature of 0° C. to 140° C.

Subjecting the compound (γ) described above to reduction with a metal hydride complex compound such as lithium aluminum hydride or catalytic hydrogenation with a catalyst such as platinum oxide (IV) or palladium activated carbon can convert the triple bond of the compound γ to a double bond or can derive the compound γ to a saturated hydrocarbon. Also, hydration reaction by allowing mercury oxide (II) to act under acidic conditions or the like can derive the compound γ with a triple bond to a carbonyl compound.

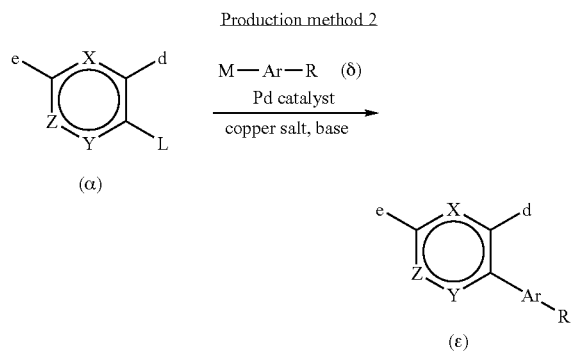

By the production method described above, the compound (ε) of the present invention can be produced. In the reaction scheme, X, Y, Z, d, e and L have the same meanings as defined above. L is, for example, a chlorine atom, a bromine atom, an iodine atom, or a trifluoromethanesulfonyloxy group. M means a metal atom which may be substituted, and preferred examples of M include tributyltin and dihydroxyboron. As the palladium catalyst, tetrakis(triphenylphosphine)palladium (0), bis(triphenylphosphine)palladium (II) chloride or the like can be used in an amount of 0.0001 to 0.1 molar equivalent. The solvent includes toluene, xylene, N,N-dimethylformamide and N-methylpyrrolidone. Reaction temperatures of from room temperature to 150° C. are used. When the metal M is boron, an inorganic base such as sodium carbonate or an organic base such as triethylamine is used as the base and an organic solvent containing water is also used as the solvent.

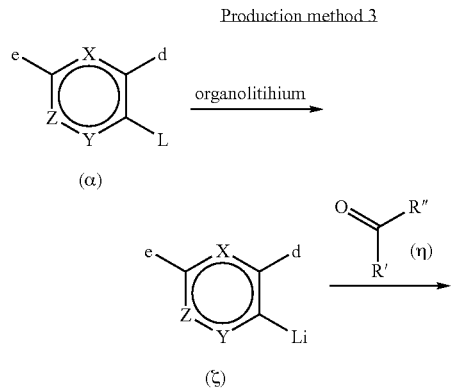

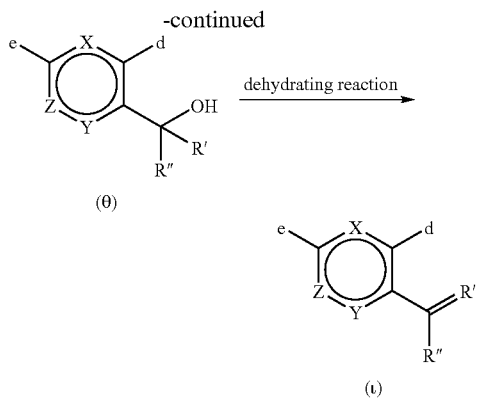

The production method described above is a method in which an organolithium compound and then a ketone derivative (η) is allowed to act on the aromatic compound (α) to produce compounds (θ) and (ι) of the present invention. In the reaction scheme, X, Y, Z, d and e have the same meanings as defined above. L means a halogen atom. R' and R" represent elements that constitute A in the general formula (I). The organolithium compound may be used in an amount of 1 to 20 equivalents. Used as the solvent are diethyl ether, tetrahydrofuran, dimethoxyethane, dioxane, hexane, benzene, etc. and mixed solvents thereof. The reaction temperature used is from −100° C. to room temperature. Allowing the ketone derivative (η) to act using the same solvent and reaction temperature as those for an organometal-halogen exchange reaction can produce the compound (θ). Also, subsequently performing an acid treatment or a dehydration reaction with a halogenating reagent, a sulfonating reagent, an esterifying reagent, a dehydrating reagent, or the like can produce the compound (ι).

Allowing carbon dioxide to act on the compound (α) after the organometal-halogen exchange reaction can synthesize an aromatic carboxylic acid, and allowing an amine derivative to the aromatic carboxylic acid by a conventional method can synthesize an acid amide compound. Also, the Curtius rearrangement reaction or the like can derive the obtained aromatic carboxylic acid to an aromatic amine derivative and allowing a carboxylic acid derivative to act by a conventional method can also synthesize an acid amide compound.

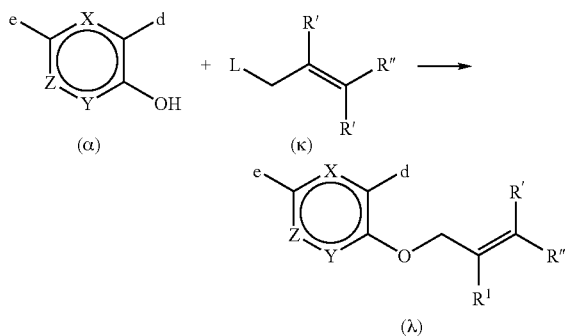

The production method described above is a method in which a compound (κ) is allowed to act on the aromatic compound (α) to produce a compound (λ) of the present invention. In the reaction scheme, X, Y, Z, e and d have the same meanings as defined above. L means a halogen atom. $R^1$, R' and R" represent elements that constitute W and A in the general formula (I). The compound (κ) can be derived from a carboxylic acid ester synthesized by a conventional method of the Wittig-Horner-Emmons reaction. The compound (λ) can be produced by allowing the compounds (α) and (κ) to act in the presence of a metal hydride such as sodium hydride, sodium alkoxide, lithium hydroxide, sodium hydroxide, potassium hydroxide, sodium carbonate, potassium carbonate, sodium hydrogen carbonate, or an organolithium compound under room temperature to heated conditions.

Next, the production method of the intermediate (α) that is involved in the production of the compounds of the present invention, divided into (α-A), (α-B), (α-C), (α-D) and (α-E), will be described hereinbelow.

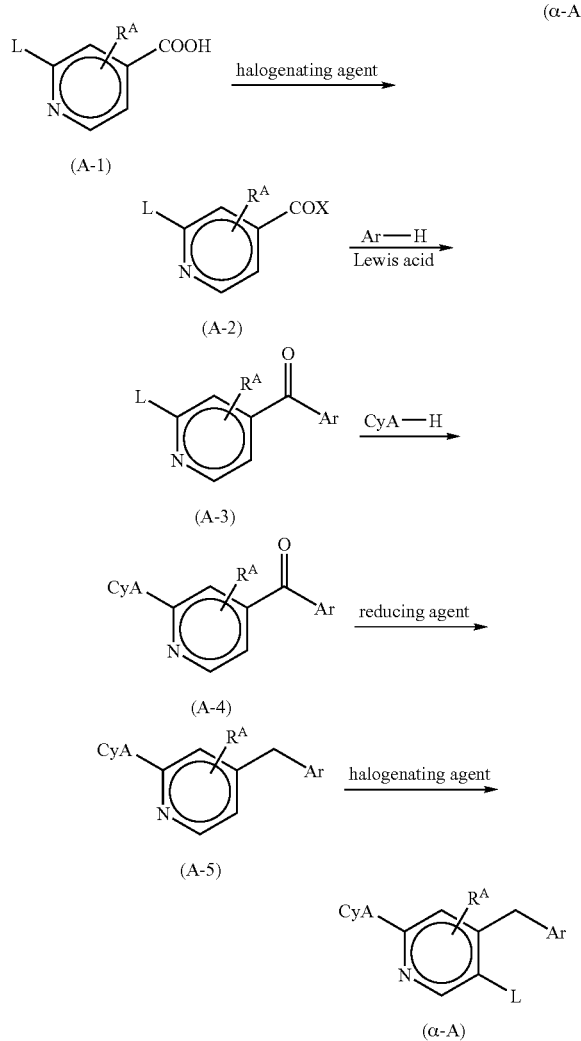

The production method described above is a method in which the intermediate (α-A) that is involved in the production of the compounds of the present invention is produced. In the formulae described above, $R^4$ represents a hydrogen atom, a lower alkyl group, a lower alkoxy group or a halogen atom; L represents a leaving group, for example, a halogen atom and the like; Ar represents an aromatic ring which may be substituted; and CyA represents a cyclic amino group which may be substituted or a cyclic amido group which may be substituted. Reacting an isonicotinic acid derivative (A-1) with 1 to 100 equivalents of a halogenating agent (for example, oxalyl chloride, thionyl chloride, or the like) in a solvent (for example, methylene chloride, chloroform, benzene, toluene, or the like) at 0° C. to 140° C. can provide (A-2). Subsequently, performing the Friedel-Crafts reaction using an excess amount of an aromatic hydrocarbon, for example, benzene, toluene, anisole, fluorobenzene, or the like at −50° C. to 140° C. with addition of a Lewis acid (for example, anhydrous aluminum chloride) can produce (A-3). Reacting (A-3) with 1 to 10 equivalents of a cyclic amine which may be substituted in the absence of a solvent or in the presence of 1 to 10 equivalents of a base (for example, 1,8-diazabicyclo[5.4.0]-7-undecene or the like) in a solvent, for example, 1-methylpyrrolidinone or the like at room temperature to 200° C. can synthesize (A-4). Also, reacting 0.1 to 10 equivalents of a copper compound (for example, copper powder, copper iodide, or the like) or the like with 1 to 10 equivalents of a base (for example, potassium carbonate or the like) and 1 to 10 equivalents of a cyclic amide which may be substituted in a solvent such as 1-methylpyrrolidinone can synthesize (A-4). Then, performing the Clemmensen reduction with using zinc amalgam prepared from 1 to 10 times amount of zinc white, 0.1 to 1 time amount of mercury chloride (II), 0.1 to 1 time amount of concentrated hydrochloric acid and 1 to 10 times amount of water, and 0 to 10 times amount of water, 1 to 100 times amount of concentrated hydrochloric acid, and 0 to 10 times amount of a solvent, for example, toluene, ethanol, dioxane, acetic acid or the like, at 0° C. to 140° C. can synthesize (A-5). Alternatively, the reduction reaction can be performed by adding 1 to 10 equivalents of hydrazine, 1 to 10 equivalents of a base (for example, sodium hydroxide, potassium hydroxide, sodium alkoxide, potassium tert-butoxide, or the like) to (A-4) in the absence of a solvent or in a solvent, for example, ethanol, ethylene glycol, diethylene glycol, triethylene glycol, or the like at room temperature to 250° C. Also, (A-5) can be synthesized by reducing the ketone into a hydroxyl group with 1 to 20 equivalents of a metal hydride (for example, lithium aluminum hydride, sodium borohydride, or the like) in a solvent, for example, ether, tetrahydrofuran, methanol, ethanol, or the like; acetylating the hydroxyl group as it is was or by addition of, for example 1 to 10 times amount of acetic anhydride and an excess amount of pyridine or halogenating the hydroxyl group with a halogenating agent (for example, oxalyl chloride, thionyl chloride, phosphorus oxychloride, or the like); and subsequent catalytic hydrogenation reaction with 0.1 to 1 equivalent of a catalyst (palladium carbon, palladium hydroxide-carbon, or the like) under hydrogen stream at atmospheric pressure to 100 atm in the absence of a solvent or in a solvent, for example, methanol, ethanol, ethyl acetate, tetrahydrofuran, toluene, or the like. Then, reacting (A-5) with 1 to 10 equivalents of N-bromosuccinimide, N-iodosuccinimide, or the like in a solvent (for example, N,N-dimethylformamide, N-methylpyrrolidinone or the like) at 0° C. to 100° C. can synthesize (α-A). Also, reacting (A-5) with 1 to 10 equivalents of bromine or iodine in a basic aqueous solution (for example, an aqueous sodium hydrogen carbonate solution, an aqueous potassium carbonate solution, or the like) at 0° C. to 100° C. can synthesize (α-A), or reacting (A-5) with 1 to 10 equivalents of bromine or iodine monochloride in acetic acid at 0° C. to 150° C. can synthesize (α-A).

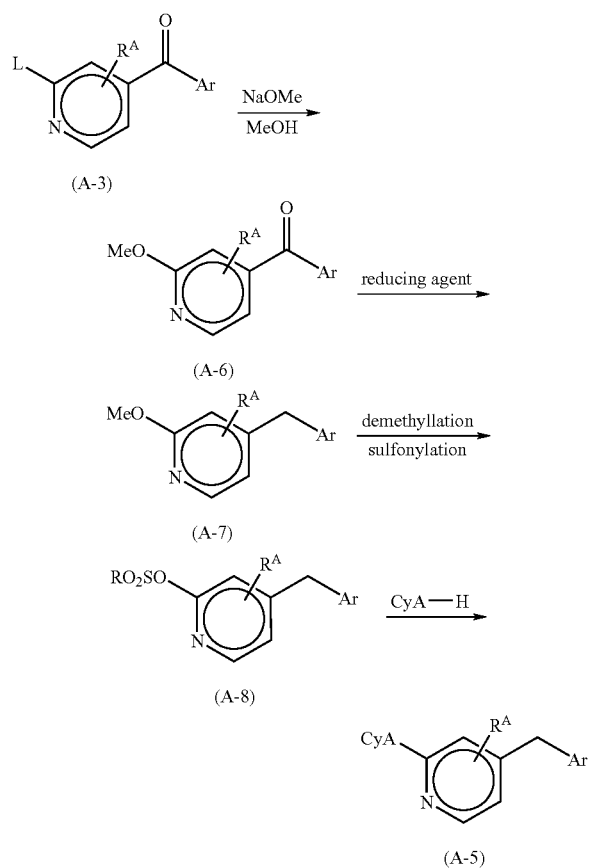

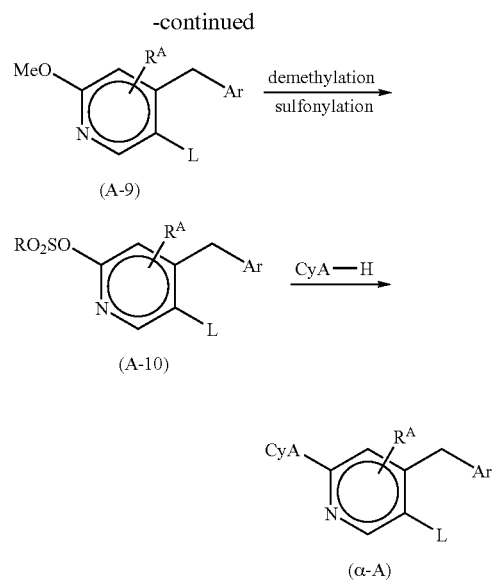

Alternatively, (A-5) can be synthesized from (A-3) by the following production method. Allowing 1 to 100 equivalents of sodium methoxide to act on (A-3) in methanol at room temperature to 150° C. can synthesize (A-6), and then (A-7) can be synthesized therefrom in the same manner as the reaction of from (A-4) to (A-5). Then, heating (A-7) under reflux at 50 to 150° C. in an excess amount of hydrobromic acid can demethylate it and reacting the resultant with 1 to 10 equivalents of a sulfonylating agent (for example, methanesulfonyl chloride, toluenesulfonyl chloride, anhydrous trifluoromethanesulfonyl, N-phenyltrifluoromethanesulfonimide, or the like) in the presence of 1 to 10 equivalents of a base (for example, pyridine, triethylamine, 4-dimethylaminopyridine, or the like) in a solvent, for example, methylene chloride, tetrahydrofuran, ethyl acetate, toluene or the like at 0° C. to 100° C. can synthesize (A-8). Then, (A-5) can also be synthesized by reacting (A-8) with 1 to 10 equivalents of a cyclic amine which may be substituted in the absence of a solvent or in the presence of 1 to 10 equivalents of abase (for example, 1,8-diazabicyclo[5.4.0]-7-undecene) in a solvent, for example, 1-methylpyrrolidinone or the like at room temperature to 200° C.

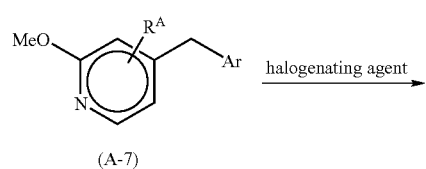

Further, reacting (A-7) 1 to 10 equivalents of bromine or iodine in the absence of a solvent, or in a solvent, for example methanol, ethylene glycol, or the like in the presence of a base (for example, an aqueous sodium hydrogen carbonate solution, an aqueous potassium carbonate solution, or the like) at 0° C. to 100° C. can synthesize (A-9) Then, heating (A-9) under reflux at 50 to 150° C. in an excess amount of hydrobromic acid can demethylate it and reacting the resultant with 1 to 10 equivalents of a sulfonylating agent (for example, methanesulfonyl chloride, toluenesulfonyl chloride, anhydrous trifluoromethanesulfonyl, N-phenyltrifluoromethanesulfonimide or the like) in the presence of 1 to 10 equivalents of abase (for example, pyridine, triethylamine, 4-dimethylaminopyridine, or the like) in a solvent, for example, methylene chloride, tetrahydrofuran, ethyl acetate, toluene or the like at 0° C. to 100° C. can synthesize (A-10). Then, (α-A) can also be synthesized by reacting (A-10) with 1 to 10 equivalents of a cyclic amine which may be substituted in the absence of a solvent or in the presence of 1 to 10 equivalents of abase (for example, 1,8-diazabicyclo[5.4.0]-7-undecene) in a solvent, for example, 1-methylpyrrolidinone, or the like at room temperature to 200° C.

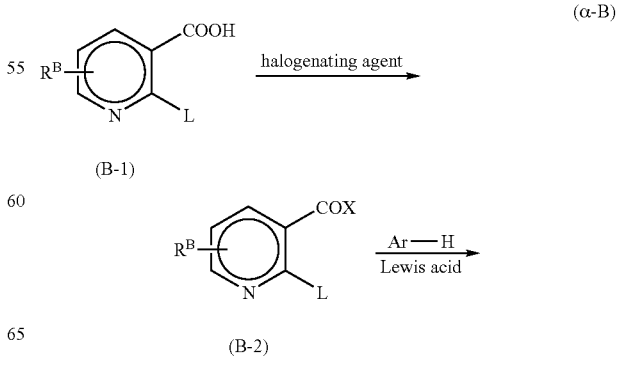

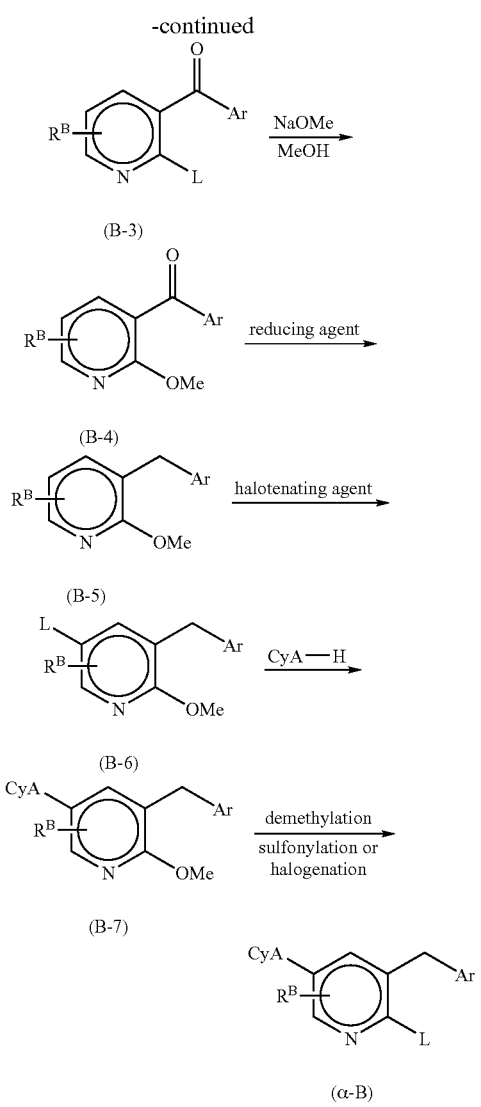

(B-3)

(B-4)

(B-5)

(B-6)

(B-7)

(α-B)

The production method described above is a method in which the intermediate (α-B) that is involved in the production of the compounds of the present invention is produced. In the formulae described above, L represents a leaving group, for example, a halogen atom, or the like; $R^B$ represents a hydrogen atom, a lower alkyl group, a lower alkoxy group or a halogen atom; Ar represents an aromatic ring which may be substituted; and CyA represents a cyclic amino group which may be substituted or a cyclic amido group which may be substituted. By reacting a nicotinic acid derivative (B-1) with 1 to 100 equivalents of a halogenating agent (for example, oxalyl chloride, thionyl chloride, or the like) in a solvent (for example, methylene chloride, chloroform, benzene, toluene, or the like) at 0° C. to 140° C., (B-2) can be obtained. Subsequent addition of a Lewis acid (for example, anhydrous aluminum chloride) and performing the Friedel-Crafts reaction using an excess amount of an aromatic hydrocarbon, for example, benzene, toluene, anisole, fluorobenzene, or the like at −50° C. to 140° C. can produce (B-3) Allowing 1 to 100 equivalents of sodium methoxide to act on (B-3) at room temperature to 150° C. can synthesize (B-4). Then, performing the Clemmensen reduction with using zinc amalgam prepared from 1 to 10 times amount of zinc white, 0.1 to 1 time amount of mercury chloride (II), 0.1 to 1 time amount of concentrated hydrochloric acid, and 1 to 10 times amount of water, and 0 to 10 times amount of water, 1 to 100 times amount of concentrated hydrochloric acid, and 0 to 10 times amount of a solvent, for example, toluene, ethanol, dioxane, acetic acid, or the like, at 0° C. to 140° C. can synthesize (B-5). Alternatively, a reduction reaction of (B-4) can be performed by adding 1 to 10 equivalents of hydrazine, 1 to 10 equivalents of a base (for example, sodium hydroxide, potassium hydroxide, sodium alkoxide, potassium tert-butoxide, or the like) to (B-4) in the absence of solvents or in a solvent, for example, ethanol, ethylene glycol, diethylene glycol, triethylene glycol, or the like at room temperature to 250° C. to synthesize (B-5). Also, (B-4) can be reduced by reducing the ketone into a hydroxyl group with 1 to 20 equivalents of a metal hydride (for example, lithium aluminum hydride, sodium borohydride, or the like) in a solvent, for example, ether, tetrahydrofuran, methanol, ethanol, or the like; acetylating the hydroxyl group as it is or by addition of, for example 1 to 10 times amount of acetic acid anhydride and an excess amount of pyridine or halogenating the hydroxyl group with a halogenating agent (for example, oxalyl chloride, thionyl chloride, phosphorus oxychloride or the like); and subsequent catalytic hydrogenation reaction with 0.1 to 1 equivalent of a catalyst (palladium-carbon, palladium hydroxide-carbon, or the like) under hydrogen stream at atmospheric pressure to 100 atm in the absence of solvents or in a solvent, for example, methanol, ethanol, ethyl acetate, tetrahydrofuran, toluene or the like. Then, reacting (B-5) with, for example, 1 to 10 equivalents of bromine or iodine in the absence of solvents or in a solvent, for example, methanol, ethylene glycol or the like in the presence of a base (for example, an aqueous sodium hydrogen carbonate solution, an aqueous potassium carbonate solution, or the like) at 0° C. to 100° C. can synthesize (B-6). Then, reacting (B-6) with 1 to 10 equivalents of a cyclic amine which may be substituted in the presence of 0.001 to 1 equivalent of 0-valent to divalent palladium (palladium acetate, tris(dibenzylideneacetone)dipalladium, or the like) and 0.001 to 1 equivalent of phosphorus ligand (tri-o-tolylphosphine, tri-tert-butylphosphine, 2,2'-bis(diphenylphosphino)-1,1'-binaphthyl, or the like), 1 to 10 equivalents of abase (for example, potassium tert-butoxide, potassium phosphate, cesium carbonate, or the like) in a solvent such as toluene or dioxane at 0° C. to 200° C. can synthesize (B-7). (B-7) can also be synthesized by allowing 1 to 10 equivalents of a cyclic amide which maybe substituted and 1 to 10 equivalents of a base (for example, potassium carbonate, or the like) to act on (B-6) with using 0.1 to 10 equivalents of a copper compound (for example, copper powder, copper iodide, or the like), or the like in a solvent such as 1-methylpyrrolidinone. Then, heating (B-7) under reflux at 50 to 150° C. in an excess amount of hydrobromic acid can demethylate it and reacting the resultant with 1 to 10 equivalents of a sulfonylating agent (for example, methanesulfonyl chloride, toluenesulfonyl chloride, anhydrous trifluoromethanesulfonyl, N-phenyltrifluoromethanesulfonimide, or the like) in the presence of 1 to 10 equivalents of abase (for example, pyridine, triethylamine, 4-dimethylaminopyridine or the like) in a solvent, for example, methylene chloride, tetrahydrofuran, ethyl acetate, toluene or the like at 0° C. to 100° C. can synthesize (α-B). Also, (α-B) can be synthesized by heating the demethylated product under reflux with a halogenating agent (for example, phosphorus oxychloride, phosphorus pentoxide, thionyl chloride, phosphorus oxybromide, or the like) in the absence of solvents or in a solvent such as a halogen solvent (for example, chloroform, dichloroethane, or the like), an aromatic solvent (for example, benzene, toluene, chlorobenzene, or the like), or N,N-dimethylformamide at 50° C. to 150° C.

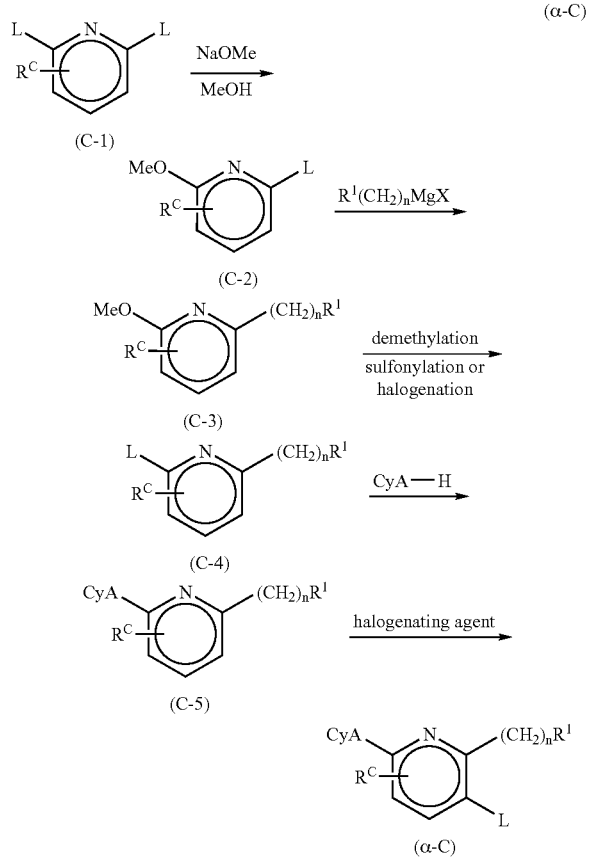

The production method described above is a method in which the intermediate (α-C) that is involved in the production of the compounds of the present invention is produced. In the formulae described above, $R^1$ and n are the same as those in the general formula (I); L represents a leaving group, for example, a halogen atom or the like; $R^C$ represents a hydrogen atom, a lower alkyl group, a lower alkoxy group or a halogen atom; and CyA represents a cyclic amino group which may be substituted or a cyclic amido group which may be substituted. Allowing 1 to 100 equivalents of sodium methoxide to act on a pyridine derivative (C-1) in methanol at room temperature to 150° C. can synthesize (C-2). By reacting (C-2) with a commercially available Grignard reagent or the Grignard reagent obtained by using a solvent such as ether or tetrahydrofuran and reacting $R^1(CH_2)_nX$ with an equivalent of magnesium at 0° C. to 100° C. in the presence of 0.001 to 1 equivalent of a nickel compound (for example, (1,3-bis(triphenylphosphino)propane)nickel (0) chloride, or the like) in a solvent such as ether or tetrahydrofuran at −50° C. to 100° C., (C-3) can be obtained. Then, (C-3) can be treated in an excess amount of hydrobromic acid at 50° C. to 150° C. to demethylate it. Reacting the resultant with 1 to 10 equivalents of a sulfonylating agent (for example, methanesulfonyl chloride, toluenesulfonyl chloride, anhydrous trifluoromethanesulfonyl, N-phenyltrifluoromethanesulfonimide, or the like) in the presence of 1 to 10 equivalents of a base (for example, pyridine, triethylamine, 4-dimethylaminopyridine, or the like) in a solvent, for example, methylene chloride, tetrahydrofuran, ethyl acetate, toluene, or the like at 0° C. to 100° C. can synthesize (C-4). Reacting (C-4) with 1 to 10 equivalents of a cyclic amine which may be substituted in the absence of solvents or in the presence of 1 to 10 equivalents of a base (for example, 1,8-diazabicyclo [5.4.0]-undecene or the like) in a solvent, for example, 1-methylpyrrolidinone or the like at room temperature to 200° C. can synthesize (C-5). Also, allowing 1 to 10 equivalents of a base (for example, potassium carbonate or the like) and 1 to 10 equivalents of a cyclic amide which may be substituted to act on (C-4) with using 0.1 to 10 equivalents of a copper compound (for example, copper powder, copper iodide, or the like) in a solvent such as 1-methylpyrrolidinone can also synthesize (C-5). Reacting (C-5) with 1 to 10 equivalents of N-bromosuccinimide, N-iodosuccinimide or the like in a solvent (for example, N,N-dimethylformamide, N-methylpyrrolidinone, or the like) at 0° C. to 100° C. can synthesize (α-C). Also, reacting (C-5) with 1 to 10 equivalents of bromine or iodine in a basic aqueous solution (for example, an aqueous sodium hydrogen carbonate solution, an aqueous potassium carbonate solution, or the like) at 0° C. to 100° C. can synthesize (α-C), or reacting (C-5) with 1 to 10 equivalents of bromine or iodine monochloride in acetic acid at 0° C. to 150° C. can synthesize (α-C).

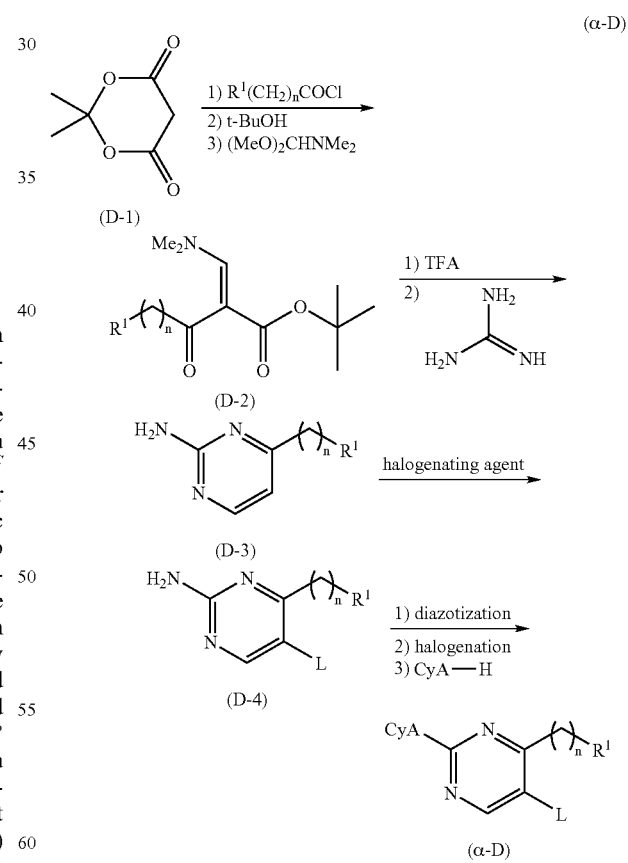

The production method described above is a method in which the intermediate (α-D) that is involved in the production of the compounds of the present invention is produced. In the formulae described above, $R^1$ and n are the same as those in the general formula (I); L represents a leaving group, for example, a halogen atom or the like; and CyA represents a cyclic amino group which may be substituted or a cyclic amido group which maybe substituted. Allowing 1 to 10 equivalents of $R^1(CH_2)_nCOCl$ to act on Meldrum's acid (D-1)in the presence of a base such as pyridine in a solvent such as dichloromethane at −50° C. to 100° C. and then allowing an excess amount of tert-butanol to act thereon at 50° C. to 150° C, and subsequently allowing N,N-dimethylformamide dimethyl acetal to act thereon in a solvent such as toluene at −50° C. to 100° C. can synthesize (D-2). Allowing 1 to 100 equivalents of trifluoroacetic acid to act on (D-2) in a solvent such as dichloromethane at −50° C. to 100° C., then allowing 1 to 10 equivalents of quanidine to act thereon in the presence of 1 to 10 equivalents of a base (for example, sodium ethoxide or the like) in an ethanol solvent or the like at 50° C. to 150° C. can synthesize (D-3). Allowing 1 to 10 equivalents of a halogenating agent (for example, bromine, N-bromosuccinic acid or the like) to act on (D-3) in the presence of 0 to 10 equivalents of a base (for example, sodium hydrogen carbonate or the like) in a solvent such as N,N-dimethylformamide or methanol at −50° C. to 100° C. can give rise to (D-4). Reacting (D-4) with 1 to 10 equivalents of a diazotizing agent such as isoamyl nitrite, an excess amount of a halogen solvent (for example, diiodomethane or the like), a halogenating agent (for example, cuprous iodide, cupric chloride, or the like), and a solvent such as tetrahydrofuran at 0° C. to 100° C. to halogenate the amino group, and then reacting the resultant with 1 to 10 equivalents of a cyclic amine which may be substituted in the absence of solvents or in the presence of 1 to 10 equivalents of a base (for example, 1,8-diazabicyclo[5.4.0]-undecene or the like) in a solvent, for example, 1-methylpyrrolidinone or the like at room temperature to 200° C. can synthesize (α-D). Also, allowing 1 to 10 equivalents of a base (for example, potassium carbonate or the like) and 1 to 10 equivalents of a cyclic amide which may be substituted to act on (D-4) with using 0.1 to 10 equivalents of a copper compound (for example, copper powder, copper iodide or the like) in a solvent such as 1-methylpyrrolidinone can also synthesize (α-D).

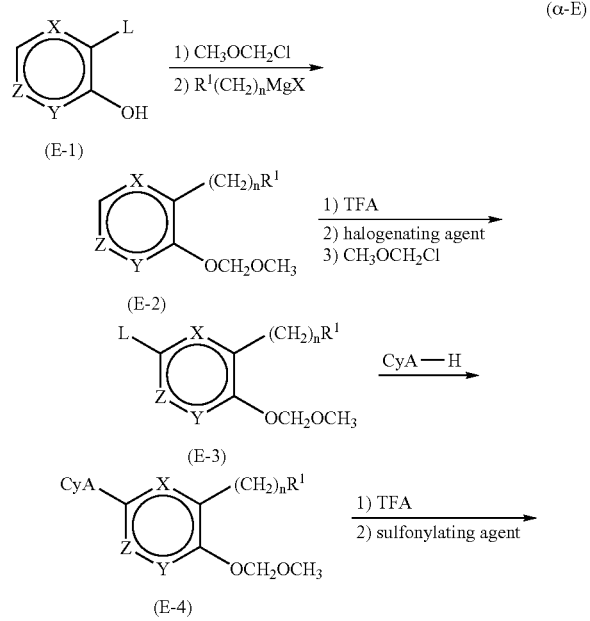

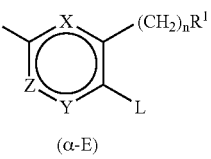

The production method described above is a method in which the intermediate (α-E) that is involved in the production of the compounds of the present invention is produced. In the formulae described above, $R^1$, n, X, Y, and Z are the same as those in the general formula (I); L represents a leaving group, for example, a halogen atom or the like; and CyA represents a cyclic amino group which may be substituted or a cyclic amido group which may be substituted. Allowing 1 to 10 equivalents of chloromethyl methyl ether to act on (E-1) in the presence of a base(for example, sodium hydride, potassium hydroxide, cesium carbonate, or the like) in a solvent (for example, tetrahydrofuran, diethyl ether, dioxane, or the like) to methoxymethylate it, and then allowing 1 to 10 equivalents of Grignard reagent (for example benzylmagnesium bromide or the like) to act on the resultant in the presence of 0.001 to 1 equivalent of a nickel compound (for example, 1,3-bis(diphenylphosphino)propane nickel (0) chloride or the like) in a solvent such as diethyl ether or tetrahydrofuran at −50° C. to 100° C. can synthesize (E-2). Allowing 1 to 100 equivalents of an acid (for example, trifluoroacetic acid or the like) to act on (E-2), then allowing a halogenating agent (for example, sodium iodide and sodium hypochlorite, N-bromosuccinimide or the like) and 0 to 10 equivalents of a base (for example, sodium hydroxide or the like) to act on the resultant in a solvent such as methanol or ethanol, and subsequently allowing 1 to 10 equivalents of chloromethyl methyl ether to act thereon in the presence of 1 to 10 equivalents of abase (for example, sodium hydride, potassium hydroxide, cesium carbonate or the like) in a solvent (for example, tetrahydrofuran, diethyl ether, dioxane or the like) can synthesize (E-3). Performing reaction of (E-3) in the presence of 0.001 to 1 equivalent of 0-valent to divalent palladium (palladium acetate, tris(dibenzylideneacetone)dipalladium or the like) and 0.001 to 1 equivalent of phosphorus ligand (tri-o-tolylphosphine, tri-tert-butylphosphine, 2,2'-bis(diphenylphosphino)-1,1'-binaphthyl or the like), and 1 to 10 equivalents of a base (for example, potassium tert-butoxide, potassium phosphate, cesium carbonate or the like) in a solvent such as toluene or dioxane at 0° C. to 200° C. can produce (E-4). (E-4) can also be synthesized by allowing 1 to 10 equivalents of a cyclic amide which may be substituted and 1 to 10 equivalents of a base (for example, potassium carbonate or the like) to act on (E-3) with using 0.1 to 10 equivalents of a copper compound (for example, copper powder, copper iodide or the like) or the like in a solvent such as 1-methylpyrrolidinone. Then, treating (E-4) with an excess amount of an acid (for example, trifluoroacetic acid) to deprotect methoxymethyl group and reacting the resultant with 1 to 10 equivalents of a sulfonylating agent (for example, methanesulfonyl chloride, toluenesulfonyl chloride, anhydrous trifluoromethanesulfonyl, N-phenyltrifluoromethanesulfonimide or the like) in the presence of 1 to 10 equivalents of abase (for example, pyridine, triethylamine, 4-dimethylaminopyridine or the like) in a solvent, for example, methylene chloride, tetrahydrofuran, ethyl acetate, toluene or the like at 0° C. to 100° C. can synthesize (α-E). Also, (α-E) can be produced by heating the deprotected product under reflux with a halogenating agent (for example, phosphorus oxychloride, phosphorus pentoxide, thionyl chloride, phosphorus oxybromide or the like) in the absence of solvents or in a solvent such as a halogen solvent (for example, chloroform, dichloroethane or the like), an aromatic solvent (for example, benzene, toluene, chlorobenzene or the like), or N,N-dimethylformamide at 50° C. to 150° C.

Next, the production method for the intermediate (δ) that is involved in the production of the compounds of the present invention will be described hereinbelow.

M-Ar—R (δ)

Note that the primary or secondary amino group contained in the intermediate (δ) maybe protected with a stable protective group (for example, a tert-butoxycarbonyl group, a benzyl group, a benzyloxycarbonyl group or the like) during the production process, or the tertiary amino group contained in the intermediate (δ) may be protected as a borane complex. Further, in case where the protective group is deprotected in the production process, there maybe a case where a protective group is introduced again.

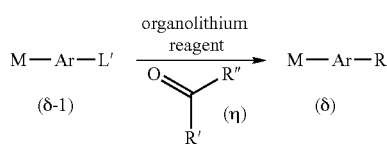

By the production method described above, the compound (δ) of the present invention can be produced. Ar, R, R', and R" represent elements that constitute W and A in the general formula (I). Further, M represents a substituent having a metal and L' represents a halogen atom. In (δ-1), M represents, for example, tributyltin, boric acid esterified with N-methyldiethanolamine, or the like. (δ) can be synthesized by allowing 1 to 10 equivalents, preferably 1 to 3 equivalents of an organolithium reagent (for example, n-butyllithium, sec-butyllithium, tert-butyllithium or the like) to act on (δ-1) at −100° C. to 0° C. in a solvent (for example, diethyl ether, tetrahydrofuran, or the like) and subsequently allowing (η) to act on the resultant at −100° C. to room temperature.

Then, the production method for the intermediate (κ) that is involved in the production of the compound of the present invention will be described hereinbelow.

Note that the primary or secondary amino group contained in the intermediate (κ) maybe protected with a stable protective group (for example, a tert-butoxycarbonyl group, a benzyl group, a benzyloxycarbonyl group or the like) during the production process, or the tertiary amino group may be protected as a borane complex. Further, in case the protective group is deprotected in the production process, there maybe a case where a protective group is introduced again. Further, the intermediate (κ) can also be synthesized by the method described in WO 96/26938.

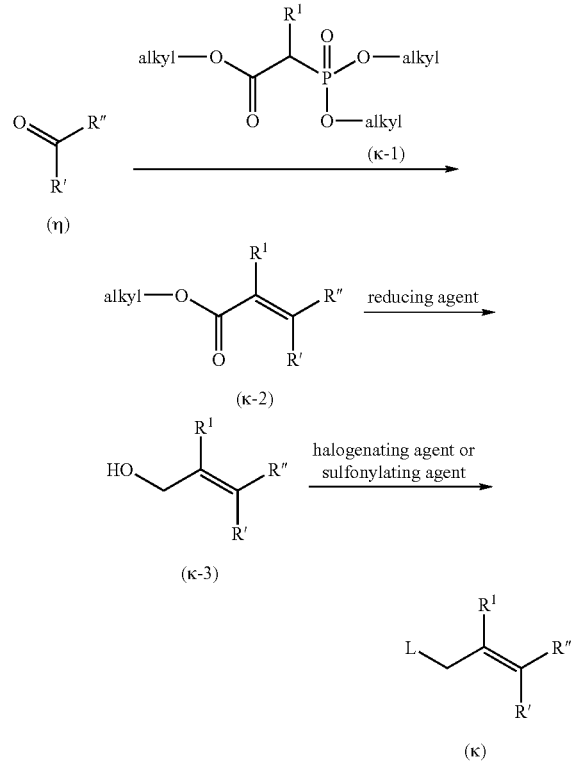

By the production method described above, the compound (κ) of the present invention can be produced. $R^1$, R', and R" represent elements that constitute W and A in the general formula (I). Reacting (η) with 1 to 10 equivalents, preferably 1 to 3 equivalents of Wittig-Horner-Emmons reagent (κ-1) in a solvent (for example, methanol, ethanol, tetrahydrofuran, dioxane, diethyl ether, toluene, benzene or the like) in the presence of 1 to 2 equivalents of a base (for example, sodium hydride, sodium methoxide, sodium hydroxide, n-butyllithium or the like) with respect to (κ-1) at −50° C. to 100° C. can synthesize (κ-2). There are geometric isomers of (κ-2). The isomers can be isolated by subjecting (κ-2) or (κ-3) to silica gel column chromatography or the like. (κ-2) can be converted to (κ-3) by performing a reduction reaction of (κ-2) in a solvent (for example, tetrahydrofuran, diethyl ether, toluene or the like) in the presence of a stoichiometric amount of or an excess amount of a reducing agent (for example, diisobutylaluminum hydride, lithium aluminum hydride, or the like) at −100° C. to 50° C. Subsequently, (κ-3) can be converted into (κ) by allowing 1 to 10 equivalents of a sulfonylating agent (for example, methanesulfonyl chloride, toluenesulfonyl chloride or the like) to act on (κ-3) in a solvent (for example, dichloromethane, N,N-dimethylformamide, tetrahydrofuran or the like) in the presence of 1 to 10 equivalents of abase (for example, pyridine, triethylamine or the like) at 0° C. to 50° C. Further, 1 to 10 equivalents of lithium chloride may be added to the reaction mixture. Also, (κ) can be synthesized by allowing 1 to 10 equivalents of a halogenating agent (for example, phosphorus tribromide, phosphorus trichloride or the like) and 0 to 10 equivalents of a base (for example, pyridine, quinoline or the like) to act on (κ-3); allowing 1 to 10 equivalents of triphenyl phosphonate and 1 to 10 equivalents of an alkyl halide (for example, benzyl chloride or the like) to act on (κ-3); or allowing 1 to 10 equivalents of triphenylphosphine and an excess amount of carbon tetrahalide (for example, carbon tetrachloride) to act on (κ-3) in a solvent (for example, dichloromethane, N,N-dimethylformamide, tetrahydrofuran, toluene or the like) Next, the production method of the intermediate (β) that is involved in the production of the compounds of the present invention, divided into (β-A), (β-B) and (β-C), will be described hereinbelow.

Note that the primary or secondary amino group contained in the intermediate (β) may be protected with a stable protective group (for example, a tert-butoxycarbonyl group, a benzyl group, a benzyloxycarbonyl group or the like) during the production process, or the tertiary amino group contained in the intermediate (β) maybe protected as a borane complex. Further, in case where the protective group is deprotected in the production process, there maybe a case where a protective group is introduced again.

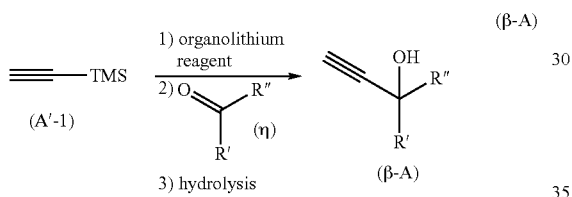

By the production method described above, the compound (β-A) of the present invention can be produced. In the reaction scheme, R' and R" represent elements that constitute A in the general formula (I). Dissolving 1 to 10 equivalents, preferably 1 to 3 equivalents based on (η) of trimethylsilylacetylene in a solvent (for example, hexane, benzene, toluene, tetrahydrofuran, diethyl ether, or the like), allowing 0.1 to 10 equivalents, preferably 0.5 to 2 equivalents based on trimethylsilylacetylene of an organolithium reagent (for example, n-butyllithium or the like) to act on the trimethylsilylacetylene at −100° C. to room temperature, preferably −80° C. to 0° C., and subsequently allowing a ketone derivative (η) to act on the resultant, followed by performing hydrolysis with 1 to 10 equivalents of a base (potassium carbonate, sodium hydroxide, or the like) in the absence of a solvent or in the presence of a solvent (methanol, ethanol, dimethylformamide, tetrahydrofuran, water, or the like) can synthesize (β-A).

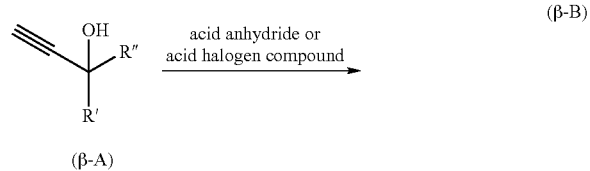

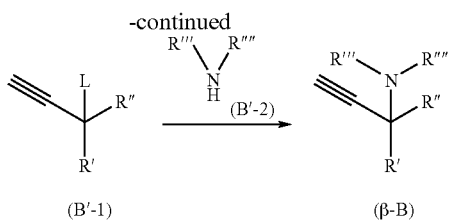

By the production method described above, the compound (β-B) of the present invention can be produced. In the reaction scheme, L means a leaving group, and R', R", R'" and R"" represent elements that constitute A in the general formula (I). Adding a solvent (for example, benzene, toluene, chloroform, dichloromethane, or the like) to (β-A), adding 1 to 100 equivalents of an acid anhydride or a acid halogen compound (for example, acetic anhydride or the like) at −50° C. to 100° C., preferably −20° C. to room temperature, and then adding 0.01 to 10 equivalents of a Lewis acid (for example, trimethylsilyl triflate) can synthesize (B'-1). Adding a solvent (for example, benzene, toluene, tetrahydrofuran, chloroform, dichloromethane, or the like) to (B'-1) and allowing 1 to 100 equivalents of an amine derivative (B'-2) and 0.01 to 10 equivalents of a copper compound (for example, cuprous chloride or the like) to act on (B'-1) can produce (β-B).

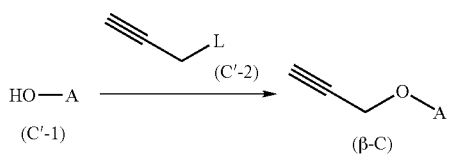

By the production method described above, the compound (β-C) of the present invention can be produced. In the reaction scheme, L represents a leaving group (for example, a halogen atom or the like) and A represents elements that constitutes the general formula (I). Dissolving (C'-1) in a solvent (for example, N,N-dimethylformamide, tetrahydrofuran or the like), reacting the resultant with 0.5 to 10 equivalents of an alkali metal reagent (for example, sodium, sodium hydride, potassium hydride or the like) at −50° C. to room temperature and subsequently adding 1 to 10 equivalents of (C'-2) at −100° C. to room temperature, followed by elevating the reaction temperature from room temperature to 100° C., whereby can synthesize (β-C).

No particular limitation is imposed on the dosage form of the compound according to the present invention and either oral administration or parenteral administration according to a method which is usually used is acceptable. The compound may be made into preparations of a tablet, powder, granule, capsule agent, syrup agent, troche, inhalant, suppository, injection, ointment, ophthalmic ointment, ophthalmic solution, collunarium, ear drop, cataplasm and lotion, and administered. In the preparation of these forms, fillers, binders, lubricants, colorants, flavoring agents, and if necessary, stabilizers, emulsifiers, absorbefacient agents, surfactants, pH regulators, antiseptics and antioxidants etc. may be used and components which are usually used as raw materials of medicinal preparations are formulated to prepare a medicine by a usual method. Examples of these components include animal or vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicon resins; silicon oils; surfactants such as polyoxyethylene fatty acid ester, sorbitan fatty acid ester, glycerol fatty acid ester, polyoxyethylenesorbitan fatty acid ester, polyoxyethylene hydrogenated castor oil and polyoxyethylene/polyoxypropylene block copolymers; water-soluble polymers such as hydroxyethyl cellulose, polyacrylic acid, carboxyvinyl polymers, polyethylene glycol, polyvinylpyrrolidone and methyl cellulose; lower alcohols such as ethanol and isopropanol;polyhydric alcohols such as glycerol, propylene glycol, dipropylene glycol and sorbitol; sugars such as glucose and cane sugar; inorganic powders such as silicic acid anhydride, aluminum magnesium silicate and aluminum silicate; and purified water.

The medicine according to the present invention is administered to an adult patient at a dose of generally about 30 μg to 10 g, preferably 100 μg to 5 g and more preferably 100 μg to 100 mg in the case of oral administration and about 30 μg to 1 g, preferably 100 μg to 500 mg and more preferably 100 μg to 30 mg in the case of injection in one to several parts a day although the dose differs depending on the degree of a symptom, age, sex, weight, dosage form and type of disease.

The biochemical activities of the compound according to the present invention and the effects (squalene synthase activity and cholesterol biosynthesis inhibitive activity) of the compound as a medicine may be evaluated by the following methods.

Test Example 1

Measurement of Squalene Synthase Inhibitive Activity by Using a Rat Liver Microsome (I) The reaction was run on a scale of 500 μl. 200 μl of a solution containing 125 mM tris-hydrochloric acid (pH: 7.3), 2.5 mM magnesium chloride, 5 mM potassium fluoride and 10 mM reduction type nicotinamidoadenine dinucleotide phosphoric acid, 100 μl of the specimen solution with a 5-fold concentration, 100 μl of distilled water and 50 μl of 0.4 to 1 mg/ml rat liver microsome prepared by the following method were mixed.

(II) The above mixture was pre-incubated at 37° C. for 10 minutes and thereafter, 50 μl of 100 μM [$^3$H]-farnesylpyrophosphoric acid (30 mCi/mmol, NEN) was added to the mixture to start a reaction. The reaction was continued at 37° C. for 10 minutes. 1 ml of ethanol was added to the resulting mixture to terminate the reaction and then 1 ml of distilled water and 3 ml of petroleum ether were added to the reaction solution, which was then shaken for 30 minutes. The water phase was separated from the organic phase, the water phase was frozen at −70° C. in dry ice/methanol and the radio activity of the organic phase was measured using a liquid scintillator. Or the organic phase was evaporated to dryness using nitrogen gas and the residue was dissolved as a marker in 25 μl of chloroform containing squalene, farnesol and cholesterol. This sample was spotted on a TCL plate (Merck) and developed using heptane for 15 to 20 minutes. A band of squalene was cut from the plate to measure the radio activity by using a liquid scintillation counter. The data was expressed by a concentration ($IC_{50}$) at which 50% of the radio activity of a control group was inhibited.

Preparation Method for Rat Liver Microsome

All the following operations were performed on ice and centrifugation was performed at 4° C. Liver was extracted from a male Sprague-Dawly rat (hereinafter referred to as "SD rat") (8 to 9 weeks in age) and perfused with 1.15% potassium chloride to remove the blood. Then, the liver was finely excised with a pair of scissors and homogenized by use of a Teflon homogenizer. The obtained sample was centrifuged at 16,000× g for 15 minutes twice. The supernatant was further centrifuged at 105,000× g for 60 minutes and the obtained residue was used as a microsome fraction, which was suspended in 25 mM Tris-hydrochloric acid solution. The protein concentration of the suspension was quantitated by the Bradford method and the suspension was adjusted to 20 mg/ml with the same solution and stored at −70° C.

Test Example 2

Measurement of Cholesterol Biosynthesis Inhibitive Activity in a Rat Liver Cell

A liver cell was isolated from a male SD rat according to a usual method (collagenase perfusion method) and subjected to an experiment.

The isolated liver cells were planted in an amount of 500 μl every well on a Type collagen coated 24 well plate (cell density: 4×10$^5$ cell/ml). As the cell culture solution, a Williams' E medium (adjusted to pH 7.4) containing 10% FCS, 1 μM insulin, 1 μM dexamethasone, 100 units/ml penicillin and 100 μg/ml streptomycin was used. After the liver cells were incubated in a $CO_2$ incubator for 2 hours, unattached cells were removed and the liver cells were further incubated overnight.

After the culture medium was exchanged, the specimen diluted in a 10% DMSO-90% cell culture solution was added to each well inan amount of 5 μl. DMSO (final concentration: 0.1%) was added toacontrolgroup. A [1-$^{14}$C] Aceticacid, sodiumsalt (5 μCi/well) was added to the media 10 minutes after the specimen was added, followed by culturing for further 2 hours.

After the incubation was finished, the supernatant was removed and the cells were washed using PBS(−) (Phosphate buffered saline ($Ca^{2+}$, $Mg^{2+}$ free) twice. Hexane/isopropyl alcohol (3:2, v/v) was added to the cells and the cells were then allowed to stand for 10 minutes to extract intracellular lipid. The extract was transferred to a glass tube and exsiccated under a nitrogen gas stream. Further, the exsiccated extract was washed with 25 mL of petroleum ether and then dissolved in petroleum ether containing the following components: 0.01% squalene, 0.3% free cholesterol, 0.3% cholesterol acetate, 0.1% triolein, 0.01% farnesol and 0.3% lanosterol.

The resulting solution was spotted on a TLC plate to perform an isolating operation. The spot was developed for 10 minutes by using toluene/isopropyl ether (1:1, v/v) as the solvents and for further 15 minutes by using heptane in place of the above solvent after it was dried using air.

After the development was finished, the TLC plate was subjected to iodine color development. After each position of free cholesterol used as standards was confirmed, the image of the TLC plate was transferred to a BAS 2000 (Fuji Film) imaging plate by exposure performed for 16 hours. This transferred image was analyzed using a BAS 2000 IP Reader and an Imaging analyzer II to measure radio activities contained in the free cholesterol fractions.

The cholesterol biosynthesis inhibitive activity was expressed by a concentration ($IC_{50}$) at which 50% of the radio activity of the control group was inhibited.

The test results based on Test Example 1 (measurement of squalene synthase inhibitive activity by using a rat liver microsome), Test Example 2 (measurement of cholesterol biosynthesis inhibitive activity in a rat liver cell) are shown below.

TABLE 1

| Example | Squalene synthase inhibitive activity $IC_{50}$ (nM) |
|---|---|
| 1 | 1.4 |
| 7 | 0.53 |
| 9 | 0.78 |

TABLE 2

| Example | Cholesterol biosynthesis inhibitive activity $IC_{50}$ (nM) |
|---|---|
| 1 | 0.45 |
| 18 | 0.16 |

The compound according to the present invention is very useful as a squalene synthase inhibitor (Table 1) and also as a cholesterol biosynthesis inhibitor in actual (Table 2). Accordingly, the compound according to the present invention is useful as preventive and curative agents for a disease on which squalene synthase inhibition or cholesterol biosynthesis inhibition is effective. Also, as described in Br. J. Pharmacol. 2000 September; 131(1): 63–70, the correlation between serum cholesterol and triglyceride is disclosed and hence compounds that inhibit cholesterol biosynthesis are considered to have also a serum triglyceride decreasing action. From the above results, the compound according to the present invention is useful as a preventive and curative agent for hyperlipidemia and also as a preventive and curative agent for arterial sclerosis diseases or ischemic heart diseases.

EXAMPLES

The present invention will be explained in more detail and concretely by way of the following Examples, however, the present invention is not limited by them. The structural formulae of compounds in these Examples are listed in the following Table 3.

Production Examples

Production Example 1

2-Benzyl-3-iodo-6-[(3R,4R)-3-hydroxy-4-methoxypyrrolidine-1-yl]pyridine a) 2-Bromo-6-methoxypyridine While heating under stirring a mixture of 200 g of 2,6-dibromopyridine and 150 ml of methanol on an oil bath at 80° C., 250 ml of a 28% sodium methoxide/methanol solution was added dropwise slowly. The mixture was heated under stirring as it was for 2 hours, and after standing to cool, it was extracted with diethyl ether-water. The organic layer was washed with water and brine, and then dried over anhydrous magnesium sulfate. The solvent was removed, to give 150 g of the title compound.

$^1$H-NMR (CDCl$_3$) δ ppm=3.94 (3H, s), 6.68 (1H, d, J=7 Hz), 7.06(1H, d, J=8 Hz), 7.40(1H, t, J=8 Hz)

b) 2-Benzyl-6-methoxypyridine

While stirring a mixture of 150 g of 2-bromo-6-methoxypyridine, 4.3 g of 1,3-bis(diphenylphosphino)propanenickel (II) chloride and 500 ml of tetrahydrofuran in an ice bath, Grignard reagent prepared from 123 ml of benzyl bromide, 30 g of magnesium and 400 ml of diethyl ether was added dropwise slowly. After stirring overnight as it was, the mixture was extracted with an aqueous ammonium chloride solution and hexane. The organic layer was washed with water and then with brine, dried over anhydrous magnesium sulfate, and the solvent was removed. The residue was purified by silica gel column chromatography with (1% ethyl acetate/hexane and 1.5% ethyl acetate/hexane), to give 150 g of the title compound.

$^1$H-NMR(CDCl$_3$) δppm=3.92(3H, s), 4.03(2H, s), 6.54 (1H, d, J=8 Hz), 6.65(1H, d, J=7 Hz), 7.18–7.32(5H, m), 7.44(1H, dd, J=7, 8 Hz)

c) 2-Benzyl-6-hydroxypyridine

A mixture of 59 g of 2-benzyl-6-methoxypyridine and 200 ml of 47% hydrobromic acid was heated under stirring in an oil bath at 100° C. for 7 hours. After standing to cool, 250 ml of water was added and the resulting crystals were filtered, washed with water and dried under reduced pressure, to give 38.9 g of the title compound.

$^1$H-NMR(DMSO-d$_6$) δppm=3.78(2H, s), 5.96(1H, d, J=7 Hz), 6.15(1H, d, J=9 Hz), 7.20–7.36(6H, m)

d) 2-Benzyl-6-pyridyl trifluoromethanesulfonate

A mixture of 10 g of 2-benzyl-6-hydroxypyridine, 23 g of N-phenyltrifluoromethanesulfonimide, 0.66 g of 4-dimethylaminopyridine, 23 ml of triethylamine and 100 ml of dichloromethane was stirred in a water bath at room temperature for 1 hour. The reaction mixture was evaporated and the residue was subjected to silica gel column chromatography (2–3% ethyl acetate/hexane). Further, the eluted solution was filtered through NH-silica gel (Fuji Silysia Chemical Ltd.) and washed with 3% ethyl acetate/hexane. The filtrate was evaporated to give 11.7 g of the title compound.

$^1$H-NMR(CDCl$_3$) δppm=4.13(2H, s), 6.99(1H, d, J=8 Hz), 7.16(1H, d, J=8 Hz), 7.22–7.34(5H, m), 7.75(1H, t, J=8 Hz)

e) 2-Benzyl-6-[(3R,4R)-3,4-dihydroxypyrrolidin-1-yl]pyridine

To a mixture of 11.3 g of 2-benzyl-6-pyridyl trifluoromethanesulfonate, 11.3 g of (3R,4R)-3,4-dihydroxypyrrolidine acetate (synthesized from D-tartaric acid as a starting material, Angew. Chem. Int. Ed. Engl., 23(6), 435, 1984) and 10 ml of N-methylpyrrolidone was added dropwise 11 ml of 1,8-diazabicyclo[5.4.0]-7-undecene under nitrogen atmosphere in an oil bath at 100° C., followed by heating under stirring for 6 hours. After standing to cool, the reaction mixture was extracted with ethyl acetate-water. The organic layer was washed with water and brine, dried over anhydrous magnesium sulfate and evaporated. The residue was purified by silica gel column chromatography (ethyl acetate), to give 5.35 g of the title compound.

$^1$H-NMR(CDCl$_3$) δppm=3.47(2H, dd, J=2,11 Hz), 3.79 (2H, dd, J=4,11 Hz), 3.97(2H, s), 4.26–4.30(2H, m), 6.17 (1H, d, J=8 Hz), 6.38(1H, d, J=8 Hz), 7.19(1H, t, J=7 Hz), 7.26–7.36(5H, m)

f) 2-Benzyl-6-[(3R,4R)-3-hydroxy-4-methoxypyrrolidin-1-yl]pyridine

To a mixture of 5.35 g of 2-benzyl-6-[(3R,4R)-3,4-dihydroxypyrrolidin-1-yl]pyridine and 40 ml of tetrahydrofuran was added dropwise 800 mg of oily (60%) sodium hydride gradually under stirring, and the mixture was stirred as it was for 1 hour. Then, 1.24 ml of methyl iodide was added thereto and the resultant mixture was stirred overnight as it was. The reaction mixture was extracted with ethyl acetate-water, and the organic layer was washed with water and brine, dried over anhydrous magnesium sulfate and evaporated. The residue was purified by silica gel column chromatography (30% ethyl acetate/hexane), to give 2.18 g of the title compound.

$^1$H-NMR(CDCl$_3$) δppm=3.42(3H, s), 3.47–3.55(2H, m), 3.69–3.78(2H, m), 3.85–3.89(1H, m), 3.97(2H, s), 4.38–4.42(1H, m), 6.17(1H, d, J=8 Hz),6.35(1H, d, J=7 Hz), 7.19(1H, t, J=7 Hz), 7.26–7.35(5H, m)

g) 2-Benzyl-3-iodo-6-[(3R,4R)-3-hydroxy-4-methoxypyrrolidin-1-yl]pyridine

To a mixture of 3.11 g of 2-benzyl-6-[(3R,4R)-3-hydroxy-4-methoxypyrrolidin-1-yl]pyridine and 10 ml of N,N-dimethylformamide, while stirring in an ice bath, was added dropwise 2.5 g of N-iodosuccinimide, and the resultant mixture was stirred overnight as it was. To this was added sodium sulfite and the reaction mixture was extracted with ethyl acetate-water, and the organic layer was washed with water and brine, dried over anhydrous magnesium sulfate and evaporated. The residue was purified by silica gel column chromatography (30% ethyl acetate/hexane), to give 4.19 g of the title compound.

$^1$H-NMR(CDCl$_3$) δppm=3.41(3H, s), 3.42–3.51(2H, m), 3.64–3.71(2H, m), 3.84–3.87(1H, m), 4.19(2H, s), 4.38–4.42(1H, m), 5.98(1H, d, J=8 Hz), 7.18(1H, t, J=7 Hz), 7.26(2H, t, J=7 Hz), 7.37(2H, d, J=7 Hz), 7.69(1H, d, J=8 Hz)

Production Example 2

2-Benzyl-3-iodo-6-[(3R,4S)-3-hydroxy-4-methoxypyrrolidin-1-yl]pyridine a) 2-Benzyl-3-iodo-6-[(3S,4S)-3-(3-nitrobenzenesulfonyl)oxy-4methoxypyrrolidin-1-yl]pyridine To a solution of 10.0 g of 2-benzyl-3-iodo-6-[(3S,4S)-3-hydroxy-4-methoxypyrrolidin-1-yl]pyridine obtained in the same manner as in Production Example 1 by using (3S,4S)-3,4-dihydroxypyrrolidine acetate (Angew. Chem. Int. Ed. Engl., 23(6), 435, 1984) synthesized from L-tartaric acid as a starting material in 150 ml of ethyl acetate were added 300 mg of 4-dimethylaminopyridine, 10 ml of triethylamine and 9.7 g of 3-nitrobenzenesulfonyl chloride, followed by stirring at room temperature for 3 days. The reaction mixture was first filtered through 50 g of silica gel and washed with ethyl acetate. The filtrate was further filtered through 50 g of NH-silica gel and washed with ethyl acetate. The filtrate was concentrated, to give 14.6 g of the title compound.

$^1$H-NMR(CDCl$_3$) δppm=3.38(3H, s), 3.48(1H, d, J=12 Hz), 3.58–3.73(3H, m), 4.08–4.20(3H, m), 5.10–5.14(1H, m), 5.92(1H, d, J=8 Hz), 7.18(1H, t, J=7 Hz), 7.25(2H, t, J=7 Hz), 7.32(2H, d, J=7 Hz), 7.69(1H, d, J=8 Hz), 7.73(1H, t, J=8 Hz), 8.21(1H, d, J=8 Hz), 8.49(1H, d, J=8 Hz), 8.75(1H, s)

b) 2-Benzyl-3-iodo-6-[(3R,4S)-3-acetoxy-4-methoxypyrrolidin-1yl]pyridine

To a mixture of 7.9 g of cesium carbonate and 15 ml of dimethyl sulfoxide was added 4.2 ml of acetic acid. After foaming ceased, a mixture of 14.4 g of 2-benzyl-3-iodo-6-[(3S,4S)-3-(3-nitrobenzenesulfonyl)oxy-4-methoxypyrrolidin-1-yl]pyridine and 35 ml of dimethyl sulfoxide was added and the resultant mixture was heated under stirring under nitrogen atmosphere in an oil bath at 70° C. for 6 hours. After the reaction mixture was cooled, it was extracted with ethyl acetate-water. The organic layer was washed with water and brine, dried over anhydrous magnesium sulfate and concentrated. The residue was purified by silica gel column chromatography (10–15% ethyl acetate/hexane), to give 7.5 g of the title compound.

$^1$H-NMR(CDCl$_3$) δppm=2.12(3H, s), 3.42(3H, s), 3.37–3.73(4H, m), 4.04(1H, dt, J=4, 6 Hz), 4.19(2H, s), 5.42–5.47(1H, m), 5.96(1H, d, J=8 Hz), 7.19(1H, t, J=7 Hz), 7.27(2H, t, J=7 Hz), 7.38(2H, d, J=7 Hz), 7.70(1H, d, J=8 Hz)

c) 2-Benzyl-3-iodo-6-[(3R,4S)-3-hydroxy-4-methoxypyrrolidin-1-yl]pyridine

To a mixture of 7.5 g of 2-benzyl-3-iodo-6-[(3R,4S)-3-acetoxy-4-methoxypyrrolidin-1-yl]pyridine and 30 ml of methanol was added 0.33 ml of 28% methanol solution of sodium methoxide and the resultant mixture was stirred under nitrogen atmosphere at room temperature for 30 minutes. Water was added to the reaction mixture, which was extracted with ethyl acetate. The organic layer was washed with brine, dried over anhydrous magnesium sulfate and concentrated. The residue was purified by silica gel column chromatography (20–50% ethyl acetate/hexane), to give 6.7 g of the title compound.

$^1$H-NMR(CDCl$_3$) δppm=2.63(1H, d, J=5 Hz),3.38–3.67 (4H, m), 3.47(3H, s), 3.93(1H, q, J=5 Hz), 4.18(2H, s), 4.41(1H, quint., J=5 Hz), 5.96(1H, d, J=9 Hz), 7.18(1H, t, J=7 Hz), 7.26(2H, t, J=7 Hz), 7.37(2H, d, J=7 Hz), 7.69(1H, d, J=9 Hz)

Production Example 3

2-Benzyl-3-methoxymethyloxy-6-iodopyridine a) 2-Bromo-3-methoxymethyloxypyridine 50 g of 2-bromo-3-hydroxypyridine was suspended in 200 ml of tetrahydrofuran, to which 33 ml of chloromethyl methyl ether was added. The mixture was cooled to −20° C. and 17 g of 60% oily sodium hydride was portionwise added while stirring. After the addition of sodium hydride, the refrigerant was removed and the mixture was stirred at room temperature for 3.5 hours. In an ice bath, ice water was portionwise added and the reaction mixture was extracted with ethyl acetate. The organic layer was washed with brine and dried over anhydrous sodium sulfate. The solvent was removed, and the residue was purified by silica gel column chromatography (10–15% ethyl acetate/hexane), to give 35 g of the title compound.

$^1$H-NMR(CDCl$_3$) δppm=3.53(3H, s), 5.28(2H, s), 7.21 (1H, dd, J=4.6, 8.2 Hz), 7.43(1H, dd, J=1.6, 8.2 Hz), 8.05(1H, dd, J=1.6, 4.6 Hz)

b) 2-Benzyl-3-methoxymethyloxypyridine

While stirring a mixture of 35 g of 2-bromo-3-methoxymethyloxypyridine, 5 g of 1,3-bis(diphenylphosphino)propanenickel (II) chloride and 200 ml of tetrahydrofuran under ice-cooling, a diethyl ether solution of benzylmagnesium bromide prepared from 38 ml of benzyl bromide, 8 g of magnesium and 250 ml of anhydrous diethyl ether was slowly added dropwise thereinto under nitrogen atmosphere. After stirring for 4.5 hours, a saturated aqueous ammonium chloride solution was added thereto, and the mixture was extracted with ethyl acetate. The organic layer was washed with brine and dried over anhydrous sodium sulfate. The solvent was removed, and the residue was purified by silica gel column chromatography (8–20% ethyl acetate/hexane), to give 27 g of the title compound.

$^1$H-NMR(CDCl$_3$) δppm=3.34(3H, s), 4.21(2H, s), 5.17 (2H, s) 7.11–7.38(7H, m), 8.20(1H, dd, J=1.3, 4.8 Hz)

c) 2-Benzyl-3-methoxymethyloxy-6-iodopyridine

To 27 g of 2-benzyl-3-methoxymethyloxypyridine was added 60 ml of trifluoroacetic acid, and the mixture was stirred at room temperature for 2 hours and further heated under stirring in an oil bath at 50° C. for 1 hour. The reaction mixture was added to an ice-cooled aqueous potassium carbonate solution and the resulting crystals were collected by filtration and dried under reduced pressure. To the resulting crystals were added 19 g of sodium iodide, 5 g of sodium hydroxide and 200 ml of methanol, and 158 ml of an aqueous 5% sodium hypochlorite solution was added dropwise over 30 minutes while stirring in an ice bath. After stirring overnight as it was, 60 ml of 5 N hydrochloric acid and further a saturated aqueous sodium thiosulfate solution were added thereto and the mixture was extracted with ethyl acetate. The organic layer was washed with brine and dried over anhydrous sodium sulfate. The solvent was removed, and the resulting crystals were collected by filtration and dried under reduced pressure, to give 17 g of 2-benzyl-3-hydroxy-6-iodopyridine.

12 g of 2-benzyl-3-hydroxy-6-iodopyridine was dissolved in 50 ml of tetrahydrofuran and 3.8 ml of chloromethyl methyl ether was added thereto. While stirring in an ice bath, 2 g of 60% oily sodium hydride was portionwise added to the mixture. After the addition of sodium hydride, the refrigerant was removed and the mixture was stirred at room temperature for 2.5 hours. Thereafter, in an ice bath, ice water was portionwise added thereto, and the mixture was extracted with ethyl acetate. The organic layer was washed with brine and dried over anhydrous sodium sulfate. The solvent was removed and the residue was purified by silica gel column chromatography (15% ethyl acetate/hexane), to give 13 g of the title compound.

$^1$H-NMR(CDCl$_3$) δppm=3.28(3H, s), 4.14(2H, s), 5.11 (2H, s), 7.04(1H, d, J=8.4 Hz), 7.14–7.30(5H, m), 7.48(1H, d, J=8.4 Hz)

Production Example 4

2-Benzyl-1-methoxymethyloxy-4-iodobenzene a) 2-Benzyl-1-hydroxy-4-iodobenzene 6.87 g of 2-benzylphenol, 7.2 g of sodium iodide and 1.7 g of sodium hydroxide were added to 60 ml of methanol and while stirring in an ice bath, 50 ml of an aqueous 5% sodiumhypochlorite solution was added dropwise to the mixture over 30 minutes. The temperature was slowly returned to room temperature and the stirring was continued overnight. Water was added to the reaction mixture, which then was extracted with ethyl acetate, washed with brine and then dried over anhydrous magnesium sulfate. The solvent was removed and the residue was purified by silica gel column chromatography (30% ethyl acetate/hexane), to give 10.1 g of the title compound.

$^1$H-NMR(CDCl$_3$) δppm=3.92(2H, s), 4.91(1H, s), 6.56 (1H, d, J=8.4 Hz) 7.15–7.30(5H, m), 7.37–7.43(2H, m)

b) 2-Benzyl-1-methoxymethyloxy-4-iodobenzene 10.1 g of 2-benzyl-1-hydroxy-4-iodobenzene and 3 ml of chloromethyl methyl ether were added to 100 ml of tetrahydrofuran and while stirring on an ice bath, 1.45 g of 60% (oily) sodium hydride was added dropwise to the mixture. After stirring for 2 hours, water was added to the reaction mixture, which then was extracted with ethyl acetate, washed with saturated brine and thereafter dried over anhydrous magnesium sulfate. The solvent was removed, and the residue was purified by silica gel column chromatography with 10% ethyl acetate/hexane, to give 8.7 g of the title compound.

$^1$H-NMR(CDCl$_3$) δppm=3.33(3H, s), 3.92(2H, s), 5.13 (2H, s), 6.84(1H, d, J=8.4 Hz), 7.14–7.30(5H, m), 7.41(1H, d, J=2 Hz), 7.45(1H, dd, J=8.4 Hz)

Production Example 5

2-Benzyl-4-(2-pyrrolidinon-1-yl)phenyl trifluoromethanesulfonate a) 2-Benzyl-1-methoxymethyloxy-4-(2-pyrrolidinon-1-yl)benzene A mixture of 560 mg of 2-benzyl-1-methoxymethyloxy-4-iodobenzene (Production Example 4), 5 ml of 2-pyrrolidone, 90 mg of copper iodide (I), and 400 mg of anhydrous potassium carbonate was heated under stirring under nitrogen atmosphere on an oil bath at 140° C. for 8 hours. Aqueous ammonia was added to the reaction mixture, and the mixture was extracted with ethyl acetate. Then it was successively washed with water and brine, dried over anhydrous magnesium sulfate and then evaporated, to give 505 mg of the title compound.

$^1$H-NMR(CDCl$_3$) δppm=2.07–2.17(2H, m), 2.57(2H, t, J=8 Hz), 3.35(3H, s), 3.78(2H, t, J=7 Hz), 4.00(2H, s), 5.13(2H, s), 7.07(1H, d, J=8 Hz), 7.14–7.30(5H, m), 7.35–7.40(2H, m)

b) 2-Benzyl-4-(2-pyrrolidinon-1-yl)phenol

A mixture of 505 mg of 2-benzyl-1-methoxymethyloxy-4-(2-pyrrolidinon-1-yl)benzene and 5 ml of trifluoroacetic acid was stirred at room temperature for 1 hour. The reaction mixture was evaporated, and the residue was purified by silica gel column chromatography with 30–60% ethyl acetate/hexane, to give 320 mg of the title compound.

$^1$H-NMR(CDCl$_3$) δppm=2.07–2.17(2H, m), 2.58(2H, t, J=8 Hz), 3.77(2H, t, J=7 Hz), 3.98(2H, s), 5.28(1H, brs), 6.74(1H, d, J=9 Hz), 7.19–7.32(7H, m)

c) 2-Benzyl-4-(2-pyrrolidinon-1-yl)phenyl trifluoromethanesulfonate 320 mg of 2-benzyl-4-(2-pyrrolidinon-1-yl)phenol, 520 mg of N-phenyltrifluoromethanesulfonimide, 15 mg of 4-dimethylaminopyridine and 0.5 ml of triethylamine were dissolved in 2.5 ml of dichloromethane, followed by stirring at room temperature overnight. The reaction mixture was purified by silica gel column chromatography with 30% ethyl acetate/hexane, to give 450 mg of the title compound.

$^1$H-NMR(CDCl$_3$) δppm=2.09–2.18(2H, m),2.59(2H, t, J=8 Hz),3.76(2H, t, J=7 Hz), 4.08(2H, s), 7.17–7.34(6H, m), 7.48(1H, d, J=3 Hz), 7.61(1H, dd, J=9 Hz)

Production Example 6

2-Benzyl-3-hydroxy-6-(2-pyrrolidinon-1-yl)pyridine

This was synthesized in the same manner as in Production Example 5-a and b except that 2-benzyl-3-methoxymethyloxy-6-iodopyridine (Production Example 3) was used as a starting material.

¹H-NMR(CDCl₃) δppm=2.06–2.15(2H, m), 2.64(2H, t, J=8 Hz), 4.08(2H, t, J=7 Hz), 4.13(2H, s), 4.69(1H, brs), 7.12(1H, d, J=9 Hz), 7.19–7.32(5H, m), 8.12(1H, d, J=9 Hz)

Production Example 7

2-Benzyl-6-[(3R,4R)-3,4-dimethoxy-2-pyrrolidinon-1-yl]-3-pyridyl trifluoromethanesulfonate (A) and 2-benzyl-6-[(3R,4R)-4-hydroxy-3-methoxy-2-pyrrolidinon-1-yl]-3-pyridyl trifluoromethanesulfonate (B)

a) 2-Benzyl-3-methoxymethyloxy-6-[(3R,4R)-3,4-dimethylmethylenedioxy-2-pyrrolidinon-1-yl]pyridine 3.6 g of 2-benzyl-3-methoxymethyloxy-6-iodopyridine (Production Example 3), 1.5 g of (3R,4R)-3,4-dimethylmethylenedioxy-2-pyrrolidinone synthesized by the known method as described in the literature document (J. Org. Chem., 1969, 34, 675.), 1.1 g of copper iodide (I), and 3.3 g of potassium carbonate were suspended in 20 ml of 1-methyl-2-pyrrolidone, followed by heating under stirring in an oil bath at 140° C. for 20 minutes under nitrogen atmosphere. After standing to cool, ethyl acetate and aqueous ammonia were added thereto and the mixture was extracted with ethyl acetate. The organic layer was washed with brine and dried over anhydrous sodium sulfate. The solvent was removed, and the residue was purified by silica gel column chromatography with 20–50% ethyl acetate/hexane, to give 2 g of the title compound.

¹H-NMR(CDCl₃) δppm=1.42(3H, s), 1.46(3H, s), 3.37 (3H, s), 4.08–4.13(3H, m), 4.26(1H, d, J=13 Hz), 4.80(2H, s), 5.14(2H, dd, J=6.8, 10 Hz),7.17–7.31(5H, m), 7.42(1H, d, J=9.0 Hz), 8.22(1H, d, J=9.0 Hz)

b) 2-Benzyl-6-[(3R,4R)-3,4-dimethylmethylenedioxy-2-pyrrolidinon-1-yl]-3-pyridyl trifluoromethanesulfonate To 2 g of 2-benzyl-3-methoxymethyloxy-6-[(3R,4R)-3,4-dimethylmethylenedioxy-2-pyrrolidinon-1-yl]pyridine was added 5 ml of trifluoroacetic acid, followed by stirring at room temperature for 6 hours. Thereafter, the reaction mixture was neutralized with an aqueous potassium carbonate solution and extracted with ethyl acetate. Further, the organic layer was washed with brine and dried over anhydrous sodium sulfate. The solvent was removed and the resulting residue was dissolved in 30 ml of dichloromethane. 2.1 g of N-phenyltrifluoromethanesulfonimide, 192 mg of 4-dimethylaminopyridine and 0.8 ml of triethylamine were added thereto, followed by stirring at room temperature for 1 hour. Then, the solvent was removed, and the residue was purified by silica gel column chromatography with 25% ethyl acetate/hexane, to give 2.2 g of the title compound.

¹H-NMR(CDCl₃) δppm=1.42(3H, s), 1.46(3H, s), 4.03 (1H, dd, J=4.0, 13 Hz), 4.18(2H, s), 4.23(1H, d, J=13 Hz), 4.79–4.83(2H, m), 7.20–7.42(5H, m), 7.60(1H, d, J=9.2 Hz), 8.44(1H, d, J=9.2 Hz)

c) 2-Benzyl-6-[(3R,4R)-3,4-dimethoxy-2-pyrrolidinon-1-yl]pyridyl trifluoromethanesulfonate (A) and 2-Benzyl-6-[(3R,4R)-4-hydroxy-3-methoxy-2-pyrrolidinon-1-yl]-3-pyridyl trifluoromethanesulfonate (B)

2.2 g of 2-benzyl-6-[(3R,4R)-3,4-dimethylmethylenedioxy-2-pyrrolidinon-1-yl]-3-pyridyl trifluoromethanesulfonate was dissolved in 20 ml of methanol and 5 ml of 5 N hydrochloric acid was added, followed by stirring at room temperature for 1.5 hours and then in an oil bath at 50° C. for 2 hours. After standing to cool, the reaction mixture was neutralized with an aqueous potassium carbonate solution and extracted with ethyl acetate. Further, the organic layer was washed with brine and dried over anhydrous sodium sulfate. The solvent was removed and the resulting residue was dissolved in 20 ml of acetonitrile. 1.5 ml of methyl iodide and 5.6 g of silver (I) oxide were added thereto, followed by heating under stirring in an oil bath at 60° C. for 1.5 hours. The insoluble matters were filtered through Celite. The filtrate was evaporated and separation, and separated and purified and by silica gel column chromatography with 33–50% ethyl acetate/hexane as an elution solvent, to give 685 g of the title compound (A) and 599 mg of the title compound (B).

Compound (A): ¹H-NMR(CDCl₃) δppm=3.47(3H, s), 3.69(3H, s), 3.80(1H, dd, J=3.8, 12 Hz), 4.07–4.21(5H, m), 7.22–7.29(5H, m), 7.58(1H, d, J=9.2 Hz), 8.38(1H, d, J=9.2 Hz)

Compound (B): ¹H-NMR(CDCl₃) δppm=3.48(1H, d, J=4.6 Hz), 3.74(3H, s), 3.86(1H, dd, J=13 Hz, 4.0 Hz), 4.06–4.18(4H, m), 4.54–4.57(1H, m), 7.24–7.30(5H, m), 7.59(1H, d, J=9.0 Hz), 8.37(1H, d, J=9.0 Hz)

Production Example 8

2-Benzyl-4[(3R,4R)-3,4-dimethoxy-2-pyrrolidinon-1-yl] phenyl trifluoromethanesulfonate This was synthesized in the same manner as in Production Example 7 except that 2-benzyl-3-methoxymethyloxy-4-iodobenzene (Production Example 4) was used as a starting material.

¹H-NMR(CDCl₃) δppm=3.48(3H, s), 3.68(3H, s), 3.74 (2H, d, J=3.2 Hz) 4.01(1H, d, J=5.2 Hz), 4.08(2H, s), 4.10–4.17(1H, m), 7.15–7.35(6H, m), 7.48(1H, d, J=3 Hz), 7.62(1H, dd, J=3, 9 Hz)

Production Example 9

2-Benzyl-4-[(3R,4R)-4-hydroxy-3-methoxy-2-pyrrolidinon-1-yl]phenyl trifluoromethanesulfonate This was synthesized in the same manner as in Production Example 7 except that 2-benzyl-1-methoxymethyloxy-4-iodopyridine (Production Example 4) was used as a starting material.

¹H-NMR(CDCl₃) δppm=2.75(1H, brs), 3.70(1H, dd, J=1, 10 Hz), 3.72(3H, s), 3.79(1H, dd, J=4, 10 Hz), 4.01(1H, d, J=5 Hz), 4.07(2H, s), 4.52–4.56(1H, m), 7.16–7.34(6H, m), 7.47(1H, d, J=3 Hz), 7.64(1H, dd, J=3, 9 Hz)

Production Example 10

(3R,4S)-1-(3-Benzylphenyl)-3,4-dihydroxypyrrolidine a) 1-(3-Bromophenyl)-2,5-dihydropyrrole In an ice bath, 26 ml of methanesulfonyl chloride was added dropwise in to a mixture of 10 g of cis-2-buten-1,4-diol, 63 ml of triethylamine and 1000 ml of ethyl acetate, followed by stirring at the same temperature for 3 hours. Then, the insoluble matters were removed by filtration. The filtrate was further filtered through silica gel and washed with ethyl acetate. Then, the filtrate was evaporated, to give 21.4 g of cis-1,4-bis(methanesulfonyloxy)-2-butene.

Then, a mixture of 15 g of the cis-1,4-bis(methanesulfonyloxy)-2-butene, 10 g of 3-bromoaniline, 24 g of anhydrous potassium carbonate and 70 ml of N,N-dimethylformamide was stirred at room temperature overnight. The reaction mixture was extracted with ethyl acetate-water, and the organic layer was washed with water and brine, dried over anhydrous magnesium sulfate and then evaporated. The residue was purified by silica gel column chromatography with 5% ethyl acetate/hexane, to give 6.6 g of the title compound.

$^1$H-NMR(CDCl$_3$) δppm=4.08(4H, s), 5.94(2H, s), 6.43 (1H, dd, J=2, 7 Hz), 6.65(1H, t, J=2 Hz), 6.78(1H, dd, J=2, 7 Hz), 7.08(1H, t, J=7 Hz)

b) 1-(3-Benzylphenyl)-2,5-dihydropyrrole

To a mixture of 6.6 g of 1-(3-bromophenyl)-2,5-dihydropyrrole, 800 mg of 1,3-bis(diphenylphosphino)propanenickel (II) chloride and 40 ml of tetrahydrofuran was added dropwise 22 ml of a 2.0 M tetrahydrofuran solution of benzyl magnesium chloride, followed by stirring overnight as it was. The reaction mixture was separated with a saturated aqueous ammonium chloride solution-ethyl acetate, and the organic layer was washed with water and brine, dried over anhydrous magnesium sulfate and then evaporated. The residue was purified by silica gel column chromatography with 1% ethyl acetate/hexane, to give 2.1 g of the title compound.

$^1$H-NMR(CDCl$_3$) δppm=3.95(2H, s), 4.08(4H, s), 5.93 (2H, s), 6.35–6.41(2H,m), 6.52(1H, br.d, J=7 Hz), 7.14–7.30 (6H, m)

c) (3R,4S)-1-(3-Benzylphenyl)-3,4-dihydroxypyrrolidine

While stirring 20 ml of an acetone solution of 2.1 g of 1-(3-benzylphenyl)-2,5-dihydropyrrole on an ice bath, 2.2 ml of a 50% aqueous solution of N-methylmorpholine-N-oxide, 4 ml of water and 0.5 ml of a 2.5% t-butanol solution of osmium tetroxide were successively added thereto, followed by stirring as it was at room temperature overnight. After adding 2 ml of a 1 M aqueous solution of sodium thiosulfate, the reaction mixture was extracted with ethyl acetate-water. The organic layer was washed with water and brine, dried over anhydrous magnesium sulfate and evaporated. The residue was purified by silica gel column chromatography with 10–50% ethyl acetate/hexane, to give 1.15 g of the title compound.

$^1$H-NMR(CDCl$_3$) δppm=2.47(2H, br.s), 3.27(2H, dd, J=4, 10 Hz), 3.53(2H, dd, J=6, 10 Hz), 3.92(2H, s), 4.14(2H, br.s), 6.34–6.41(2H, m), 6.56(1H, d, J=7 Hz), 7.12–7.30(6H, m)

Production Example 11

(3R,4S)-1-(3-Benzylphenyl)-3,4-dimethoxypyrrolidine

While stirring a mixture of 270 mg of (3R,4S)-1-(3-benzylphenyl)-3,4-dihydroxypyrrolidine (Production Example 10) and 5 ml of N,N-dimethylformamide in an ice bath, 0.15 ml of iodomethane and 100 mg of sodium hydride were added thereto, followed by stirring at the same temperature for 3 hours. The reaction mixture was extracted with ethyl acetate-water, and the organic layer was washed with water and brine, dried over anhydrous magnesium sulfate and evaporated. The residue was purified by silica gel column chromatography with 5–15% ethyl acetate/hexane, to give 250 mg of the title compound.

$^1$H-NMR(CDCl$_3$) δppm=3.38(2H, dd, J=4, 10 Hz), 3.44–3.49(2H, m), 3.46(6H, s), 3.93(2H, s), 3.97–4.02(2H, m), 6.35–6.41(2H, m), 6.53(1H, d, J=7 Hz), 7.12–7.30(6H, m)

Production Example 12

1-(3-Benzylphenyl)-cis-3-hydroxy-4-methoxypyrrolidine

This was synthesized in the same manner as in Production Example 11 except that 1 equivalent of each of sodium hydride and iodomethane were used to (3R,4S)-1-(3-Benzylphenyl)-3,4-dihydroxypyrrolidine (Production Example 10).

$^1$H-NMR(CDCl$_3$) δppm=2.73(1H, d, J=6 Hz), 3.24–3.36 (2H, m), 3.45–3.54(5H, m), 3.91–3.97(3H, m), 4.37–4.43 (1H, m), 6.34–6.41(2H, m), 6.54(1H, d, J=7 Hz), 7.11–7.30 (6H, m)

Production Example 13

1-(3-Bromophenyl)-trans-3-hydroxy-4-methoxypyrrolidine a) Cis-oxirane-2,3-dimethanol To a mixture of 4 g of cis-2-buten-1,4-diol and 100 ml and ethyl acetate was added 10 g of m-chloroperbenzoic acid (70% content) under ice-cooling, followed by stirring as it was at room temperature for 4 days. The reaction mixture was concentrated and the resulting m-chlorobenzoic acid was separated by filtration, and then 2.3 g of crystals of the entitled compound was obtained from the mother liquor.

$^1$H-NMR(CDCl$_3$) δppm=2.07(2H, m), 3.24–3.32(2H, m), 3.78–3.94(4H, m)

b) Cis-2,3-bis(methanesulfonyloxymethyl)oxirane

To a mixture of 2.3 g of cis-oxirane-2,3-dimethanol and 200 ml of ethyl acetate was added 9.3 ml of triethylamine and then 4.3 ml of methanesulfonyl chloride under ice-cooling, followed by stirring at the same temperature for 4 hours. The reaction mixture was filtered through silica gel and washed with ethyl acetate. Thereafter, the filtrate was evaporated, to give 5.4 g of the title compound.

$^1$H-NMR(CDCl$_3$) δppm=3.11(6H, s), 3.44–3.48(2H, m), 4.35(2H, dd, J=6, 12 Hz), 4.46(2H, dd, J=4, 12 Hz)

c) 1-(3-Bromophenyl)-3,4-epoxypyrrolidine

A mixture of 5.4 g of cis-2,3-bis(methanesulfonyloxymethyl)oxirane, 2 ml of 3-bromoaniline, 4.3 g of anhydrous potassium carbonate and 30 ml of N,N-dimethylformamide was stirred under nitrogen atmosphere at 60° C. for 2 hours and at 110° C. for 2 hours. The reaction mixture was extracted with ethyl acetate-water, and the organic layer was washed with water and brine, dried over anhydrous magnesium sulfate and then evaporated. The residue was purified by silica gel column chromatography with 5–10% ethyl acetate/hexane, to give 420 mg of the title compound.

$^1$H-NMR(CDCl$_3$) δppm=3.30(2H, d, J=12 Hz), 3.69(2H, d, J=12 Hz), 3.87(2H, s), 6.41(1H, dd, J=2, 8 Hz), 6.63(1H, t, J=2 Hz), 6.80(1H, dd, J=2, 8 Hz), 7.05(1H, t, J=8 Hz)

d) 1-(3-Bromophenyl)-trans-3-hydroxy-4-methoxypyrrolidine

A mixture of 420 mg of 1-(3-bromophenyl)-3,4-epoxypyrrolidine, 0.7 ml of a 28% methanol solution of sodium methoxide and 5 ml of methanol was stirred at 50° C. for 4 hours. The reaction mixture was extracted with ethyl acetate-water, and the organic layer was washed with water and brine, dried over anhydrous magnesium sulfate and the evaporated. The residue was purified by silica gel column chromatography with 10–30% ethyl acetate/hexane, to give 460 mg of the entitled compound.

$^1$H-NMR(CDCl$_3$) δppm=1.85(1H, d, J=5 Hz), 3.22–3.30 (2H, m), 3.41(3H, s), 3.55–3.64(2H, m), 3.86–3.89(1H, m), 4.38–4.43(1H, m), 6.46(1H, dd, J=2, 8 Hz), 6.68(1H, t, J=2 Hz), 6.80(1H, dd, J=2, 8 Hz), 7.06(1H, t, J=8 Hz)

Production Example 14

2-(4-Bromophenyl)-6-methyl-1,3,6,2-dioxyazaborocane 107 g of 4-bromophenylboric acid and 92 ml of N-methyldiethanolamine were suspended in 1000 ml of toluene, followed by heating under reflux for 2 hours while removing water. The toluene was removed and the resulting solid matter was collected by filtered and washed with hexane-toluene. The collected solid was recrystallized from toluene, to give 128 g of the title compound.

$^1$H-NMR(CDCl$_3$) δppm=2.32(3H, s), 2.95–3.04(2H, m), 3.16–3.24(2H, m), 4.09–4.17(2H, m), 4.17–4.25(2H, m), 7.42(2H, d, J=8.4 Hz), 7.50(2H, d, J=8.4 Hz)

Production Example 15

1-tert-Butoxycarbonyl-3-ethynyl-3-piperidinol a) 1-tert-Butoxycarbonylpiperidin-3-one 10 g of 3-hydroxypiperidine and 15 ml of triethylamine were dissolved in 100 ml of tetrahydrofuran. While stirring in an ice bath, a solution of 22.9 g of di-tert-butyl dicarbonate in 50 ml of tetrahydrofuran was added dropwise thereto. After completion of the dropwise addition, the reaction mixture was stirred for 1 hour and then evaporated. 25 ml of triethylamine was added to the residue and a solution of 25 g of pyridine trioxide-sulfur complex in 100 ml of dimethyl sulfoxide was added dropwise thereto, followed by stirring for 2 hours. Ice water was added to the reaction mixture, and the mixture was extracted with ethyl acetate. The organic layer was successively washed with an aqueous hypochlorous acid solution, water and brine, dried over anhydrous magnesium sulfate and evaporated. The residue was purified by silica gel column chromatography with 30% ethyl acetate/hexane, to give 13.1 g of the title compound.

$^1$H-NMR(CDCl$_3$) δppm=1.47(9H, s), 1.94–2.02(2H, m), 2.47(2H, t, J=7 Hz), 3.59(2H, t, J=6 Hz), 4.00(2H, s)

b) 1-tert-Butoxycarbonyl-3-ethynyl-3-piperidinol

In a dry ice-acetone bath, 40 ml of a 1.6 M hexane solution of n-butyllithium was added dropwise to a solution of 6.07 g of trimethylsilylacetylene in 100 ml of tetrahydrofuran. After the temperature was once elevated to 0° C., the mixture was cooled again in a dry ice-acetone bath and a solution of 5.97 g of 1-tert-butoxycarbonylpiperidin-3-one in 50 ml of tetrahydrofuran was added dropwise thereto. After 1 hour, aqueous ammonia chloride was added thereto, and the mixture was extracted with ethyl acetate. The organic layer was washed with brine, dried over anhydrous magnesium sulfate and then evaporated. The residue was purified by silica gel column chromatography with 30% ethyl acetate/hexane. To the resulting compound were added 10 g of anhydrous potassium carbonate and 100 ml of methanol, followed by stirring for 2 hours. Water was added thereto, and the mixture was extracted with ethyl acetate, dried over anhydrous magnesium sulfate and evaporated, to give 4.8 g of the title compound.

$^1$H-NMR(DMSO-d$_6$) δppm=1.39(9H, s), 1.44–1.65(3H, m), 1.76–1.89(1H, m), 2.80–3.76(5H, m), 5.68(1H, s)

Production Example 16

1-Benzyl-3-(2-propynyloxy)pyrrolidine

On an ice bath, 233 mg of sodium hydride was added to a mixture of 948 mg of 1-benzyl-3-pyrrolidinol and 10 ml of N,N-dimethylformamide and the mixture was stirred at room temperature for 1 hour. There action mixture was cooled to −40° C. and 495 μl of propargyl bromide was added thereto. The temperature was elevated to room temperature and water and ethyl acetate were added to the reaction mixture. The organic layer was separated, washed with water and brine, dried over anhydrous magnesium sulfate and the solvent was removed. The residue was purified by NH-silica gel column chromatography with 15% ethyl acetate/hexane, to give 507 mg of the title compound.

$^1$H-NMR(CDCl$_3$) δppm=1.82–1.86(1H, m), 2.09–2.14(1H, m), 2.39(1H, s), 2.49–2.59(2H, m), 2.65–2.71(1H, m), 2.77–2.80(1H, m), 3.58–3.67(2H, m), 4.10–4.12(2H, m), 4.25–4.28(1H, m), 7.23–7.34(5H, m)

Production Example 17

1-Acetoxy-1-ethynylcyclohexane 12.1 g of 1-ethylnyl-1-cyclohexanol was dissolved in 200 ml of dichloromethane and 18.9 ml of acetic anhydride was added dropwise to the solution in an ice bath. Then, 2 ml of a 1 M dichloromethane solution of trimethylsilyl triflate was added dropwise to the solution. After stirring for 1 hour and 15 minutes, ice was added to the reaction mixture and a saturated aqueous sodium hydrogen carbonate solution was added thereto to basify the reaction mixture. After further stirring for 1 hour and 30 minutes, it was extracted with dichloromethane. After adding 8.1 mL of methanol to the organic layer, it was successively washed with a saturated aqueous sodium hydrogen carbonate solution and water, and dried over anhydrous magnesium sulfate. The solvent was evaporated, to give 22.2 g of the title compound.

$^1$H-NMR(CDCl$_3$) δppm=1.28–1.38(1H, m), 1.47–1.57(1H, m), 1.58–1.66(4H, m), 1.80–1.89(2H, m), 2.04(3H, s), 2.09–2.16(2H, m), 2.59(1H, s)

Production Example 18

1-(1-Ethynylcyclohexyl)piperidine 7.0 g of 1-acetoxy-1-ethynylcyclohexane (Production Example 17) was dissolved in 140 ml of tetrahydrofuran, and after 20.8 ml of piperidine was added dropwise thereto at room temperature, 208 mg of copper chloride (I) was added to the resulting yellow transparent solution. The resulting mixture was stirred in an oil bath at 95° C. for 2 hours. The reaction mixture was left to stand to cool to room temperature, 200 ml of diethyl ether was added thereto and extracted with 100 ml of an aqueous 2 N hydrochloric solution twice. After addition of about 200 ml of ice to the resultant acidic solution, sodium hydroxide was added to the solution until the solution became basic (pH=10). The solution was extracted with 100 ml of dichloromethane twice. The organic layer was dried over anhydrous magnesium sulfate. The solvent was removed, to give a brown solid. To the solid was added hexane and washed, and the solid was collected by filtration, to give 700 mg of the title compound.

$^1$H-NMR(CDCl$_3$) δppm=1.14–1.26(1H, m), 1.38–1.73(12H, m), 1.79–1.88(1H, m), 1.96–2.04(2H, m), 2.32(1H, s), 2.60–2.66(4H, m)

Production Example 19

1-Ethynyl-N-methylcyclohexylamine

This was synthesized in the same manner as in Production Example 18 except that 1-acetoxy-1-ethynylcyclohexane (Production Example 17) and a 40% methylamine/methanol solution were used.

$^1$H-NMR(DMSO-d$_6$) δppm=1.08–1.75(10H, m), 2.24(3H, s), 3.12(1H, s)

Production Example 20

2-[(1-Ethynylcyclohexyl)amino]ethanol

This was synthesized in the same manner as in Production Example 18 except that 1-acetoxy-1-ethynylcyclohexane (Production Example 17) and ethanolamine were used.

$^1$H-NMR(DMSO-d$_6$) δppm=1.10–1.75(10H, m), 2.64(2H, t, J=6 Hz), 3.12(1H, s), 3.43(2H, t, J=6 Hz), 4.47(1H, brs)

Production Example 21

2-Ethynylbicyclo[2.2.1]heptan-2-ol 500 mg of norcamphor was dissolved in 6 ml of tetrahydrofuran and the solution was added dropwise in a suspension of 543 mg of lithium acetylide-ethylenediamine complex in tetrahydrofuran at room temperature, and the resulting reaction mixture was stirred for 18 hours. After water was added to the resulting reaction mixture, it was evaporated while maintaining the temperature of the water bath at 25° C. The residue was extracted with ethyl acetate twice. The resulting organic layer was washed with brine, dried over anhydrous magnesium sulfate and evaporated, to give 523 mg of the title compound.

$^1$H-NMR(DMSO-d$_6$) δppm=1.11–2.20 (10H, m), 3.23 (1H, s), 5.35 (1H, s)

Production Example 22

(3R)-3-Ethynyl-3-quinuclidinol a) (3R)-3-Ethynyl-3-quinuclidinol.L-(+)-tartrate 15.1 g of 3-ethynyl-3-quinuclidinol and 15 g of L-(+)-tartaric acid were dissolved under heating in 300 ml of methanol. After standing to cool, the resulting crystals were collected by filtration and recrystallized from methanol for three times, to give 2.07 g of the title compound.

$^1$H-NMR(DMSO-d$_6$) δppm=1.45–1.54(1H, m), 1.68–1.78(1H, m), 1.83–2.03(3H, m), 2.83–3.01(5H, m), 3.21(1H, dd, J=2, 14 Hz), 3.50(1H, s), 4.05(2H, s)

b) (3R)-3-Ethynyl-3-quinuclidinol 15.6 g of (3R)-3-Ethynyl-3-quinuclidinol.L-(+)-tartrate was dissolved in 150 ml of water and 20 g of anhydrous potassium carbonate was gradually added dropwise to the solution under stirring. The resulting crystals were collected by filtration, washed with water and dried, to give 6.88 g of the title compound.

$^1$H-NMR(DMSO-d$_6$) δppm=1.20–1.30(1H, m), 1.47–1.55(1H, m), 1.70–1.90(3.H, m), 2.54–2.70(4H, m), 2.72(1H, dd, J=2, 14 Hz), 2.93(1H, d, J=14 Hz), 3.29(1H, s), 5.47(1H, s) $[α]^{24}_{589}$=+58.3 (c=1.02, MeOH) (literature; $[α]^{20}_{589}$=+54.5 (c=0.99, MeOH); Tetrahedron: Asymmetry, 6 (6), 1393, 1995)

Production Example 23

4-Ethynyl-1-azaadamantan-4-ol

To a solution of 0.2 ml of trimethylsilylacetylene in 2 ml of tetrahydrofuran was added dropwise 0.64 ml of a 1.56 mol hexane solution of n-butyllithium in a dry ice-acetone bath. After stirring for 30 minutes, a solution of 50 mg of 1-azaadamantane-4-one in 1 ml of tetrahydrofuran was added dropwise to the mixture. After further stirring for 30 minutes, 1 ml of methanol was added to the mixture and the temperature was elevated to room temperature. The solvent was removed and water was added to the resulting solid. Crystals that remained were collected by filtration, to give 17 mg of the title compound.

$^1$H-NMR(CDCl$_3$) δppm=1.52–2.06(5H, m), 2.26–2.38(2H, m), 2.58–2.61(1H, m), 2.91–3.58(6H, m)

Production Example 24

2-Benzyl-3-iodo-6-(3,3-ethylenedioxypyrrolidin-1-yl)pyridine a) 2-Bromo-6-(3,3-ethylenedioxypyrrolidin-1-yl)pyridine A mixture of 5.7 g of 2,6-dibromopyridine, 2.5 g of 3-hydroxypyrrolidine, 3.6 ml of 1,8-diazabicyclo[5.4.0]-7-undecene (DBU) and 20 ml of tetrahydrofuran was heated under stirring under nitrogen atmosphere in an oil bath at 70° C. for 11 hours. The reaction mixture was separated with ethyl acetate-water. The organic layer was washed with water and brine, dried over anhydrous magnesium sulfate, and then concentrated. The residue was subjected to silicagel column chromatography with 10–30% ethyl acetate/hexane, to give 5.9 g of 2-bromo-6-(3-hydroxypyrrolidin-1-yl)pyridine.

Then, to a solution of 2.8 ml of oxalyl chloride in 100 ml of dichloromethane were added dropwise 4.6 ml of dimethyl sulfoxide in a dry ice-acetone bath while stirring, a solution of 5.9 g of the 2-bromo-6-(3-hydroxypyrrolidin-1-yl)pyridine in 50 ml of dichloromethane and finally 17 ml of triethylamine, and the temperature was returned to room temperature over 1 hour. The reaction mixture was washed with water and brine, dried over anhydrous magnesium sulfate and concentrated. To the residue were added 50 ml of toluene, 7 ml of ethylene glycol and a catalytic amount of p-toluenesulfonic acid monohydrate, followed by heating under reflux for 3 hours while removing water. After cooling, it was washed with a saturated aqueous sodium hydrogen carbonate solution and brine, dried over anhydrous magnesium sulfate and concentrated. The residue was subjected to silica gel column chromatography with 5–7% ethyl acetate/hexane, to give 6.3 g of the title compound.

$^1$H-NMR(CDCl$_3$) δppm=2.30(2H, t, J=7 Hz), 3.54(2H, s), 3.58(2H, t, J=7 Hz), 3.96–4.04(4H, m), 6.22(1H, d, J=8 Hz), 6.70(1H, d, J=8 Hz), 7.24(1H, t, J=8 Hz)

b) 2-Benzyl-6-(3,3-ethylenedioxypyrrolidin-1-yl)pyridine

A mixture of 6.3 g of 2-bromo-6-(3,3-ethylenedioxypyrrolidin-1-yl)pyridine, 240 mg of 1,3-bis(diphenylphosphino)propanenickel (II) chloride and 20 ml of tetrahydrofuran was stirred in advance under nitrogen atmosphere in an ice bath. To this was added dropwise a diethyl ether solution of benzyl magnesium bromide prepared from 3.4 ml of benzyl bromide, 0.8 g of magnesium and 15 ml of diethyl ether, followed by stirring as it was at room temperature for overnight. The reaction mixture was partitioned between a saturated aqueous ammonium chloride solution and ethyl acetate. The organic layer was washed with brine, dried over anhydrous magnesium sulfate and then concentrated. The residue was subjected to silica gel column chromatography with 5–10% ethyl acetate/hexane, to give 6.6 g of the title compound.

$^1$H-NMR(CDCl$_3$) δppm=2.19(2H, t, J=7 Hz), 3.57(2H, s), 3.59(2H, t, J=7 Hz), 3.97 (2H, s), 4.01 (4H, s), 6.14 (1H, d, J=8 Hz), 6.34 (1H, d, J=7 Hz), 7.16–7.35(6H, m)

c) 2-Benzyl-3-iodo-6-(3,3-ethylenedioxypyrrolidin-1-yl)pyridine

A mixture of 6.6 g of 2-benzyl-6-(3,3-ethylenedioxypyrrolidin-1-yl)pyridine and 60 ml of N,N-dimethylformamide was stirred in advance in an ice bath. 5.5 g of N-iodosuccinimide was added thereto and the resultant mixture was stirred as it was at room temperature overnight. To the reaction mixture was added 10 ml of a 1 M aqueous solution of sodium thiosulfate and the reaction mixture was partitioned between ethyl acetate and water. The organic layer was washed with brine, dried over anhydrous magnesium sulfate and then concentrated. The residue was subjected to silica gel column chromatography with 5–10% ethyl acetate/hexane, to give 6.7 g of the title compound.

$^1$H-NMR(CDCl$_3$) δppm=2.17(2H, t, J=7 Hz), 3.50(2H, s), 3.54(2H, t, J=7 Hz), 4.00(4H, s), 4.18(2H, s), 5.95(1H, d, J=8 Hz), 7.18(1H, t, J=7 Hz), 7.26(2H, t, J=7 Hz), 7.37(2H, d, J=7 Hz), 7.68(1H, d, J=8 Hz)

Production Example 25

2-Benzyl-3-iodo-6-(4-methoxypiperidino)pyridine

The title compound was synthesized in the same manner as in Production Example 1-e except that (3R,4R)-3,4-dihydroxypyrrolidine acetate was replaced by 4-piperidinol.

$^1$H-NMR(CDCl$_3$) δppm=1.50–1.61(2H, m), 1.87–1.95(2H, m), 3.12–3.20(2H, m), 3.37(3H, s), 3.37–3.44(1H, m), 3.88–3.96(2H, m), 4.18(2H, s), 6.28(1H, d, J=9 Hz), 7.18(1H, t, J=8 Hz), 7.27(2H, t, J=8 Hz), 7.35(2H, d, J=8 Hz), 7.69(1H, d, J=9 Hz)

Production Example 26

2-Benzyl-3-iodo-6-[(3R,4R)-dimethoxypyrrolidin-1-yl]pyridine

The entitled compound was synthesized in the same manner as in Production Example 1-f except that 2 equivalents each of sodium hydride, oily (60%) and methyl iodide were used.

$^1$H-NMR (CDCl$_3$) δppm=3.40(6H, s), 3.48–3.62(4H, m), 3.91–3.93(2H, m), 4.18(2H, s), 5.98(1H, d, J=8 Hz), 7.18(1H, t, J=7 Hz), 7.26(2H, t, J=7 Hz), 7.37(2H, d, J=7 Hz), 7.67(1H, d, J=8 Hz)

Example 1

3-[2-Benzyl-6-[(3R,4R)-3-hydroxy-4-methoxypyrrolidin-1-yl]-3-pyridyl]ethynyl-3-piperidinol A mixture of 450 mg of 2-benzyl-3-iodo-6-[(3R,4R)-3-hydroxy-4-methoxypyrrolidin-1yl]-pyridine (Production Example 1), 272 mg of 1-tert-butoxycarbonyl-3-ethynyl-3-piperidinol (Production Example 15), 63.6 mg of tetrakis(triphenylphosphine)palladium (0), 41.9 mg of copper (I) iodide, 460 μl of triethylamine, 5 ml of methanol and 1 ml of N,N-dimethyl formamide was heated under reflux under nitrogen atmosphere for 3 hours. After standing to cool, water, ethyl acetate, an aqueous ammonia chloride solution were added to the reaction mixture, and the organic layer was washed with water and brine, dried over anhydrous magnesium sulfate and then the solvent was removed. To the residue were added 2 ml of trifluoroacetic acid and 2 ml of dichloromethane, followed by stirring at room temperature for 1 hour. The reaction mixture was neutralized with an aqueous sodium hydrogen carbonate solution and an organic layer was separated by adding ethyl acetate. The organic layer was washed with brine, dried over anhydrous magnesium sulfate and the solvent was removed. The residue was purified by NH-silica gel column chromatography with 5% methanol/ethyl acetate, to give 387 mg of the entitled compound.

$^1$H-NMR(CDCl$_3$) δppm=1.52–1.56(1H, m), 1.67–1.75(1H, m), 1.86–1.95(2H, m), 2.69–2.74(2H, m), 2.83–2.86(1H, m), 2.92–2.95(1H, m), 3.41(3H, s), 3.46–3.55(2H, m), 3.66–3.74(2H, m), 3.84–3.86(1H, m), 4.15(2H, s), 4.37–4.40(1H, m), 6.10–6.12(1H, m), 7.14–7.18(1H, m), 7.23–7.26(2H, m), 7.32–7.35(2H, m), 7.40–7.42(1H, m)

Example 2

3-[2-Benzyl-6-[(3R,4R)-3-hydroxy-4-methoxypyrrolidin-1-yl]-3-pyridyl]ethynyl-1-methyl-3-piperidinol To a mixture of 94.0 mg of 3-[2-Benzyl-6-[(3R,4R)-3-hydroxy-4-methoxypyrrolidin-1-yl]-3-pyridyl]ethynyl-3-piperidinol (Example 1), 34.6 μl of an aqueous solution of 37% formaldehyde and 1.5 ml of dichloromethane was added 73.4 mg of sodium triacetoxyborohydride under ice-cooling, followed by stirring at room temperature for 30 minutes. The organic layer was separated by adding water and ethyl acetate to the reaction mixture, and then it was washed with an aqueous sodium hydrogen carbonate solution and brine, dried over anhydrous magnesium sulfate, and the solvent was removed. The residue was purified by NH-silica gel column chromatography with 5% methanol/ethyl acetate, to give 79.0 mg of the title compound.

$^1$H-NMR(CDCl$_3$) δppm=1.62–1.71(2H, m), 1.82–2.08(3H, m), 2.30(3H, s), 2.33–2.36(1H, m), 2.62–2.77(2H, m), 3.41(3H, s), 3.46–3.55(2H, m), 3.67–3.74(2H, m), 3.84–3.87(1H, m), 4.15(2H, s), 4.39–4.40(1H, m), 6.12(1H, d, J=9 Hz), 7.14–7.27(3H, m), 7.38–7.44(3H, m)

Example 3

4-[2-Benzyl-6-[(3R,4R)-3-hydroxy-4-methoxypyrrolidin-1-yl]-3-pyridyl]-1-methyl-4-piperidinol To a mixture of 500 mg of 2-benzyl-3-iodo-6-[(3R,4R)-3-hydroxy-4-methoxypyrrolidin-1-yl]pyridine (Production Example 1) and 10 ml of diethyl ether was added dropwise 1.99 ml of a 2.45 M hexane solution of n-butyllithium at −78° C. After stirring at the same temperature for 30 minutes, a solution of 552 mg of 1-methyl-4-piperidone in 3 ml of diethyl ether was added dropwise thereto. After stirring at the same temperature for 30 minutes, the temperature was elevated to room temperature. The organic layer was separated by adding water and ethyl acetate to the reaction mixture, and then it was washed with water and brine, dried over anhydrous magnesium sulfate and the solvent was removed. The residue was purified by NH-silica gel column chromatography with 5% methanol/ethyl acetate, to give 125 mg of the title compound.

$^1$H-NMR(CDCl$_3$) δppm=1.86–1.89(2H, m), 2.04–2.09(2H, m), 2.31(3H, s), 2.44–2.50(2H, m), 2.67–2.70(2H, m), 3.39(3H, s), 3.42–3.50(2H, m), 3.64–3.72(2H, m), 3.83–3.84(1H, m), 4.34–4.36(1H, m), 4.41(2H, s), 6.16(1H, d, J=9 Hz), 7.13–7.15(1H, m), 7.21–7.24(2H, m), 7.32–7.33(2H, m), 7.43–7.45(1H, m)

Example 4

4-[2-Benzyl-6-[(3R,4R)-3-hydroxy-4-methoxypyrrolidin-1-yl]-3-pyridyl]-1-methyl-1,2,3,6-tetrahydropyridine A mixture of 63.0 mg of 4-[2-Benzyl-6-[(3R,4R)-3-hydroxy-4-methoxypyrrolidin-1-yl]-3-pyridyl]-1-methyl-4-piperidinol (Example 3) and 1.5 ml of 1 M acetic acid solution of hydrogen chloride was stirred at 70° C. for 9 hours. The reaction mixture was neutralized with an aqueous sodium hydrogen carbonate solution and extracted with ethyl acetate. The organic layer was washed with water and brine, dried over anhydrous magnesium sulfate, and the solvent was removed. To the residue were added 50 mg of potassium carbonate and 1 ml of methanol, followed by stirring at room temperature for 1 hour. NH-silica gel was added to the reaction mixture and the solvent was removed. It was purified by NH-silica gel column chromatography with 5% methanol/ethyl acetate, to give 10.2 mg of the title compound.

$^1$H-NMR(CDCl$_3$) δppm=2.26–2.27(2H, m), 2.39(3H, s), 2.58(2H, t, J=6 Hz), 3.03(2H, d, J=3 Hz), 3.40(3H, s), 3.44–3.52(2H, m), 3.67–3.75(2H, m), 3.84–3.87(1H, m), 4.01(2H, s), 4.36–4.38(1H, m), 5.42–5.43(1H, m), 6.18(1H, d, J=8 Hz), 7.13–7.30(6H, m)

Example 5

3-[3-[2-Benzyl-6-[(3R,4R)-3-hydroxy-4-methoxypyrrolidin-1-yl]-3-pyridyl]propyloxy]pyrrolidine A mixture of 742 mg of 2-benzyl-3-iodo-6-[(3R,4R)-3-hydroxy-4-methoxypyrrolidin-1-yl]pyridine (Production Example 1), 389 mg of 1-benzyl-3-(2-propynyloxy)pyrrolidine (Production Example 16), 62.7 mg of tetrakis(triphenylphosphine)palladium (0), 51.7 mg of copper (I) iodide, 757 μl of triethylamine, 4 ml of methanol and 4 ml of N,N-dimethylformamide was stirred under nitrogen atmosphere at 75° C. for 2 hours. After standing to cool, water, ethyl acetate and aqueous ammonia were added to the reaction mixture. The organic layer was separated, washed with water and brine, dried over anhydrous magnesium sulfate, filtered through NH-silica gel and the solvent was removed. After 10 ml of methanol, 1 ml of acetic acid and 50 mg of 10% palladium carbon were added to the residue and hydrogen substitution was performed, the mixture was stirred at room temperature overnight. After the reaction mixture was nitrogen-purged, it was filtered through Celite. The solvent was removed, and then the residue was purified by silica gel column chromatography with ethyl acetate/methanol/aqueous ammonia (100/5/2), to give 465 mg of the title compound.

$^1$H-NMR(CDCl$_3$) δppm=1.65–1.72(2H, m), 1.76–1.79(1H, m), 2.04–2.09(1H, m), 2.45–2.57(4H, m), 2.61–2.65(1H, m), 2.76–2.80(1H, m), 3.23–3.29(2H, m), 3.42(3H, s), 3.45–3.51(2H, m), 3.57–3.77(4H, m), 3.85–3.88(1H, m), 3.94–3.97(1H, m), 4.03(2H, s), 4.37–4.40(1H, m), 6.18(1H, d, J=8 Hz), 7.13–7.15(1H, m), 7.20–7.34(5H, m)

Example 6

1-[2-Benzyl-6-[3R,4S)-3-hydroxy-4-methoxypyrrolidin-1-yl]-3-pyridyl]ethynylcyclohexylamine To a mixture of 200 mg of 2-benzyl-3-iodo-6-[(3R,4S)-3-hydroxy-4-methoxypyrrolidin-1-yl]pyridine (Production Example 2), 100 mg of 1-ethynylcyclohexylamine, 15 mg of tetrakis(triphenylphosphine)palladium (0), 5 mg of copper (I) iodide and 0.3 ml of triethylamine was added 1 ml of N,N-dimethylformamide, followed by heating under stirring under nitrogen atmosphere in an oil bath at 80° C. for 3 hours. After standing to cool, aqueous ammonia was added to the reaction mixture, which then was extracted with ethyl acetate. The organic layer was dried over anhydrous sodium sulfate and the solvent was removed. The residue was purified by NH-silica gel column chromatography with ethyl acetate, to give 155 mg of the title compound.

$^1$H-NMR(CDCl$_3$) δppm=1.10–1.95(10H, m), 3.42–3.55 (5H, m), 3.60–3.72(2H, m), 3.94(1H, q, J=6 Hz), 4.17(2H, d, J=3 Hz), 4.38–4.43(1H, m), 6.12(1H, d, J=9 Hz), 7.15(1H, t, J=7 Hz), 7.22–7.28(2H, m), 7.35(2H, d, J=7 Hz), 7.42(1H, d, J=9 Hz)

Example 7

1-[2-Benzyl-6-[(3R,4R)-3-hydroxy-4-methoxypyrrolidin-1-yl]-3-pyridyl]ethynylcyclohexylamine This was synthesized in the same manner as in Example 6 except that 2-benzyl-3-iodo-6-[(3R,4R)-3-hydroxy-4-methoxypyrrolidin-1-yl]pyridine (Production Example 1) was used.

$^1$H-NMR(CDCl$_3$) δppm=1.10–1.91(10H, m), 3.41(3H, s), 3.45–3.55(2H, m), 3.66–3.75(2H, m), 3.83–3.88(1H, m), 4.17(2H, s), 4.37–4.42(1H, m), 6.14(1H, d, J=9 Hz), 7.15 (1H, t, J=7 Hz), 7.21–7.28(2H, m), 7.35(2H, d, J=7 Hz), 7.41(1H, d, J=9 Hz)

Example 8

1-[2-Benzyl-6-[(3R,4R)-3,4-dimethoxy-2-pyrrolidinon-1-yl]-3-pyridyl]ethynylcyclohexylamine This was synthesized in the same manner as in Example 6 except that 2-benzyl-6-[(3R,4R)-3,4-dimethoxy-2-pyrrolidinon-1-yl]-3-pyridyl trifluoromethanesulfonate (Production Example 7-A) was used.

$^1$H-NMR(CDCl$_3$) δppm=1.10–1.95(10H, m), 3.47(3H, s), 3.70(3H, s), 3.83(1H, dd, J=4, 13 Hz), 4.07(1H, d, J=5 Hz), 4.12–4.18(1H, m), 4.23(1H, dd, J=2, 13 Hz), 4.26(2H, d, J=2 Hz), 7.15–7.34(5H, m), 7.67(1H, d, J=9 Hz), 8.21(1H, d, J=9 Hz)

Example 9

1-[2-Benzyl-6-[(3R,4R)-4-hydroxy-3-methoxy-2-pyrrolidinon-1-yl]-3-pyridyl]ethynylcyclohexylamine This was synthesized in the same manner as in Example 6 except that 2-benzyl-6-[(3R,4R)-4-hydroxy-3-methoxy-2-pyrrolidinon-1-yl]-3-pyridyl trifluoromethanesulfonate (Production Example 7-B) was used.

$^1$H-NMR(CDCl$_3$) δppm=1.10–1.95(10H, m), 3.74(3H, s), 3.89(1H, dd, J=4, 13 Hz), 4.06 (1H, d, J=4 Hz), 4.18 (1H, d, J=13 Hz), 4.25 (2H, s), 4.54(1H, t, J=4 Hz), 7.15–7.35(5H, m), 7.68(1H, d, J=9 Hz) 8.20(1H, d, J=9 Hz)

Example 10

1-[1-[2-Benzyl-6-[(3R,4R)-3-hydroxy-4-methoxypyrrolidin-1-yl]-3-pyridyl]ethynylcyclohexyl]piperidine This was synthesized in the same manner as in Example 6 except that 2-benzyl-3-iodo-6-[(3R,4R)-3-hydroxy-4- methoxypyrrolidin-1-yl]pyridine (Production Example 1) and 1-(1-ethynylcyclohexyl)piperidine (Production Example 18) were used.

$^1$H-NMR(DMSO-d$_6$) δppm=1.18–1.64(14H, m), 1.86–1.93(2H, m), 2.46–2.56(4H, m), 3.24–3.52(7H, m), 3.71–3.75(1H, m), 4.08(2H, s), 4.17–4.21(1H, m), 5.22(1H, brs), 6.26(1H, d, J=8.4 Hz), 7.11–7.29(5H, m), 7.42(1H, d, J=8.4 Hz)

Example 11

1-[2-Benzyl-6-[(3R,4R)-3-hydroxy-4-methoxypyrrolidin-1-yl]-3-pyridyl]ethynyl-N-methylcyclohexylamine This was synthesized in the same manner as in Example 6 except that 2-benzyl-3-iodo-6-[(3R,4R)-3-hydroxy-4-methoxypyrrolidin-1-yl]pyridine (Production Example 1) and 1-ethynyl-N-methylcyclohexylamine (Production Example 19) were used.

$^1$H-NMR(DMSO-d$_6$) δppm=1.05–1.82(10H, m), 2.30(3H, s), 3.24–3.52(7H, m), 3.72(1H, brs), 4.07(2H, s), 4.19(1H, brs), 5.23(1H, brs), 6.26(1H, d, J=8.4 Hz), 7.12–7.31(5H, m), 7.40(1H, d, J=8.4 Hz)

Example 12

2-[[1-[2-Benzyl-6-[(3R,4R)-3-hydroxy-4-methoxypyrrolidin-1-yl]-3-pyridyl]ethynylcyclohexyl]amino]ethanol This was synthesized in the same manner as in Example 6 except that 2-benzyl-3-iodo-6-[(3R,4R)-3-hydroxy-4-methoxypyrrolidin-1-yl]pyridine (Production Example 1) and 2-[(1-ethynylcyclohexyl)amino]ethanol (Production Example 20) were used.

$^1$H-NMR(DMSO-d$_6$) δppm=1.11–1.86(10H, m), 2.73(2H, t, J=6 Hz), 3.27 (3H, s), 3.41–3.51(4H, m), 3.73 (1H, brs), 4.06(2H, s), 4.19(1H, brs), 4.49(2H, t, J=6 Hz), 5.23(1H, d, J=3 Hz), 6.26(1H, d, J=8.4 Hz), 7.13–7.31(5H, m), 7.40(1H, d, J=8.4 Hz)

Example 13

3-[2-Benzyl-6-[(3R,4R)-3-hydroxy-4-methoxypyrrolidin-1-yl]-3-pyridyl]-1,1-diethyl-2-propynylamine This was synthesized in the same manner as in Example 6 except that 2-benzyl-3-iodo-6-[(3R,4R)-3-hydroxy-4-methoxypyrrolidin-1-yl]pyridine (Production Example 1) and 1,1-diethyl-2-propynylamine were used.

$^1$H-NMR(CDCl$_3$) δppm=1.04(6H, t, J=8 Hz), 1.50–1.75 (4H, m), 3.40(3H, s), 3.45–3.54(2H, m), 3.65–3.74(2H, m), 3.82–3.86(1H, m), 4.16(2H, s), 4.35–4.40(1H, m), 6.12(1H, d, J=9 Hz), 7.15(1H, t, J=8 Hz), 7.24(2H, t, J=8 Hz), 7.34(2H, d, J=8 Hz), 7.40(1H, d, J=9 Hz)

Example 14

2-[2-Benzyl-6-[(3R,4R)-3-hydroxy-4-methoxypyrrolidin-1-yl]-3-pyridyl]ethynylbicyclo[2.2.1]heptan-2-ol This was synthesized in the same manner as in Example 6 except that 2-benzyl-3-iodo-6-[(3R,4R)-3-hydroxy-4-methoxypyrrolidin-1-yl]pyridine (Production Example 1) and 2-ethynylbicyclo[2.2.1]heptan-2-ol (Production Example 21) were used.

$^1$H-NMR(DMSO-d$_6$) δppm=1.15–1.32(4H, m), 1.41–1.52(1H, m), 1.67 (1H, d, J=9 Hz), 1.88–2.04(2H, m), 2.15–2.18(1H, m), 2.30(1H, d, J=3 Hz), 3.27 (3H, s), 3.28–3.52(4H, m), 3.73(1H, brs), 4.03(2H, s), 4.19(1H, brs), 5.24(1H, brs), 5.42(1H, s), 6.26(1H, d, J=8.4 Hz), 7.14(1H, t, J=7 Hz), 7.23(2H, t, J=7 Hz), 7.32(2H, d, J=7 Hz), 7.38(1H, d, J=8.4 Hz)

Example 15

(3R)-3-[2-Benzyl-4-(2-pyrrolidinon-1-yl)phenyl]ethynyl-3-quinuclidinol

To a mixture of 200 mg of 2-benzyl-4-[2-pyrrolidinon-1-yl]phenyl trifluoromethanesulfonate (Production Example 5), 80 mg of (3R)-3-ethynyl-3-quinuclidinol (Production Example 22), 30 mg of tetrakis(triphenylphosphine)palladium (0), 5 mg of copper (I) iodide and 0.2 ml of triethylamine was added 1 ml of N,N-dimethylformamide, followed by heating under stirring under nitrogen atmosphere in an oil bath at 80° C. for 3 hours. After standing to cool, aqueous ammonia was added to the reaction mixture, which then was extracted with ethyl acetate. The organic layer was washed with brine and dried over anhydrous sodium sulfate. The solvent was removed and the residue was purified by NH-silica gel column chromatography with ethyl acetate, to give 66 mg of the title compound.

$^1$H-NMR(CDCl$_3$) δppm=1.32–1.41(1H, m), 1.50–1.60(1H, m), 1.77–1.87(1H, m), 1.95–2.05(2H, m), 2.09–2.18(2H, m), 2.59(2H, t, J=8 Hz), 2.62–2.91(4H, m), 2.98(1H, dd, J=2, 14 Hz), 3.18(1H, dd, J=2, 14 Hz), 3.80 (2H, t, J=7 Hz), 4.15(2H, s), 7.14–7.21(3H, m), 7.24–7.29 (2H, m), 7.42(1H, d, J=8 Hz), 7.46(1H, d, J=2 Hz), 7.52(1H, dd, J=2, 8 Hz)

Example 16

(3R)-3-[2-Benzyl-4-[(3R,4R)-4-hydroxy-3-methoxy-2-pyrrolidinon-1-yl)phenyl]ethynyl-3-quinuclidinol This was synthesized in the same manner as in Example 15 except that 2-benzyl-4-[(3R,4R)-4-hydroxy-3-methoxy-2-pyrrolidinon-1-yl]phenyl trifluoromethanesulfonate (Production Example 9) was used.

$^1$H-NMR(CDCl$_3$) δppm=1.35–1.90(3H, m), 1.96–2.07(2H, m), 2.65–2.93(4H, m), 3.00(1H, dd, J=2, 14 Hz), 3.19(1H, dd, J=2, 14 Hz), 3.71–3.79(4H, m), 3.82(1H, dd, J=4, 11 Hz), 4.02(1H, d, J=5 Hz), 4.15(2H, s), 4.52–4.58 (1H, m), 7.14–7.22(3H, m), 7.24–7.30(2H, m), 7.44(1H, d, J=8 Hz), 7.47(1H, d, J=2 Hz), 7.54(1H, dd, J=2, 8 Hz)

Example 17

(3R)-3-[2-Benzyl-4-[(3R,4R)-3,4-dimethoxy-2-pyrrolidinon-1yl]phenyl]ethynyl-3-quinuclidinol This was synthesized in the same manner as in Example 15 except that 2-benzyl-4-[(3R,4R)-3,4-dimethoxy-2-pyrrolidinon-1-yl]phenyl trifluoromethanesulfonate (Production Example 8) was used.

$^1$H-NMR(CDCl$_3$) δppm=1.34–1.89(3H, m), 1.95–2.06(2H, m), 2.64–2.92(4H, m), 2.99(1H, dd, J=2, 14 Hz), 3.18(1H, dd, J=2, 14 Hz), 3.48 (3H, s), 3.69 (3H, s), 3.77 (2H, d, J=4 Hz), 4.02 (1H, d, J=5 Hz), 4.12–4.18(3H, m), 7.14–7.22(3H, m), 7.24–7.30(2H, m), 7.43(1H, d, J=8 Hz), 7.46(1H, d, J=2 Hz), 7.53(1H, dd, J=2, 8 Hz)

Example 18

(3R)-3-[2-Benzyl-4-[(3R,4S)-3,4-dimethoxypyrrolidin-1-yl)phenyl]ethynyl-3-quinuclidinol Under ice-cooling, 227 mg of N-iodosuccinimide was added to a mixture of 250 mg of (3R,4S)-1-(3-benzylphenyl)-3,4-dimethoxypyrrolidine (Production Example 11) and 3 ml of N,N-dimethylformamide, followed by stirring at the same temperature for 2 hours. 0.5 ml of a 1 M aqueous solution of sodium thiosulfate was added to the reaction mixture, and then the mixture was extracted with ethyl acetate/water. The organic layer was washed with water and brine, dried over anhydrous magnesium sulfate and then evaporated. The residue was subjected to silica gel column chromatography with 10% ethyl acetate/hexane, to give 340 mg of (3R,4S)-1-(3-benzyl-4-iodophenyl-3,4-dimethoxypyrrolidine.

Then, a mixture of 340 mg of (3R,4S)-1-(3-benzyl-4-iodophenyl-3,4-dimethoxypyrrolidine, 134 mg of (3R)-3-ethynyl-3-quinuclidinol (Production Example 22), 9 mg of tetrakis(triphenylphosphine)palladium (0), 8 mg of copper (I) iodide, 0.22 ml of triethylamine and 0.8 ml of methanol was stirred under nitrogen atmosphere at room temperature for 4 hours. After ethyl acetate and methanol were added to the reaction mixture for dissolution, NH-silica gel was added thereto and the reaction mixture was evaporated. The residue was subjected to column chromatography using NH-silica gel with 50% ethyl acetate/hexane and 0–2.5% methanol/ethyl acetate, to give 220 mg of the title compound.

$^1$H-NMR(CDCl$_3$) δppm=1.31–1.42(1H, m), 1.46–1.57(1H, m), 1.77–1.88(1H, m), 1.93–2.06(2H, m), 2.62–2.91(4H, m), 2.96(1H, dd, J=2, 14 Hz), 3.16(1H, dd, J=2, 14 Hz), 3.37(2H, dd, J=4, 10 Hz), 3.42–3.51(8H, m), 3.96–4.03(2H, m), 4.09(2H, s), 6.30(1H, d, J=2 Hz), 6.35(1H, dd, J=2, 8 Hz), 7.14–7.33(6H, m)

Example 19

(3R)-3-[2-Benzyl-4-[(3R,4S)-3,4-dihydroxypyrrolidin-1-yl]phenyl]ethynyl-3-quinuclidinol This was synthesized in the same manner as in Example 18 except that (3R,4S)-1-(3-benzylphenyl)-3,4-dihydroxypyrrolidine (Production Example 10) was used.

$^1$H-NMR(DMSO-d$_6$) δppm=1.20–1.30(1H, m), 1.38–1.50(1H, m), 1.65–1.76(1H, m), 1.82–1.92(2H, m), 2.44–2.70(4H, m), 2.77(1H, d, J=14 Hz), 2.94(1H, d, J=14 Hz), 3.05(2H, dd, J=4, 10 Hz), 3.36(2H, dd, J=6, 10 Hz), 4.01(2H, s), 4.07–4.15(2H, m), 4.91(2H, d, J=5 Hz), 5.45 (1H, s), 6.31(1H, dd, J=2, 8 Hz), 6.35(1H, d, J=2 Hz), 7.12–7.28(6H, m)

Example 20

(3R)-3-[2-Benzyl-4-[cis-3-hydroxy-4-methoxypyrrolidin-1-yl]phenyl]ethynyl-3-quinuclidinol This was synthesized in the same manner as in Example 18 except that 1-(3-benzylphenyl)-cis-3-hydroxy-4-methoxypyrrolidine (Production Example 12) was used.

$^1$H-NMR(CDCl$_3$) δppm=1.32–2.06(5H, m), 2.60–2.91(4H, m), 2.97(1H, d, J=14 Hz), 3.17(1H, dd, J=2, 14 Hz), 3.25–3.36(2H, m), 3.45–3.54(5H, m), 3.95(1H, q, J=5 Hz), 4.09(2H, s), 4.41(1H, br.s), 6.29(1H, d, J=3 Hz), 6.34(1H, dd, J=3, 8 Hz), 7.14–7.33(6H, m)

Example 21

(3R)-3-[2-Benzyl-4-[trans-3-hydroxy-4-methoxypyrrolidin-1-yl]phenyl]ethynyl-3-quinuclidinol To a mixture of 460 mg of 1-(3-bromophenyl)-trans-3-hydroxy-4-methoxypyrrolidine (Production Example 13), 46 mg of 1,3-bis(diphenylphosphino)propanenickel (II) chloride and 5 ml of tetrahydrofuran was added dropwise 2.5 ml of a 2.0 M tetrahydrofuran solution of benzyl magnesium chloride while stirring at room temperature, followed by stirring for 3 hours. The reaction mixture was separated with a saturated aqueous ammonium chloride solution-ethyl acetate, and the organic layer was washed with water and brine, dried over anhydrous magnesium sulfate and then evaporated. The residue was subjected to silica gel column chromatography with 10–30% ethyl acetate/hexane. Subsequently, the resulting compound was subjected to the same operations as those in Example 18 to synthesize the title compound.

$^1$H-NMR(CDCl$_3$) δppm=1.31–1.88(3H, m), 1.93–2.07(2H, m), 2.62–2.91(4H, m), 2.97(1H, dd, J=2, 14 Hz), 3.16(1H, dd, J=2, 14 Hz), 3.21–3.29(2H, m), 3.41(3H, s), 3.54–3.63(2H, m), 3.83–3.88(1H, m), 4.09(2H, s), 4.37–4.42(1H, m), 6.32(1H, d, J=2 Hz), 6.37(1H, dd, J=2, 8 Hz), 7.14–7.32(6H, m)

Example 22

3-[4-[2-Benzyl-6-[(3R,4R)-3-hydroxy-4-methoxypyrrolidin-1-yl]-3-pyridyl]phenyl]-3-quinuclidinol To a mixture of 280 mg of 2-(4-bromophenyl)-6-methyl-1,3,6,2-dioxazaborocane (Production Example 14) and 10 ml of tetrahydrofuran was added dropwise 2 ml of a 1 M cyclohexane-hexane solution of sec-butyllithium under nitrogen atmosphere while cooling in a liquid nitrogen-tetrahydrofuran bath at −90° C., followed by stirring as it was for 40 minutes. Then, a solution of 130 mg of 3-quinuclidinone in 1 ml of tetrahydrofuran was added to the mixture, the liquid nitrogen-tetrahydrofuran bath was removed and the mixture was stirred at room temperature for 30 minutes. 1 ml of an aqueous ammonium chloride solution was added to the reaction mixture, followed by evaporating. To the residue were added 5 ml of methanol, 2 ml of a 5 M aqueous solution of potassium carbonate, 220 mg of 2-benzyl-3-iodo-6-[(3R,4R)-3-hydroxy-4-methoxypyrrolidin-1-yl]pyridine hydrochloride and 5 ml of diethoxymethane, followed by heating under stirring under nitrogen atmosphere in an oil bath at 60° C. for 3 hours. The reaction mixture was extracted with ethyl acetate-water, and the organic layer was washed with water and brine, dried over anhydrous magnesium sulfate and then evaporated. The residue was subjected to column chromatography using NH-silica gel with 50% ethyl acetate-hexane and 0–5% methanol-ethyl acetate, to give 60 mg of the title compound.

$^1$H-NMR(DMSO-d$_6$) δppm=1.22–1.46(3H, m), 1.92–1.97(1H, m), 2.08–2.18(1H, m), 2.58–2.92(6H, m), 3.30(3H, s), 3.31–3.57(4H, m), 3.73–3.78(1H, m), 3.92(2H, s), 4.19–4.13(1H, m), 5.13(1H, s), 5.23(1H, d, J=4 Hz), 6.37(1H, d, J=8 Hz), 7.05–7.23(7H, m), 7.36(1H, d, J=8 Hz), 7.53(2H, d, J=8 Hz)

Example 23

(E)-3-[2-[2-Benzyl-6-(2-pyrrolidinon-1-yl)pyridin-3-yloxy]-1-fluoroethynylidene]quinuclidine 70 mg of 2-benzyl-3-hydroxy-6-(2-pyrrolidinon-1-yl)pyridine (Production Example 6), 50 mg of borane-[(E)-3-(2-chloro-1-fluoroethynylidene)quinuclidine] complex (synthesized by the method described in WO96/26938 A) and 70 mg of anhydrous potassium carbonate were suspended in 1 ml of N,N-dimethylformamide, followed by stirring at room temperature overnight. Subsequently, water was slowly added to the mixture until precipitates were formed, and the resulting solid was collected by filtration. The solid was dissolved in 2 ml of acetone and 0.3 ml of 5 N hydrochloric acid was added dropwise thereto in an ice bath. After the temperature was returned to room temperature and stirring was continued for 1 hour, 10 ml of 1 N hydrochloric acid was added to the reaction mixture and the aqueous layer was washed with t-butyl methyl ether. Subsequently, anhydrous potassium carbonate was added to the aqueous layer to make it weakly basic, and it was extracted with ethyl acetate. The organic layer was washed with brine, dried over anhydrous magnesium sulfate and the solvent was evaporated, to give 70 mg of the title compound.

$^1$H-NMR(CDCl$_3$) δppm=1.56–1.73(4H,m), 2.05–2.14(2H,m), 2.63(2H, t, J=8 Hz), 2.75–2.96(4H, m), 3.00(1H, t, J=3 Hz), 3.34(2H, d, J=3 Hz), 4.07(2H, t, J=7 Hz), 4.11(2H, s), 4.42(2H, d, J=20 Hz) 7.14–7.32(6H, m), 8.17(1H, d, J=9 Hz)

Example 24

1-[2-Benzyl-6-(3,3-ethylenedioxypyrrolidin-1-yl]-3-pyridyl]ethynylcyclohexylamine This was synthesized in the same manner as in Example 6 except that 2-benzyl-3-iodo-6-(3,3-ethylenedioxypyrrolidin-1-yl)pyridine (Production Example 24) was used.

$^1$H-NMR(CDCl$_3$) δppm=1.09–1.91(10H, m), 2.17(2H, t, J=7 Hz), 3.54(2H, s), 3.59(2H, t, J=7 Hz), 4.01(4H, s), 4.17(2H, s), 6.12(1H, d, J=9 Hz), 7.12–7.37(5H, m), 7.41 (1H, d, J=9 Hz)

Example 25

1-[2-Benzyl-6-(4-methoxypiperidino)-3-pyridyl]ethynylcyclohexylamine

This was synthesized in the same manner as in Example 6 except that 2-benzyl-3-iodo-6-(4-methoxypiperidino)pyridine (Production Example 25) was used.

$^1$H-NMR(CDCl$_3$) δppm=1.09–1.96 (14H, m), 3.16–3.23 (2H, m),3.37 (3H, s), 3.37–3.46(1H, m), 3.96–4.03(2H, m), 4.17(2H, s), 6.44(1H, d, J=9 Hz), 7.16(1H, t, J=7 Hz), 7.24(2H, t, J=7 Hz), 7.33(2H, d, J=7 Hz), 7.42(1H, d ,J=9 Hz)

Example 26

4-[2-Benzyl-6-[(3R,4R)-3,4-dimethoxypyrrolidin-1-yl]-3-pyridyl]ethynyl-exo-1-azaadamantan-4-ol (A) and 4-[2-Benzyl-6-[(3R,4R)-3,4-dimethoxypyrrolidin-1-yl]-3-pyridyl]ethynyl-endo-1-azaadamantan-4-ol (B)

These compounds were synthesized in the same manner as in Example 15 except that 2-benzyl-3-iodo-6-[(3R,4R)-3,4-dimethoxypyrrolidin-1-yl]pyridine (Production Example 26) and 4-ethynyl-1-azaadamantan-4-ol (Production Example 23) were used. The compounds (A) and (B) were separated and purified by NH-silica gel column chromatography with ethyl acetate and 10% methanol/ethyl acetate as an elution solvent.

Compound A: $^1$H-NMR (CDCl$_3$) δppm=1.55(1H, brs), 1.79(2H, d, J=12 Hz), 1.85(2H, brs), 2.37(2H, d, J=12 Hz), 3.07(2H, brs), 3.16(2H, d, J=13 Hz), 3.37(2H, d, J=13 Hz), 3.41(6H, s), 3.53–3.67(4H, m), 3.91–3.95(2H, m), 4.15(2H, s), 6.14(1H, d, J=9 Hz), 7.15(1H, t, J=8 Hz), 7.24(2H, t, J=8 Hz), 7.30(2H, d, J=8 Hz), 7.40(1H, d, J=9 Hz)

Compound B: $^1$H-NMR (CDCl$_3$) δppm=1.56–1.63(1H, m), 1.82(2H, brs), 1.97(2H, d, J=13 Hz), 2.26 (2H, d, J=13 Hz), 2.97 (2H, d, J=13 Hz), 3.09(2H, brs), 3.41(6H, s), 3.53–3.67(6H, m), 3.91–3.95(2H, m), 4.17(2H, s), 6.16(1H, d, J=8 Hz), 7.16(1H, t, J=7 Hz), 7.24(2H, t, J=7 Hz), 7.31(2H, d, J=7 Hz), 7.40(1H, d, J=8 Hz)

TABLE 3

Example 1

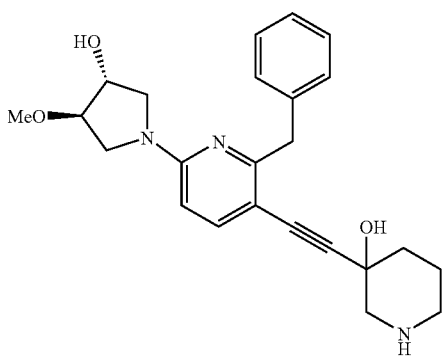

Example 2

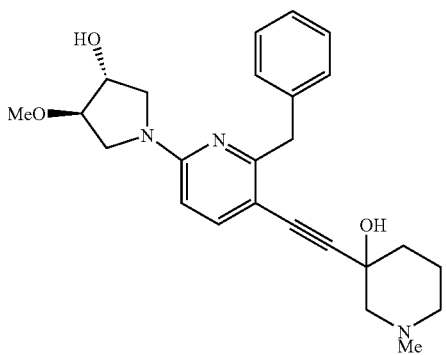

Example 3

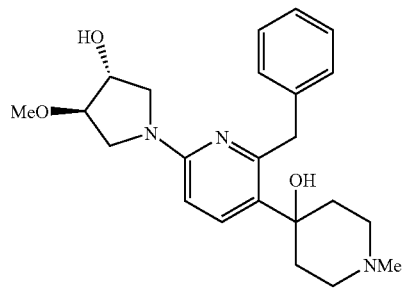

Example 4

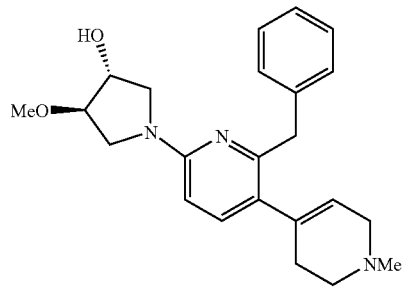

TABLE 3-continued
Example 5
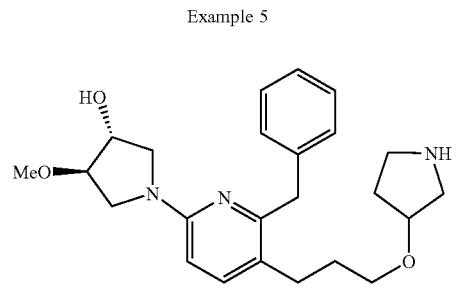
Example 6
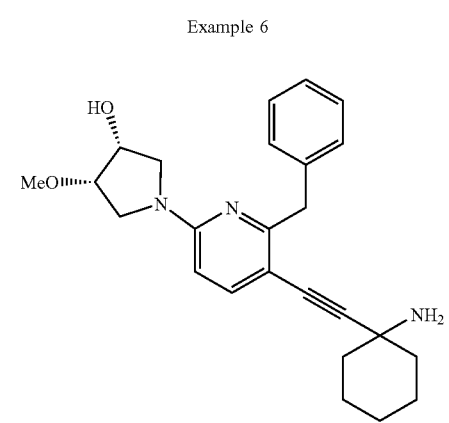
Example 7
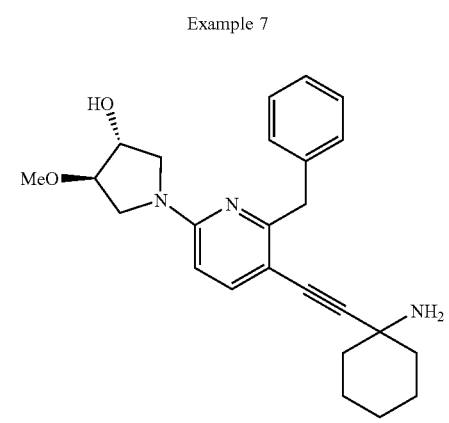
Example 8
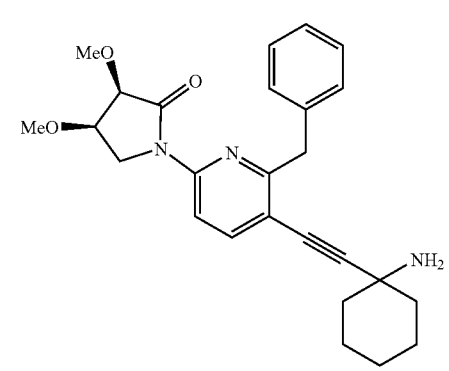
TABLE 3-continued
Example 9
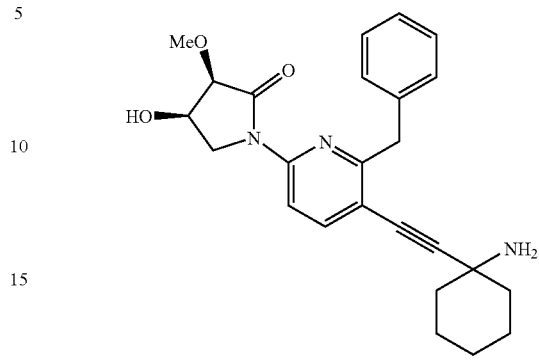
Example 10
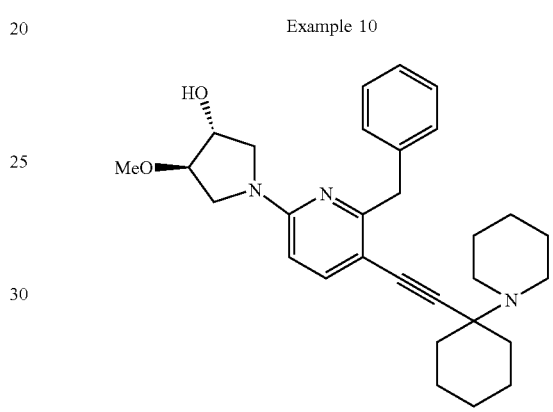
Example 11
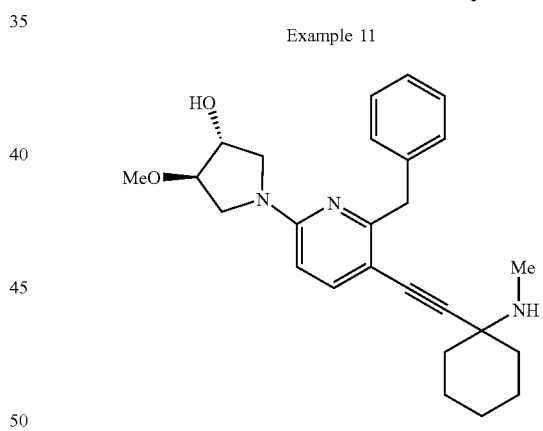
Example 12
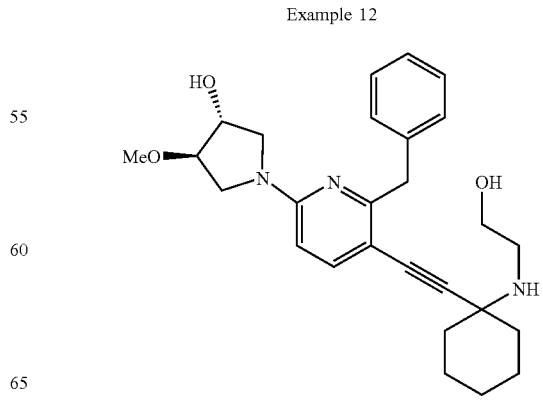

TABLE 3-continued
Example 13
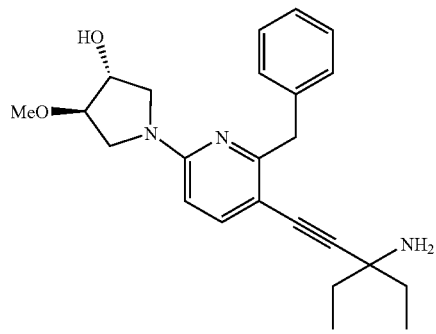
Example 14
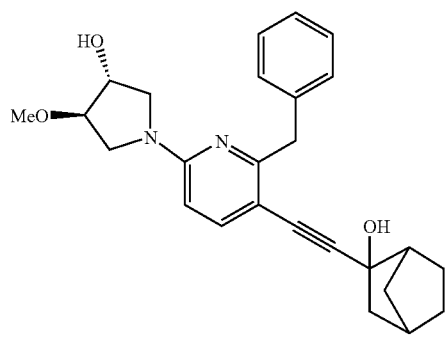
Example 15
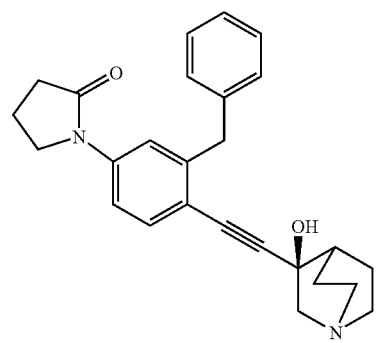
Example 16
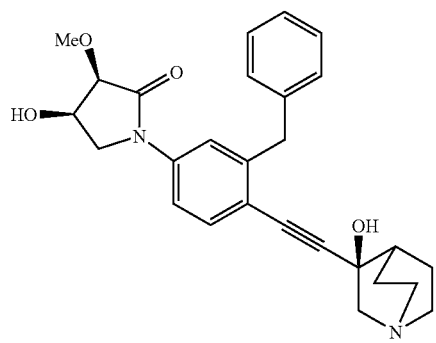
TABLE 3-continued
Example 17
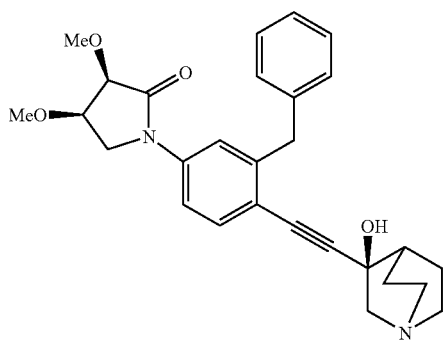
Example 18
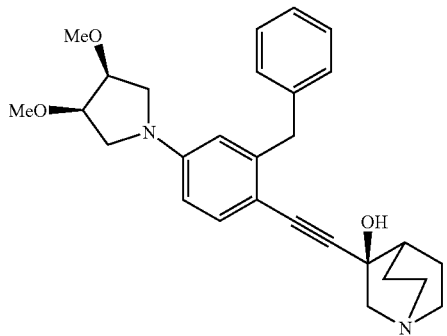
Example 19
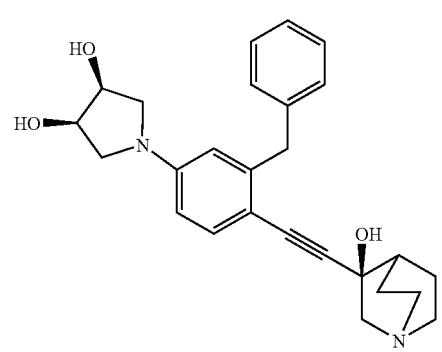
Example 20
cis
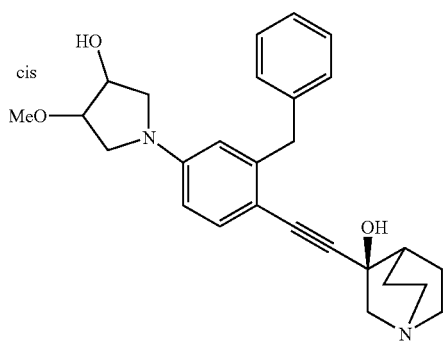

TABLE 3-continued
Example 21
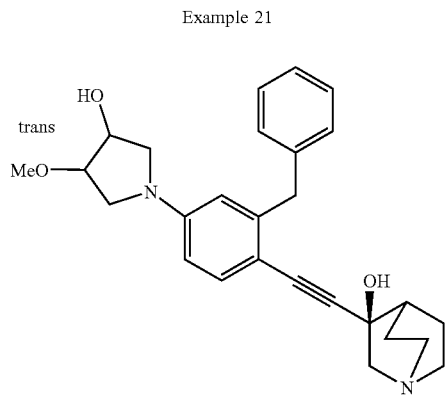
Example 22
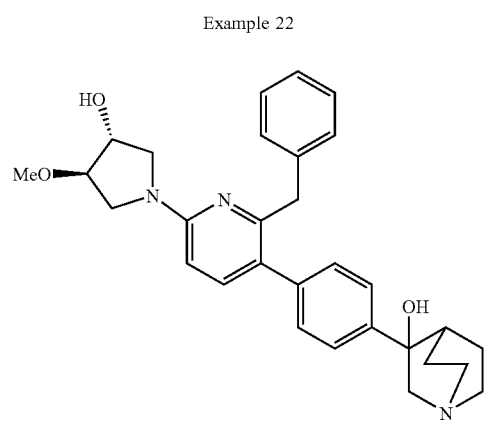
Example 23
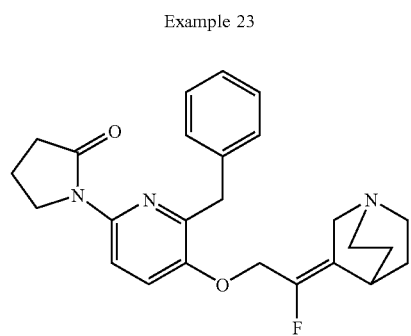
Example 24
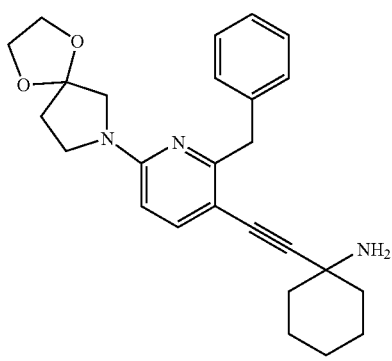
TABLE 3-continued
Example 25
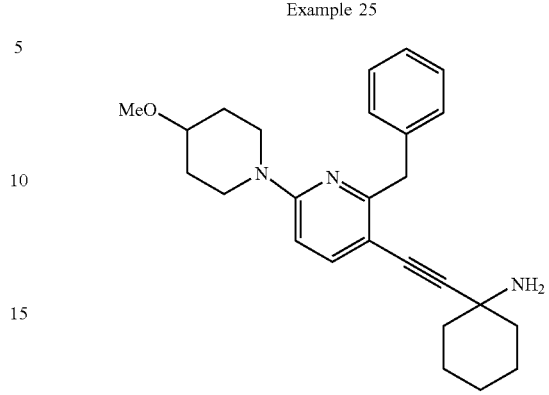
Example 26(A)
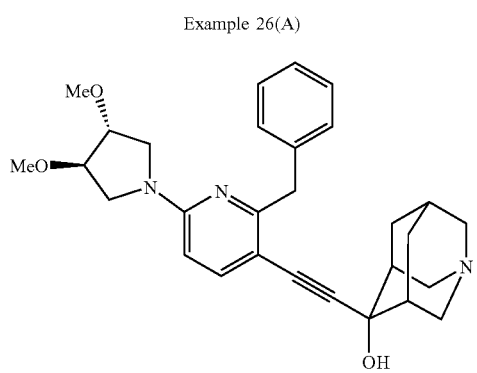
Example 26(B)
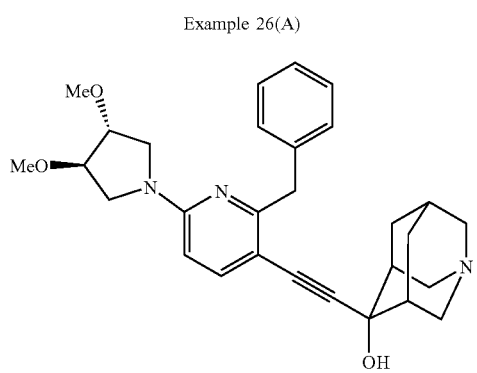
The invention claimed is:
1. A compound (I) represented by the formula:
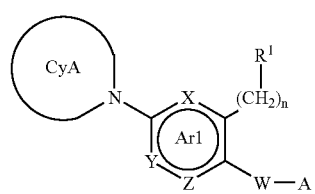
(I)
wherein $R^1$ represents an optionally substituted vinyl group or an aromatic ring which may be substituted; n is an integer of 0 to 2;

X, Y, and Z are the same as or different from each other and each represents an optionally substituted carbon atom, or an optionally substituted nitrogen atom;
CyA represents pyrrolidine or piperidine;
W represents a chain expressed by
(1) optionally substituted —CH$_2$—CH$_2$—,
(2) optionally substituted —CH═CH—,
(3) —C≡C—,
(4) an optionally substituted phenylene group,
(5) a single bond,
(6) —NH—CO—,
(7) —CO—NH—,
(8) —NH—CH$_2$—,
(9) —CH$_2$—NH—,
(10) —CH$_2$—CO—,
(11) —CO—CH$_2$—,
(12) —O—(CH$_2$)$_m$—,
(13) —(CH$_2$)$_m$—O—, wherein (m represents an integer of 0 to 5,
(14) —O—CH$_2$—CR$^2$═,
(15) —O—CH$_2$—CHR$^2$—, wherein R$^2$ represents a hydrogen atom, a C$_{1-6}$ alkyl group, or a halogen atom,
(16) —NH—S(O)$_l$—,
(17) —S(O)$_l$—NH—,
(18) —CH$_2$—S(O)$_l$— or
(19) —S(O)$_l$—CH$_2$—, wherein l represents 0, 1, or 2; and
A represents a group having any of the following structural formulae:

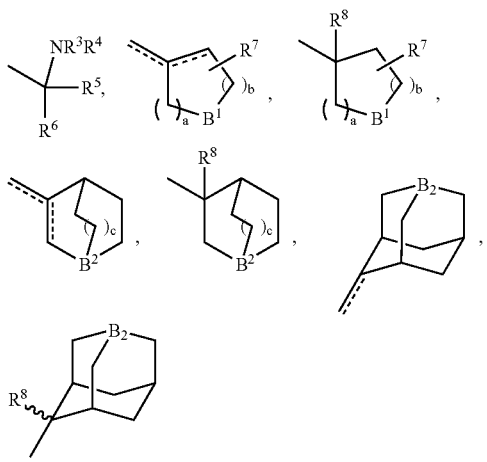

wherein R$^3$ and R$^4$ are independent of each other and each represents a hydrogen atom or an optionally substituted C$_{1-6}$ alkyl group;
R$^5$ and R$^6$ are independent of each other and each represents a hydrogen atom or an optionally substituted C$_{1-6}$ alkyl group;
R$^7$ represents a hydrogen atom, an optionally substituted C$_{1-6}$ alkyl group, a hydroxyl group, an alkoxy group, a halogen atom or an optionally substituted amino group;
R$^8$ represents a hydrogen atom, a hydroxyl group, an alkoxy group, a halogen atom or an optionally substituted amino group,
B$^1$ represents an optionally substituted carbon atom, or an optionally substituted nitrogen atom;
B$^2$ represents an optionally substituted carbon atom or nitrogen atom;

a and b represent an integer of 0 to 4, provided that a+b is an integer of 0 to 4,
c represents 0 or 1; and ----- represents a single bond or a double bond, provided that when c is 1 in which A is a quinuclidine having R$^8$ represented by

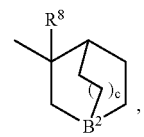

the case where R$^8$ is a hydrogen atom or a hydroxyl group;
Arl is an aromatic heterocycle selected from the group consisting of pyridine, pyrimidine, pyrazine, pyridazine and triazine thereof;
and W is one of (1) to (3), (6) to (11) and (16) to (19) are excluded, a salt thereof or a hydrate thereof.

2. The compound according to claim 1, a salt thereof or a hydrate thereof, wherein R$^1$ represents an optionally substituted vinyl group, a benzene ring which may be substituted or a thiophene ring which may be substituted;
n is an integer of 0 to 2;
Arl represents a benzene ring, pyridine ring, pyrimidine ring, pyrazine ring, pyridazine ring, triazine ring, each of which may be substituted with a lower alkyl group, a halogen atom or an alkoxy group;
CyA represents pyrrolidine ring or piperidine ring, each of which may be substituted with one to three groups which are the same as or different from each other selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group;
W represents a chain expressed by
(1) optionally substituted —CH$_2$—CH$_2$—,
(2) optionally substituted —CH═CH—,
(3) —C≡C—,
(4) an optionally substituted phenylene group,
(5) a single bond,
(6) —NH—CO—,
(7) —CO—NH—,
(8) —NH—CH$_2$—,
(9) —CH$_2$—NH—,
(10) —CH$_2$—CO—,
(11) —CO—CH$_2$—,
(12) —O—(CH$_2$)$_m$—,
(13) (CH$_2$)$_m$—O—, wherein m represents an integer of 0 to 5,
(14) —O—CH$_2$—CR$^2$═,

(15) —O—CH$_2$—CHR$^2$—, wherein R$^2$ represents a hydrogen atom, a C$_{1-6}$ alkyl group, or a halogen atom,
(16) —NH—S(O)$_1$—,
(17) —S(O)$_1$—NH—,
(18) —CH$_2$—S(O)$_1$— or
(19) —S(O)$_1$—CH$_2$—, wherein 1 represents 0, 1, or 2; and A represents a group having any of the following structural formulae:

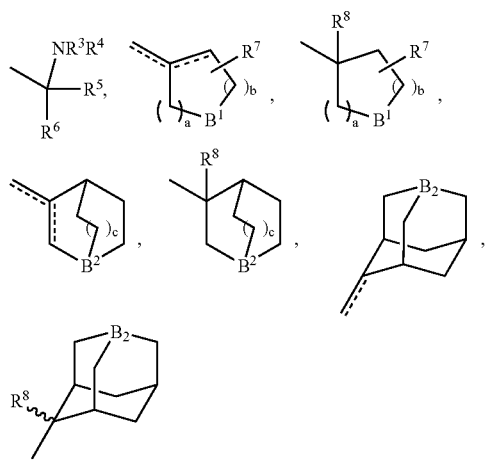

wherein R$^3$ and R$^4$ are independent of each other and each represents a hydrogen atom or an optionally substituted C$_{1-6}$ alkyl group;
R$^5$ and R$^6$ are independent of each other and each represents a hydrogen atom or an optionally substituted C$_{1-6}$ alkyl group;
R$^7$ represents a hydrogen atom, an optionally substituted C$_{1-6}$ alkyl group, a hydroxyl group, an alkoxy group, a halogen atom or an optionally substituted amino group;
R$^8$ represents a hydrogen atom, a hydroxyl group, an alkoxy group, a halogen atom or an optionally substituted amino group,
B$^1$ represents an optionally substituted carbon atom, or an optionally substituted nitrogen atom;
B$^2$ represents an optionally substituted carbon atom or nitrogen atom;
a and b represent an integer of 0 to 4, provided that a+b is an integer of 0 to 4,
c represents 0 or 1; and ------- represents a single bond or a double bond, provided that when c is 1 in which A is a quinuclidine having R$^8$ represented by

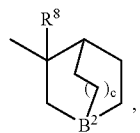

the case where R$^8$ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded.

3. The compound according to claim 1, a salt thereof or a hydrate thereof, wherein Arl represents a benzene ring, pyridine ring, pynimidine ring or thiazole ring optionally substituted with a lower alkyl group, a halogen atom or an alkoxy group;
R$^1$ represents an optionally substituted vinyl group, a benzene ring which may be substituted or a thiophene ring which may be substituted;
n is an integer of 0 to 2;
CyA represents pyrrolidine ring or piperidine ring, each of which may be substituted with one to three groups which are the same as or different from each other selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group;
W represents a chain expressed by
(1) optionally substituted —CH$_2$—CH$_2$—,
(2) optionally substituted —CH=CH—,
(3) —C≡C—,
(4) an optionally substituted phenylene group,
(5) a single bond,
(6) —NH—CO—,
(7) —CO—NH—,
(8) —NH—CH$_2$—,
(9) —CH$_2$—NH—,
(10) —CH$_2$—CO—,
(11) —CO—CH$_2$—,
(12) —O—(CH$_2$)$_m$—,
(13) —(CH$_2$)$_m$—O—, wherein m represents an integer of 0 to 5,
(14) —O—CH$_2$—CR =,
(15) —O—CH$_2$—CHR$^2$—, wherein R$^2$ represents a hydrogen atom, a C$_{1-6}$ alkyl group, or a halogen atom,
(16) —NH—S(O)$_1$—,
(17) —S(O)$_1$—NH—,
(18) —CH$_2$—S(O)$_1$— or
(19) —S(O)$_1$—CH$_2$—, wherein 1 represents 0, 1, or 2; and A represents a group having any of the following structural formulae:

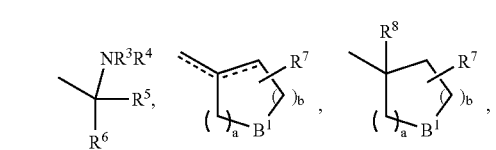

-continued

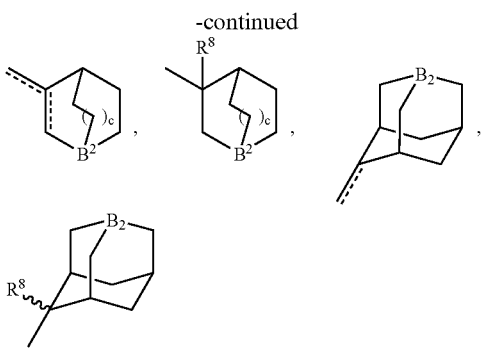

wherein $R^3$ and $R^4$ are independent of each other and each represents a hydrogen atom or an optionally substituted $C_{1-6}$ alkyl group;
$R^5$ and $R^6$ are independent of each other and each represents a hydrogen atom or an optionally substituted $C_{1-6}$ alkyl group;
$R^7$ represents a hydrogen atom, an optionally substituted $C_{1-6}$ alkyl group, a hydroxyl group, an alkoxy group, a halogen atom or an optionally substituted amino group;
$R^8$ represents a hydrogen atom, a hydroxyl group, an alkoxy group, a halogen atom or an optionally substituted amino group,
$B^1$ represents an optionally substituted carbon atom, or an optionally substituted nitrogen atom;
$B^2$ represents an optionally substituted carbon atom or nitrogen atom;
a and b represent an integer of 0 to 4, provided that a+b is an integer of 0 to 4,
c represents 0 or 1; and ------ represents a single bond or a double bond, provided that when c is 1 in which A is a quinuclidine having $R^8$ represented by

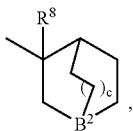

the case where $R^8$ is a hydrogen atom or a hydroxyl group;
Arl is an aromatic heterocycle selected from the group consisting of pyridine, pyrimidine, pyrazine, pyridazine and triazine thereof; and W is one of(1) to (3), (6) to (11) and (16) to (19) are excluded.

4. The compound according to claim 1, a salt thereof or a hydrate thereof, wherein W represents a chain expressed by
(1) optionally substituted —$CH_2$—$CH_2$—,
(2) optionally substituted —CH═CH—,
(3) —C≡C—,
(4) an optionally substituted phenylene group,
(5) a single bond,
(13) —$(CH_2)_m$—O— (where m represents an integer of 0 to 5),
(14) —O—$CH_2$—$CR^2$═, or
(15) —O—$CH_2$—$CHR^2$—, wherein $R^2$ represents a hydrogen atom, an alkyl group or a halogen atom;
$R^1$ represents an optionally substituted vinyl group, a benzene ring which may be substituted or a thiophene ring which may be substituted;
n is an integer of 0 to 2;

Arl represents a benzene ring, pyridine ring, pyrimidine ring, pyrazine ring, pyridazine ring, triazine ring, each of which may be substituted with a lower alkyl group, a halogen atom or an alkoxy group;
CyA represents pyrrolidine ring or pipenidine ring, each of which may be substituted with one to three groups which are the same as or different from each other selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group,
(17) an alkoxycarbonyloxy group; and
A represents a group having any of the following structural formulae:

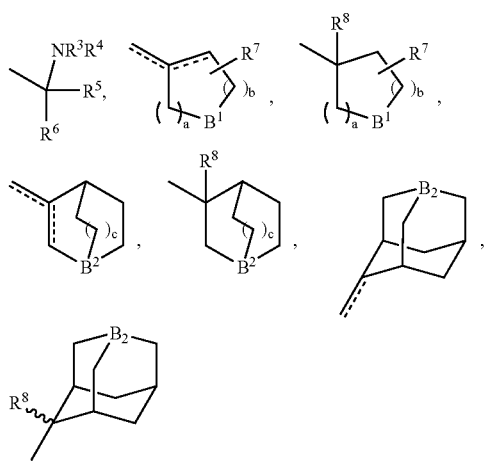

wherein $R^3$ and $R^4$ are independent of each other and each represents a hydrogen atom or an optionally substituted $C_{1-6}$ alkyl group;
$R^5$ and $R^6$ are independent of each other and each represents a hydrogen atom or an optionally substituted $C_{1-6}$ alkyl group;
$R^7$ represents a hydrogen atom, an optionally substituted $C_{1-6}$ alkyl group, a hydroxyl group, an alkoxy group, a halogen atom or an optionally substituted amino group;
$R^8$ represents a hydrogen atom, a hydroxyl group, an alkoxy group, a halogen atom or an optionally substituted amino group,
$B^1$ represents an optionally substituted carbon atom, or an optionally substituted nitrogen atom;
$B^2$ represents an optionally substituted carbon atom or nitrogen atom;
a and b represent an integer of 0 to 4, provided that a+b is an integer of 0 to 4, c represents 0 or 1; and ------- represents a single bond or a double bond, provided that when c is 1 in which A is a quinuclidine having $R^8$ represented by

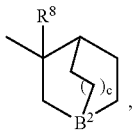

the case where $R^8$ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded.

5. The compound according to claim 1, a salt thereof or a hydrate thereof, wherein Arl represents a benzene ring, pyridine ring, pyrimidine ring or thiazole ring, each of which may be substituted with a lower alkyl group, a halogen atom or an alkoxy group;

W represents a chain expressed by
(1) optionally substituted —$CH_2$—$CH_2$—,
(2) optionally substituted —CH═CH—,
(3) —C≡C—,
(4) an optionally substituted phenylene group,
(5) a single bond,
(13) —$(CH_2)_m$—O— (where m represents an integer of 0 to 5),
(14) —O—$CH_2$—$CR^2$═, or
(15) —O—$CH_2$—$CHR^2$—, wherein $R^2$ represents a hydrogen atom, an alkyl group or a halogen atom;
$R^1$ represents an optionally substituted vinyl group, a benzene ring which may be substituted or a thiophene ring which may be substituted;
n is an integer of 0 to 2;
CyA represents pyrrolidine ring or piperidine ring, each of which may be substituted with one to three groups which are the same as or different from each other and selected from:
(1) a lower alkyl group which may be substituted,
(2) a lower alkenyl group which may be substituted,
(3) a lower alkynyl group which may be substituted,
(4) a lower alkoxy group which may be substituted,
(5) an oxo group,
(6) a nitrile group,
(7) an alkylenedioxy group,
(8) a hydroxyl group,
(9) a halogen atom,
(10) an amino group which may be substituted,
(11) an acylamino group,
(12) a carbamoyl group which may be substituted,
(13) a carbamoyloxy group which may be substituted,
(14) a carboxyl group,
(15) an acyl group,
(16) an acyloxy group, and
(17) an alkoxycarbonyloxy group; and
A represents a group having any of the following structural formulae:

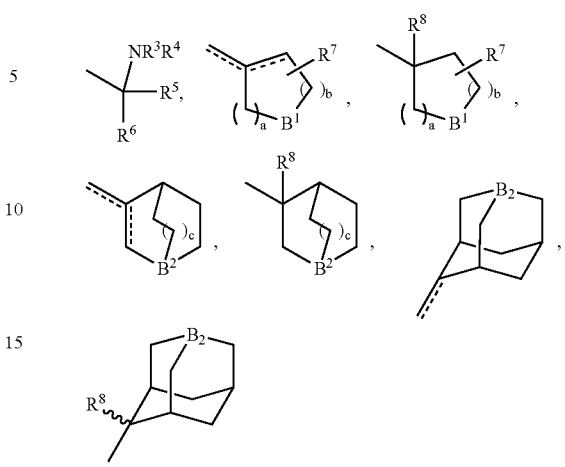

wherein $R^3$ and $R^4$ are independent of each other and each represents a hydrogen atom or an optionally substituted $C_{1-6}$ alkyl group;
$R^5$ and $R^6$ are independent of each other and each represents a hydrogen atom or an optionally substituted $C_{1-6}$ alkyl group;
$R^7$ represents a hydrogen atom, an optionally substituted $C_{1-6}$ alkyl group, a hydroxyl group, an alkoxy group, a halogen atom or an optionally substituted amino group;
$R^8$ represents a hydrogen atom, a hydroxyl group, an alkoxy group, a halogen atom or an optionally substituted amino group,
$B^1$ represents an optionally substituted carbon atom, or an optionally substituted nitrogen atom;
$B^2$ represents an optionally substituted carbon atom or nitrogen atom;
a and b represent an integer of 0 to 4, provided that a+b is an integer of 0 to 4,
c represents 0 or 1; and ------- represents a single bond or a double bond, provided that when c is 1 in which A is a quinuclidine having $R^8$ represented by

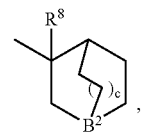

the case where $R^8$ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded.

6. The compound according to claim 1, a salt thereof or a hydrate thereof, wherein Arl represents a benzene ring, pyridine ring, or pyrimidine ring, each of which may be substituted with a lower alkyl group, a halogen atom or an alkoxy group;

W represents a chain expressed by
(1) optionally substituted —$CH_2$—$CH_2$—,
(2) optionally substituted —CH═CH—,
(3) —C≡C—,
(4) an optionally substituted phenylene group,
(5) a single bond,

(13) —(CH$_2$)$_m$—O—, wherein m represents an integer of 0 to 5,

(14) —O—CH$_2$—CR$^2$=, or

(15) —O—CH$_2$—CHR$^2$—, wherein R$^2$ represents a hydrogen atom, an alkyl group or a halogen atom;

CyA represents pyrrolidine ring or piperidine ring, each of which may be substituted with one to three groups which are the same as or different from each other selected from:

(1) a lower alkyl group which may be substituted, (4) a lower alkoxy group which may be substituted, (5) an oxo group, (7) an alkylenedioxy group, (8) a hydroxyl group, and (9) a halogen atom;

R$^1$ represents an optionally substituted vinyl group, a benzene ring which may be substituted or a thiophene ring which may be substituted;

n is an integer of 0 to 2; and

A represents a group having any of the following structural formulae:

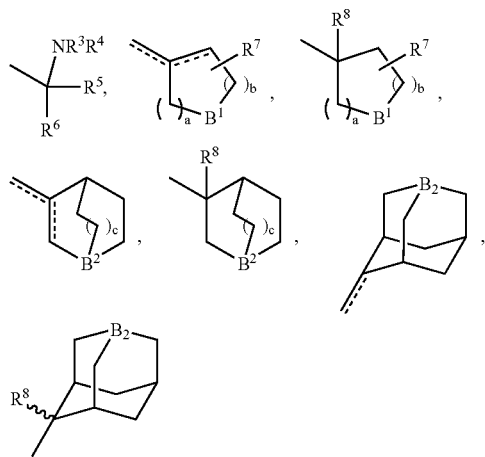

wherein R$^3$ and R$^4$ are independent of each other and each represents a hydrogen atom or an optionally substituted C$_{1-6}$ alkyl group;

R$^5$ and R$^6$ are independent of each other and each represents a hydrogen atom or an optionally substituted C$_{1-6}$ alkyl group;

R$^7$ represents a hydrogen atom, an optionally substituted C$_{1-6}$ alkyl group, a hydroxyl group, an alkoxy group, a halogen atom or an optionally substituted amino group;

R$^8$ represents a hydrogen atom, a hydroxyl group, an alkoxy group, a halogen atom or an optionally substituted amino group, B$^1$ represents an optionally substituted carbon atom, or an optionally substituted nitrogen atom;

B$^2$ represents an optionally substituted carbon atom or nitrogen atom;

a and b represent an integer of 0 to 4, provided that a+b is an integer of 0 to 4, c represents 0 or 1; and ------- represents a single bond or a double bond, provided that when c is 1 in which A is a quinuclidine having R$^8$ represented by

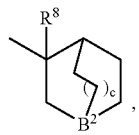

the case where R$^8$ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded.

7. The compound according to claim 1, a salt thereof or a hydrate thereof, wherein Arl represents a benzene ring, pyridine ring, or pyrimidine ring, each of which may be substituted with a lower alkyl group, a halogen atom or an alkoxy group;

W represents a chain expressed by (1) optionally substituted —CH$_2$—CH$_2$—, (2) optionally substituted —CH=CH—, (3) —C≡C—, (4) an optionally substituted phenylene group, (5) a single bond,

(13) —(CH$_2$)$_m$—O—, wherein m represents an integer of 0 to 5,

(14) —O—CH$_2$—CR$^2$=, or

(15) —O—CH$_2$—CHR$^2$—, wherein R$^2$ represents a hydrogen atom, an alkyl group or a halogen atom;

CyA represents pyrrolidine ring or piperidine ring, each of which may be substituted with one to three groups which are the same as or different from each other and selected from:

(1) a lower alkyl group which may be substituted, (4) a lower alkoxy group which may be substituted, (5) an oxo group, (7) an alkylenedioxy group, (8) a hydroxyl group, and (9) a halogen atom;

R$^1$ represents a benzene ring which may be substituted;

n is an integer of 0 to 2; and

A represents a group having any of the following structural formulae:

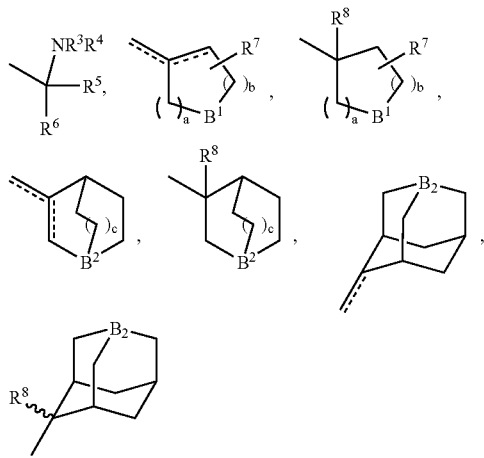

wherein R³ and R⁴ are independent of each other and each represents a hydrogen atom or an optionally substituted $C_{1-6}$ alkyl group;

R⁵ and R⁶ are independent of each other and each represents a hydrogen atom or an optionally substituted $C_{1-6}$ alkyl group;

R⁷ represents a hydrogen atom, an optionally substituted $C_{1-6}$ alkyl group, a hydroxyl group, an alkoxy group, a halogen atom or an optionally substituted amino group;

R⁸ represents a hydrogen atom, a hydroxyl group, an alkoxy group, a halogen atom or an optionally substituted amino group, B¹ represents an optionally substituted carbon atom, or an optionally substituted nitrogen atom;

B² represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having R⁸ represented by

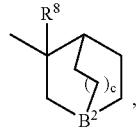

the case where R⁸ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded.

8. A compound selected from the group consisting of:
3-[2-benzyl-6-[(3R,4R)-3-hydroxy-4-methoxypyrrolidin-1-yl]-3-pyridyl]ethynyl-3-piperidinol;
3-[2-benzyl-6-[(3R,4R)-3-hydroxy-4-methoxypyrrolidin-1-yl]-3-pyridyl]ethynyl-1-methyl-3-piperidinol;
4-[2-benzyl-6-[(3R,4R)-3-hydroxy-4-methoxypyrrolidin-1-yl]-3-pyridyl]-1-methyl-4-piperidinol;
4-[2-benzyl-6-[(3R,4R)-3-hydroxy-4-methoxypyrrolidin-1-yl]-3-pyridyl]-1-methyl-1,2,3,6-tetrahydropyridine;
3-[3-[2-benzyl-6-[(3R,4R)-3-hydroxy-4-methoxypyrrolidin-1-yl]-3-pyridyl]propyloxy]pyrrolidine;
1-[2-benzyl-6-[(3R,4S)-3-hydroxy-4-methoxypyrrolidin-1-yl]-3-pyridyl]ethynylcyclohexylamine;
1-[2-benzyl-6-[(3R,4R)-3-hydroxy-4-methoxypyrrolidin-1-yl]-3-pyridyl]ethynylcyclohexylamine;
1-[2-benzyl-6-[(3R,4R)-3,4-dimethoxy-2-pyrrolidinon-1-yl]-3-pyridyl]ethynylcyclohexylamine;
1-[2-benzyl-6-[(3R,4R)-4-hydroxy-3-methoxy-2-pyrrolidinon-1-yl]-3-pyridyl]ethynylcyclohexylamine;
1-[1-[2-benzyl-6-[(3R,4R)-3-hydroxy-4-methoxypyrrolidin-1-yl]-3-pyridyl]ethynylcyclohexyl]piperidine;
1-[2-benzyl-6-[(3R,4R)-3-hydroxy-4-methoxypyrrolidin-1-yl]-3-pyridyl]ethynyl-N-methylcyclohexylamine;
2-[[1-[2-benzyl-6[(3R,4R)-3-hydroxy-4-methoxypyrrolidin-1-yl]-3-pyridyl]ethynylcyclohexyl]amino]ethanol;
3-[2-benzyl-6-[(3R,4R)-3-hydroxy-4-methoxypyrrolidin-1-yl]-3-pyridyl]-1,1-diethyl-2-propynylamine;
2-[2-benzyl-6-[(3R,4R)-3-hydroxy-4-methoxypyrrolidin-1-yl]-3-pyridyl]ethynylbicyclo[2.2.01]heptan-2-ol;
(3R)-3-[2-benzyl-4-(2-pyrrolidinon-1-yl)phenyl]ethynyl-3-quinuclidinol;
(3R)-3-[2-benzyl-4-[(3R,4R)-4-hydroxy-3-methoxy-2-pyrrolidinon-1-yl]phenyl]ethylnyl-3-quinuclidinol;
(3R)-3-[2-benzyl-4-[(3R,4R)-3,4-dimethoxy-2-pyrrolidinon-1-yl]phenyl]ethynyl-3-quinuclidinol;
(3R)-3-[2-benzyl-4-[(3R,4S)-3,4-dimethoxypyrrolidin-1-yl]phenyl]ethynyl-3-quinuclidinol;
(3R)-3-[2-benzyl-4-[(3R,4S)-3,4-dihydroxypyrrolidin-1-yl]phenyl]ethynyl-3-quinuclidinol;
(3R)-3-[2-benzyl-4-[cis-3-hydroxy-4-methoxypyrrolidin-1-yl]phenyl]ethynyl-3-quinuclidinol;
(3R)-3-[2-benzyl-4-[trans-3-hydroxy-4-methoxypyrrolidin-1-yl]phenyl]ethynyl-3-quinuclidinol;
3-[4-[2-benzyl-6-[(3R,4R)-3-hydroxy-4-methoxypyrrolidin-1-yl]-3-pyridyl]phenyl]-3-quinuclidinol;
(E)-3-[2-[2-benzyl-6-(2-pyrrolidinon-1-yl)pyridin-3-yloxy]-1-fluoroethynylidene]quinuclidine;
1-[2-benzyl-6-(3,3-ethylenedioxypyrrolidin-1-yl)-3-pyridyl]ethynylcyclohexylamine;
1-[2-benzyl-6-(4-methoxypiperidino)-3-pyridyl]ethynyl-cyclohexylamine;
4-[2-benzyl-6-[(3R,4R)-3,4-dimethoxypyrrolidin-1-yl]-3-pyridyl]ethynyl-exo-1-azaadamantan-4-ol; and
4-[2-benzyl-6-[(3R,4R)-3,4-dimethoxypyrrolidin-1-yl]-3-pyridyl]ethynyl-endo-1-azaadamantan-4-ol,
a salt thereof or a hydrate of them.

9. A pharmaceutical composition comprising a compound (I) represented by the formula:

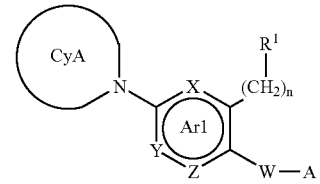

(I)

wherein R¹ represents an optionally substituted vinyl group or an aromatic ring which may be substituted;
n is an integer of 0 to 2;
X, Y, and Z are the same as or different from each other and each represents an optionally substituted carbon atom, or an optionally substituted nitrogen atom;
CyA represents a a pyrrolidine or piperidine;
W represents a chain expressed by
(1) optionally substituted —$CH_2$—$CH_2$—,
(2) optionally substituted —CH═CH—,
(3) —C≡C—,
(4) an optionally substituted phenylene group,
(5) a single bond,
(6) —NH—CO—,
(7) —CO—NH—,
(8) —NH—$CH_2$—,
(9) —$CH_2$—NH—,
(10) —$CH_2$—CO—,
(11) —CO—$CH_2$—,
(12) —O—$(CH_2)_m$—,
(13) —$(CH_2)_m$—O—, wherein m represents an integer of 0 to 5,
(14) —O—$CH_2$—$CR^2$═,
(15) —O—$CH_2$—$CHR^2$—, wherein R² represents a hydrogen atom, a $C_{1-6}$ alkyl group, or a halogen atom,
(16) —NH—$S(O)_1$—,
(17) —$S(O)_1$—NH—,
(18) —$CH_2$—$S(O)_1$— or

(19) —S(O)₁—CH₂—, wherein 1 represents 0, 1, or 2; and

A represents a group having any of the following structural formulae:

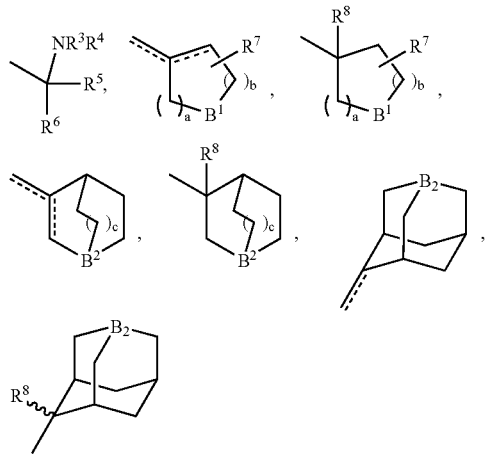

wherein R³ and R⁴ are independent of each other and each represents a hydrogen atom or an optionally substituted $C_{1-6}$ alkyl group;

R⁵ and R⁶ are independent of each other and each represents a hydrogen atom or an optionally substituted $C_{1-6}$ alkyl group;

R⁷ represents a hydrogen atom, an optionally substituted $C_{1-6}$ alkyl group, a hydroxyl group, an alkoxy group, a halogen atom or an optionally substituted amino group;

R⁸ represents a hydrogen atom, a hydroxyl group, an alkoxy group, a halogen atom or an optionally substituted amino group, B¹ represents an optionally substituted carbon atom, or an optionally substituted nitrogen atom;

B² represents an optionally substituted carbon atom or nitrogen atom;

a and b represent an integer of 0 to 4, provided that a+b is an integer of 0 to 4, c represents 0 or 1; and ------ represents a single bond or a double bond, provided that when c is 1 in which A is a quinuclidine having R⁸ represented by

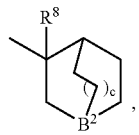

the case where R⁸ is a hydrogen atom or a hydroxyl group; Arl is an aromatic heterocycle selected from the group consisting of pyridine, pyrimidine, pyrazine, pyridazine and triazine thereof; and W is one of (1) to (3), (6) to (11) and (16) to (19) are excluded, a salt thereof or a hydrate thereof, and a pharmaceutically acceptable carrier.

10. A pharmaceutical composition comprising:
the compound of claim 2, a salt thereof or a hydrate thereof; and
a pharmaceutically acceptable carrier.

11. A method of treating at least one disease selected from the group consisting of hyperlipidemia, arterial sclerosis diseases, ischemic heart diseases, hypertension, coronary diseases, cerebrovascular diseases, aortic diseases, peripheral arterial diseases, angina pectoris, acute coronary syndromes and cardiac infarction, said method comprising:
administering a pharmaceutically effective amount of the compound according to claim 1 for the treatment of said at least one disease, a salt thereof or a hydrate thereof, to a patient in need thereof.

12. A method of treating at least one disease selected from the group consisting of hyperlipidemia, arterial sclerosis diseases, ischemic heart diseases, hypertension, coronary diseases, cerebrovascular diseases, aortic diseases, peripheral arterial diseases, angina pectoris, acute coronary syndromes and cardiac infarction, said method comprising:
administering an effective amount of the pharmaceutical composition of claim 9, a salt of the compound in the composition or a hydrate thereof for the treatment of said at least one disease to a patient in need thereof.

* * * * *